(12) United States Patent
Viswanathan et al.

(10) Patent No.: US 12,042,208 B2
(45) Date of Patent: Jul. 23, 2024

(54) SYSTEMS, DEVICES, AND METHODS FOR ABLATION USING SURGICAL CLAMPS

(71) Applicant: Boston Scientific Scimed Inc., Maple Grove, MN (US)

(72) Inventors: Raju Viswanathan, Mountain View, CA (US); Gary L. Long, Cincinnati, OH (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 17/087,433

(22) Filed: Nov. 2, 2020

(65) Prior Publication Data

US 2021/0045798 A1 Feb. 18, 2021

Related U.S. Application Data

(63) Continuation of application No. PCT/US2019/028943, filed on Apr. 24, 2019, which
(Continued)

(51) Int. Cl.
*A61B 18/14* (2006.01)
*A61B 5/283* (2021.01)
(Continued)

(52) U.S. Cl.
CPC ............. *A61B 18/14* (2013.01); *A61B 5/283* (2021.01); *A61B 18/1233* (2013.01); *A61B 2018/00351* (2013.01); *A61B 2018/00577* (2013.01); *A61B 2018/00613* (2013.01); *A61B 18/1445* (2013.01); *A61B 2018/145* (2013.01); *A61B 2018/1467* (2013.01)

(58) Field of Classification Search
CPC .. A61B 2018/00613; A61B 2018/1467; A61B 2018/165; A61N 1/327
See application file for complete search history.

(56) References Cited

U.S. PATENT DOCUMENTS

| 4,200,104 A | 4/1980 | Harris |
| 4,470,407 A | 9/1984 | Hussein |
| (Continued) | | |

FOREIGN PATENT DOCUMENTS

| EP | 1042990 A1 | 10/2000 |
| EP | 1125549 | 8/2001 |
| (Continued) | | |

OTHER PUBLICATIONS

Office Action for Canadian Application No. 2,881,462, dated Mar. 19, 2019, 5 pages.
(Continued)

*Primary Examiner* — Sean W Collins
(74) *Attorney, Agent, or Firm* — Nelson Mullins Riley & Scarborough LLP

(57) ABSTRACT

Systems, devices, and methods for electroporation ablation therapy are disclosed, with the device including a first jaw including a plurality of first electrodes and a second jaw including a plurality of second electrodes. The first jaw and the second jaw may be substantially rigid, elongate, and collectively define a longitudinal axis. The first jaw and the second jaw may be configured to engage tissue therebetween during use.

23 Claims, 18 Drawing Sheets

Related U.S. Application Data is a continuation of application No. 15/970,404, filed on May 3, 2018, now abandoned.

(51) Int. Cl.
  *A61B 18/12* (2006.01)
  *A61B 18/00* (2006.01)

(56) References Cited

U.S. PATENT DOCUMENTS

| | | |
|---|---|---|
| 4,739,759 A | 4/1988 | Rexroth et al. |
| 5,234,004 A | 8/1993 | Hascoet et al. |
| 5,242,441 A | 9/1993 | Avitall |
| 5,257,635 A | 11/1993 | Langberg |
| 5,281,213 A | 1/1994 | Milder et al. |
| 5,304,214 A | 4/1994 | DeFord et al. |
| 5,306,296 A | 4/1994 | Wright et al. |
| 5,334,193 A | 8/1994 | Nardella |
| 5,341,807 A | 8/1994 | Nardella |
| 5,342,301 A | 8/1994 | Saab |
| 5,398,683 A | 3/1995 | Edwards et al. |
| 5,443,463 A | 8/1995 | Stern et al. |
| 5,454,370 A | 10/1995 | Avitall |
| 5,515,848 A | 5/1996 | Corbett, III et al. |
| 5,531,685 A | 7/1996 | Hemmer et al. |
| 5,545,161 A | 8/1996 | Imran |
| 5,578,040 A | 11/1996 | Smith |
| 5,617,854 A | 4/1997 | Munsif |
| 5,624,430 A | 4/1997 | Eton et al. |
| 5,667,491 A | 9/1997 | Pliquett et al. |
| 5,672,170 A | 9/1997 | Cho |
| 5,700,243 A | 12/1997 | Narciso, Jr. |
| 5,702,438 A | 12/1997 | Avitall |
| 5,706,823 A | 1/1998 | Wodlinger |
| 5,722,400 A | 3/1998 | Ockuly et al. |
| 5,722,402 A | 3/1998 | Swanson et al. |
| 5,749,914 A | 5/1998 | Janssen |
| 5,779,699 A | 7/1998 | Lipson |
| 5,788,692 A | 8/1998 | Campbell et al. |
| 5,810,762 A | 9/1998 | Hofmann |
| 5,833,710 A | 11/1998 | Jacobson |
| 5,836,874 A | 11/1998 | Swanson et al. |
| 5,836,942 A | 11/1998 | Netherly et al. |
| 5,836,947 A | 11/1998 | Fleischman et al. |
| 5,843,154 A | 12/1998 | Osypka |
| 5,849,028 A | 12/1998 | Chen |
| 5,863,291 A | 1/1999 | Schaer |
| 5,868,736 A | 2/1999 | Swanson et al. |
| 5,871,523 A | 2/1999 | Fleischman et al. |
| 5,876,336 A | 3/1999 | Swanson et al. |
| 5,885,278 A | 3/1999 | Fleischman et al. |
| 5,895,404 A | 4/1999 | Ruiz |
| 5,899,917 A | 5/1999 | Edwards et al. |
| 5,904,709 A | 5/1999 | Arndt et al. |
| 5,913,854 A | 6/1999 | Maguire et al. |
| 5,916,158 A | 6/1999 | Webster, Jr. |
| 5,916,213 A | 6/1999 | Haissaguerre et al. |
| 5,921,924 A | 7/1999 | Avitall |
| 5,928,269 A | 7/1999 | Alt |
| 5,928,270 A | 7/1999 | Ramsey, III |
| 6,002,955 A | 12/1999 | Willems et al. |
| 6,006,131 A | 12/1999 | Cooper et al. |
| 6,009,351 A | 12/1999 | Flachman |
| 6,014,579 A | 1/2000 | Pomeranz et al. |
| 6,029,671 A | 2/2000 | Stevens et al. |
| 6,033,403 A | 3/2000 | Tu et al. |
| 6,035,238 A | 3/2000 | Ingle et al. |
| 6,045,550 A | 4/2000 | Simpson et al. |
| 6,068,653 A | 5/2000 | LaFontaine |
| 6,071,274 A | 6/2000 | Thompson et al. |
| 6,071,281 A | 6/2000 | Burnside et al. |
| 6,074,389 A | 6/2000 | Levine et al. |
| 6,076,012 A | 6/2000 | Swanson et al. |
| 6,090,104 A | 7/2000 | Webster, Jr. |
| 6,096,036 A | 8/2000 | Bowe et al. |
| 6,113,595 A | 9/2000 | Muntermann |
| 6,119,041 A | 9/2000 | Pomeranz et al. |
| 6,120,500 A | 9/2000 | Bednarek et al. |
| 6,146,381 A | 11/2000 | Bowe et al. |
| 6,164,283 A | 12/2000 | Lesh |
| 6,167,291 A | 12/2000 | Barajas et al. |
| 6,171,305 B1 | 1/2001 | Sherman |
| 6,216,034 B1 | 4/2001 | Hofmann et al. |
| 6,219,582 B1 | 4/2001 | Hofstad et al. |
| 6,223,085 B1 | 4/2001 | Dann et al. |
| 6,231,518 B1 | 5/2001 | Grabek et al. |
| 6,245,064 B1 | 6/2001 | Lesh et al. |
| 6,251,107 B1 | 6/2001 | Schaer |
| 6,251,128 B1 | 6/2001 | Knopp et al. |
| 6,270,476 B1 | 8/2001 | Santoianni et al. |
| 6,272,384 B1 | 8/2001 | Simon et al. |
| 6,287,306 B1 | 9/2001 | Kroll et al. |
| 6,314,963 B1 | 11/2001 | Vaska et al. |
| 6,322,559 B1 | 11/2001 | Daulton et al. |
| 6,350,263 B1 | 2/2002 | Wetzig et al. |
| 6,370,412 B1 | 4/2002 | Armoundas et al. |
| 6,391,024 B1 | 5/2002 | Sun et al. |
| 6,447,505 B2 | 9/2002 | McGovern et al. |
| 6,464,699 B1 | 10/2002 | Swanson |
| 6,470,211 B1 | 10/2002 | Ideker et al. |
| 6,502,576 B1 | 1/2003 | Lesh |
| 6,503,247 B2 | 1/2003 | Swartz et al. |
| 6,517,534 B1 | 2/2003 | McGovern et al. |
| 6,527,724 B1 | 3/2003 | Fenici |
| 6,527,767 B2 | 3/2003 | Wang et al. |
| 6,592,581 B2 | 7/2003 | Bowe |
| 6,595,991 B2 | 7/2003 | Tollner et al. |
| 6,607,520 B2 | 8/2003 | Keane |
| 6,623,480 B1 | 9/2003 | Kuo et al. |
| 6,638,278 B2 | 10/2003 | Falwell et al. |
| 6,666,863 B2 | 12/2003 | Wentzel et al. |
| 6,669,693 B2 | 12/2003 | Friedman |
| 6,702,811 B2 | 3/2004 | Stewart et al. |
| 6,719,756 B1 | 4/2004 | Muntermann |
| 6,723,092 B2 | 4/2004 | Brown et al. |
| 6,728,563 B2 | 4/2004 | Rashidi |
| 6,743,225 B2 | 6/2004 | Sanchez et al. |
| 6,743,226 B2 | 6/2004 | Cosman et al. |
| 6,743,239 B1 | 6/2004 | Kuehn et al. |
| 6,764,486 B2 | 7/2004 | Natale |
| 6,780,181 B2 | 8/2004 | Kroll et al. |
| 6,805,128 B1 | 10/2004 | Pless |
| 6,807,447 B2 | 10/2004 | Griffin, III |
| 6,892,091 B1 | 5/2005 | Ben-Haim et al. |
| 6,893,438 B2 | 5/2005 | Hall et al. |
| 6,926,714 B1 | 8/2005 | Sra |
| 6,955,173 B2 | 10/2005 | Lesh |
| 6,960,206 B2 | 11/2005 | Keane |
| 6,960,207 B2 | 11/2005 | Vanney et al. |
| 6,972,016 B2 | 12/2005 | Hill, III et al. |
| 6,973,339 B2 | 12/2005 | Govari |
| 6,979,331 B2 | 12/2005 | Hintringer et al. |
| 6,984,232 B2 | 1/2006 | Vanney et al. |
| 6,985,776 B2 | 1/2006 | Kane et al. |
| 7,001,383 B2 | 2/2006 | Keidar |
| 7,041,095 B2 | 5/2006 | Wang et al. |
| 7,113,831 B2 | 9/2006 | Hooven |
| 7,171,263 B2 | 1/2007 | Darvish et al. |
| 7,182,725 B2 | 2/2007 | Bonan et al. |
| 7,195,628 B2 | 3/2007 | Falkenberg |
| 7,207,988 B2 | 4/2007 | Leckrone et al. |
| 7,207,989 B2 | 4/2007 | Pike, Jr. et al. |
| 7,229,402 B2 | 6/2007 | Diaz et al. |
| 7,229,437 B2 | 6/2007 | Johnson et al. |
| 7,250,049 B2 | 7/2007 | Roop et al. |
| 7,285,116 B2 | 10/2007 | de la Rama et al. |
| 7,285,119 B2 | 10/2007 | Stewart et al. |
| 7,326,208 B2 | 2/2008 | Vanney et al. |
| 7,346,379 B2 | 3/2008 | Eng et al. |
| 7,367,974 B2 | 5/2008 | Haemmerich et al. |
| 7,374,567 B2 | 5/2008 | Heuser |
| 7,387,629 B2 | 6/2008 | Vanney et al. |
| 7,387,630 B2 | 6/2008 | Mest |
| 7,387,636 B2 | 6/2008 | Cohn et al. |

(56) References Cited

U.S. PATENT DOCUMENTS

| | | |
|---|---|---|
| 7,416,552 B2 | 8/2008 | Paul et al. |
| 7,419,477 B2 | 9/2008 | Simpson et al. |
| 7,419,489 B2 | 9/2008 | Vanney et al. |
| 7,422,591 B2 | 9/2008 | Phan |
| 7,429,261 B2 | 9/2008 | Kunis et al. |
| 7,435,248 B2 | 10/2008 | Taimisto et al. |
| 7,513,896 B2 | 4/2009 | Orszulak |
| 7,527,625 B2 | 5/2009 | Knight et al. |
| 7,578,816 B2 | 8/2009 | Boveja et al. |
| 7,588,567 B2 | 9/2009 | Boveja et al. |
| 7,623,899 B2 | 11/2009 | Worley et al. |
| 7,678,108 B2 | 3/2010 | Chrisitian et al. |
| 7,681,579 B2 | 3/2010 | Schwartz |
| 7,771,421 B2 | 8/2010 | Stewart et al. |
| 7,805,182 B2 | 9/2010 | Weese et al. |
| 7,850,642 B2 | 12/2010 | Moll et al. |
| 7,850,685 B2 | 12/2010 | Kunis et al. |
| 7,857,808 B2 | 12/2010 | Oral et al. |
| 7,857,809 B2 | 12/2010 | Drysen |
| 7,869,865 B2 | 1/2011 | Govari et al. |
| 7,896,873 B2 | 3/2011 | Hiller et al. |
| 7,917,211 B2 | 3/2011 | Zacouto |
| 7,918,819 B2 | 4/2011 | Karmarkar et al. |
| 7,918,850 B2 | 4/2011 | Govari et al. |
| 7,922,714 B2 | 4/2011 | Stevens-Wright |
| 7,955,827 B2 | 6/2011 | Rubinsky et al. |
| 8,048,067 B2 | 11/2011 | Davalos et al. |
| 8,048,072 B2 | 11/2011 | Verin et al. |
| 8,100,895 B2 | 1/2012 | Panos et al. |
| 8,100,900 B2 | 1/2012 | Prinz et al. |
| 8,108,069 B2 | 1/2012 | Stahler et al. |
| 8,133,220 B2 | 3/2012 | Lee et al. |
| 8,137,342 B2 | 3/2012 | Crossman |
| 8,145,289 B2 | 3/2012 | Calabro' et al. |
| 8,147,486 B2 | 4/2012 | Honour et al. |
| 8,160,690 B2 | 4/2012 | Wilfley et al. |
| 8,175,680 B2 | 5/2012 | Panescu |
| 8,182,477 B2 | 5/2012 | Orszulak et al. |
| 8,206,384 B2 | 6/2012 | Falwell et al. |
| 8,206,385 B2 | 6/2012 | Stangenes et al. |
| 8,216,221 B2 | 7/2012 | Ibrahim et al. |
| 8,221,411 B2 | 7/2012 | Francischelli et al. |
| 8,226,648 B2 | 7/2012 | Paul et al. |
| 8,228,065 B2 | 7/2012 | Wirtz et al. |
| 8,235,986 B2 | 8/2012 | Kulesa et al. |
| 8,235,988 B2 | 8/2012 | Davis et al. |
| 8,251,986 B2 | 8/2012 | Chornenky et al. |
| 8,282,631 B2 | 10/2012 | Davalos et al. |
| 8,287,532 B2 | 10/2012 | Carroll et al. |
| 8,414,508 B2 | 4/2013 | Thapliyal et al. |
| 8,430,875 B2 | 4/2013 | Ibrahim et al. |
| 8,433,394 B2 | 4/2013 | Harlev et al. |
| 8,449,535 B2 | 5/2013 | Deno et al. |
| 8,454,594 B2 | 6/2013 | Demarais et al. |
| 8,463,368 B2 | 6/2013 | Harlev et al. |
| 8,475,450 B2 | 7/2013 | Govari et al. |
| 8,486,063 B2 | 7/2013 | Werneth et al. |
| 8,500,733 B2 | 8/2013 | Watson |
| 8,535,304 B2 | 9/2013 | Sklar et al. |
| 8,538,501 B2 | 9/2013 | Venkatachalam et al. |
| 8,562,588 B2 | 10/2013 | Hobbs et al. |
| 8,568,406 B2 | 10/2013 | Harlev et al. |
| 8,568,410 B2 | 10/2013 | Vakharia et al. |
| 8,571,635 B2 | 10/2013 | McGee |
| 8,571,647 B2 | 10/2013 | Harlev et al. |
| 8,579,897 B2 | 11/2013 | Vakharia et al. |
| 8,585,695 B2 | 11/2013 | Shih |
| 8,588,885 B2 | 11/2013 | Hall et al. |
| 8,597,288 B2 | 12/2013 | Christian |
| 8,608,735 B2 | 12/2013 | Govari et al. |
| 8,628,522 B2 | 1/2014 | Ibrahim et al. |
| 8,632,534 B2 | 1/2014 | Pearson et al. |
| 8,647,338 B2 | 2/2014 | Chornenky et al. |
| 8,708,952 B2 | 4/2014 | Cohen et al. |
| 8,734,442 B2 | 5/2014 | Cao et al. |
| 8,771,267 B2 | 7/2014 | Kunis et al. |
| 8,795,310 B2 | 8/2014 | Fung et al. |
| 8,808,273 B2 | 8/2014 | Caples et al. |
| 8,808,281 B2 | 8/2014 | Emons et al. |
| 8,834,461 B2 | 9/2014 | Werneth et al. |
| 8,834,464 B2 | 9/2014 | Stewart et al. |
| 8,868,169 B2 | 10/2014 | Narayan et al. |
| 8,876,817 B2 | 11/2014 | Avitall et al. |
| 8,880,195 B2 | 11/2014 | Azure |
| 8,886,309 B2 | 11/2014 | Luther et al. |
| 8,903,488 B2 | 12/2014 | Callas et al. |
| 8,920,411 B2 | 12/2014 | Gelbart et al. |
| 8,926,589 B2 | 1/2015 | Govari |
| 8,932,287 B2 | 1/2015 | Gelbart et al. |
| 8,945,117 B2 | 2/2015 | Bencini |
| 8,979,841 B2 | 3/2015 | Kunis et al. |
| 8,986,278 B2 | 3/2015 | Fung et al. |
| 9,002,442 B2 | 4/2015 | Harley et al. |
| 9,005,189 B2 | 4/2015 | Davalos et al. |
| 9,005,194 B2 | 4/2015 | Oral et al. |
| 9,011,425 B2 | 4/2015 | Fischer et al. |
| 9,044,245 B2 | 6/2015 | Condie et al. |
| 9,055,959 B2 | 6/2015 | Vaska et al. |
| 9,072,518 B2 | 7/2015 | Swanson |
| 9,078,667 B2 | 7/2015 | Besser et al. |
| 9,101,374 B1 | 8/2015 | Hoch et al. |
| 9,119,533 B2 | 9/2015 | Ghaffari |
| 9,119,634 B2 | 9/2015 | Gelbart et al. |
| 9,131,897 B2 | 9/2015 | Harada et al. |
| 9,155,590 B2 | 10/2015 | Mathur |
| 9,162,037 B2 | 10/2015 | Belson et al. |
| 9,179,972 B2 | 11/2015 | Olson |
| 9,186,481 B2 | 11/2015 | Avitall et al. |
| 9,192,769 B2 | 11/2015 | Donofrio et al. |
| 9,211,405 B2 | 12/2015 | Mahapatra et al. |
| 9,216,055 B2 | 12/2015 | Spence et al. |
| 9,233,248 B2 | 1/2016 | Luther et al. |
| 9,237,926 B2 | 1/2016 | Nollert et al. |
| 9,262,252 B2 | 2/2016 | Kirkpatrick et al. |
| 9,277,957 B2 | 3/2016 | Long et al. |
| 9,282,910 B2 | 3/2016 | Narayan et al. |
| 9,289,258 B2 | 3/2016 | Cohen |
| 9,289,606 B2 | 3/2016 | Paul et al. |
| 9,295,516 B2 | 3/2016 | Pearson et al. |
| 9,301,801 B2 | 4/2016 | Scheib |
| 9,375,268 B2 | 6/2016 | Long |
| 9,414,881 B2 | 8/2016 | Callas et al. |
| 9,468,495 B2 | 10/2016 | Kunis et al. |
| 9,474,486 B2 | 10/2016 | Eliason et al. |
| 9,474,574 B2 | 10/2016 | Ibrahim et al. |
| 9,480,525 B2 | 11/2016 | Lopes et al. |
| 9,486,272 B2 | 11/2016 | Bonyak et al. |
| 9,486,273 B2 | 11/2016 | Lopes et al. |
| 9,492,227 B2 | 11/2016 | Lopes et al. |
| 9,492,228 B2 | 11/2016 | Lopes et al. |
| 9,517,103 B2 | 12/2016 | Panescu et al. |
| 9,526,573 B2 | 12/2016 | Lopes et al. |
| 9,532,831 B2 | 1/2017 | Reinders et al. |
| 9,539,010 B2 | 1/2017 | Gagner et al. |
| 9,554,848 B2 | 1/2017 | Stewart et al. |
| 9,554,851 B2 | 1/2017 | Sklar et al. |
| 9,610,118 B2 | 4/2017 | Olson |
| 9,700,368 B2 | 7/2017 | Callas et al. |
| 9,724,170 B2 | 8/2017 | Mickelsen |
| 9,757,193 B2 | 9/2017 | Zarins et al. |
| 9,782,099 B2 | 10/2017 | Williams et al. |
| 9,795,442 B2 | 10/2017 | Salahieh et al. |
| 9,861,802 B2 | 1/2018 | Mickelsen |
| 9,913,685 B2 | 3/2018 | Clark et al. |
| 9,931,487 B2 | 4/2018 | Quinn et al. |
| 9,987,081 B1 | 6/2018 | Bowers et al. |
| 9,999,465 B2 | 6/2018 | Long et al. |
| 10,016,232 B1 | 7/2018 | Bowers et al. |
| 10,130,423 B1 | 11/2018 | Viswanathan et al. |
| 10,172,673 B2 | 1/2019 | Viswanathan et al. |
| 10,322,286 B2 | 6/2019 | Viswanathan et al. |
| 10,433,906 B2 | 10/2019 | Mickelsen |
| 10,433,908 B2 | 10/2019 | Viswanathan et al. |
| 10,507,302 B2 | 12/2019 | Leeflang et al. |

(56) References Cited

U.S. PATENT DOCUMENTS

| | | |
|---|---|---|
| 10,512,505 B2 | 12/2019 | Viswanathan |
| 10,512,779 B2 | 12/2019 | Viswanathan et al. |
| 10,517,672 B2 | 12/2019 | Long |
| 10,624,693 B2 | 4/2020 | Mickelsen et al. |
| 10,835,314 B2 | 11/2020 | Long et al. |
| 11,020,180 B2 | 6/2021 | Viswanathan et al. |
| 2001/0000791 A1 | 5/2001 | Suorsa et al. |
| 2001/0007070 A1 | 7/2001 | Stewart et al. |
| 2001/0044624 A1 | 11/2001 | Seraj et al. |
| 2002/0052602 A1 | 5/2002 | Wang et al. |
| 2002/0077627 A1 | 6/2002 | Johnson et al. |
| 2002/0087169 A1 | 7/2002 | Brock et al. |
| 2002/0091384 A1 | 7/2002 | Hooven et al. |
| 2002/0095176 A1 | 7/2002 | Liddicoat et al. |
| 2002/0111618 A1 | 8/2002 | Stewart et al. |
| 2002/0156526 A1 | 10/2002 | Hlavka et al. |
| 2002/0161323 A1 | 10/2002 | Miller et al. |
| 2002/0169445 A1 | 11/2002 | Jain et al. |
| 2002/0177765 A1 | 11/2002 | Bowe et al. |
| 2002/0183638 A1 | 12/2002 | Swanson |
| 2003/0014098 A1 | 1/2003 | Quijano et al. |
| 2003/0018374 A1 | 1/2003 | Paulos |
| 2003/0023287 A1 | 1/2003 | Edwards et al. |
| 2003/0028189 A1 | 2/2003 | Woloszko et al. |
| 2003/0050637 A1 | 3/2003 | Maguire et al. |
| 2003/0114849 A1 | 6/2003 | Ryan |
| 2003/0125729 A1 | 7/2003 | Hooven et al. |
| 2003/0130598 A1 | 7/2003 | Manning et al. |
| 2003/0130711 A1 | 7/2003 | Pearson et al. |
| 2003/0204161 A1 | 10/2003 | Ferek Petric |
| 2003/0229379 A1 | 12/2003 | Ramsey |
| 2004/0039382 A1 | 2/2004 | Kroll et al. |
| 2004/0049181 A1 | 3/2004 | Stewart et al. |
| 2004/0049182 A1 | 3/2004 | Koblish et al. |
| 2004/0082859 A1 | 4/2004 | Schaer |
| 2004/0082948 A1 | 4/2004 | Stewart et al. |
| 2004/0087939 A1 | 5/2004 | Eggers et al. |
| 2004/0111087 A1 | 6/2004 | Stern et al. |
| 2004/0199157 A1 | 10/2004 | Palanker et al. |
| 2004/0215139 A1 | 10/2004 | Cohen |
| 2004/0231683 A1 | 11/2004 | Eng et al. |
| 2004/0236360 A1 | 11/2004 | Cohn et al. |
| 2004/0254607 A1 | 12/2004 | Wittenberger et al. |
| 2004/0267337 A1 | 12/2004 | Hayzelden |
| 2005/0033282 A1 | 2/2005 | Hooven |
| 2005/0187545 A1 | 8/2005 | Hooven et al. |
| 2005/0222632 A1 | 10/2005 | Obino |
| 2005/0251130 A1 | 11/2005 | Boveja et al. |
| 2005/0261672 A1 | 11/2005 | Deem et al. |
| 2006/0009755 A1 | 1/2006 | Sra |
| 2006/0009759 A1 | 1/2006 | Christian et al. |
| 2006/0015095 A1 | 1/2006 | Desinger et al. |
| 2006/0015165 A1 | 1/2006 | Bertolero et al. |
| 2006/0024359 A1 | 2/2006 | Walker et al. |
| 2006/0058781 A1 | 3/2006 | Long |
| 2006/0111702 A1 | 5/2006 | Oral et al. |
| 2006/0142801 A1 | 6/2006 | Demarais et al. |
| 2006/0167448 A1 | 7/2006 | Kozel |
| 2006/0217703 A1 | 9/2006 | Chornenky et al. |
| 2006/0241734 A1 | 10/2006 | Marshall et al. |
| 2006/0264752 A1 | 11/2006 | Rubinsky et al. |
| 2006/0270900 A1 | 11/2006 | Chin et al. |
| 2006/0287648 A1 | 12/2006 | Schwartz |
| 2006/0293730 A1 | 12/2006 | Rubinsky et al. |
| 2006/0293731 A1 | 12/2006 | Rubinsky et al. |
| 2007/0005053 A1 | 1/2007 | Dando |
| 2007/0021744 A1 | 1/2007 | Creighton |
| 2007/0060989 A1 | 3/2007 | Deem et al. |
| 2007/0066972 A1 | 3/2007 | Ormsby et al. |
| 2007/0129721 A1 | 6/2007 | Phan et al. |
| 2007/0129760 A1 | 6/2007 | Demarais et al. |
| 2007/0156135 A1 | 7/2007 | Rubinsky et al. |
| 2007/0167740 A1 | 7/2007 | Grunewald et al. |
| 2007/0167940 A1 | 7/2007 | Stevens-Wright |
| 2007/0173878 A1 | 7/2007 | Heuser |
| 2007/0191826 A1 | 8/2007 | Park |
| 2007/0208329 A1 | 9/2007 | Ward et al. |
| 2007/0225589 A1 | 9/2007 | Viswanathan |
| 2007/0249923 A1 | 10/2007 | Keenan |
| 2007/0260223 A1 | 11/2007 | Scheibe et al. |
| 2007/0270792 A1 | 11/2007 | Hennemann et al. |
| 2008/0009855 A1 | 1/2008 | Hamou |
| 2008/0033426 A1 | 2/2008 | Machell |
| 2008/0065061 A1 | 3/2008 | Viswanathan |
| 2008/0086120 A1 | 4/2008 | Mirza et al. |
| 2008/0091195 A1 | 4/2008 | Silwa et al. |
| 2008/0103545 A1 | 5/2008 | Bolea et al. |
| 2008/0132885 A1 | 6/2008 | Rubinsky et al. |
| 2008/0161789 A1 | 7/2008 | Thao et al. |
| 2008/0172048 A1 | 7/2008 | Martin et al. |
| 2008/0200913 A1 | 8/2008 | Viswanathan |
| 2008/0208118 A1 | 8/2008 | Goldman |
| 2008/0243214 A1 | 10/2008 | Koblish |
| 2008/0281322 A1 | 11/2008 | Sherman et al. |
| 2008/0300574 A1 | 12/2008 | Belson et al. |
| 2008/0300588 A1 | 12/2008 | Groth et al. |
| 2009/0024084 A1 | 1/2009 | Khosla et al. |
| 2009/0048591 A1 | 2/2009 | Ibrahim et al. |
| 2009/0062788 A1 | 3/2009 | Long et al. |
| 2009/0062792 A1 | 3/2009 | Vakharia et al. |
| 2009/0076500 A1 | 3/2009 | Azure |
| 2009/0105654 A1 | 4/2009 | Kurth et al. |
| 2009/0138009 A1 | 5/2009 | Viswanathan et al. |
| 2009/0149917 A1 | 6/2009 | Whitehurst et al. |
| 2009/0163905 A1 | 6/2009 | Winkler et al. |
| 2009/0228003 A1 | 9/2009 | Sinelnikov |
| 2009/0240248 A1 | 9/2009 | Deford et al. |
| 2009/0275827 A1 | 11/2009 | Aiken et al. |
| 2009/0281477 A1 | 11/2009 | Mikus et al. |
| 2009/0306651 A1 | 12/2009 | Schneider |
| 2010/0004623 A1 | 1/2010 | Hamilton et al. |
| 2010/0023004 A1 | 1/2010 | Francischelli et al. |
| 2010/0137861 A1 | 6/2010 | Soroff et al. |
| 2010/0185140 A1 | 7/2010 | Kassab et al. |
| 2010/0185186 A1 | 7/2010 | Longoria |
| 2010/0191112 A1 | 7/2010 | Demarais et al. |
| 2010/0191232 A1 | 7/2010 | Boveda |
| 2010/0241185 A1 | 9/2010 | Mahapatra et al. |
| 2010/0261994 A1 | 10/2010 | Davalos et al. |
| 2010/0274238 A1 | 10/2010 | Klimovitch |
| 2010/0280513 A1 | 11/2010 | Juergen et al. |
| 2010/0280539 A1 | 11/2010 | Miyoshi et al. |
| 2010/0292687 A1 | 11/2010 | Kauphusman et al. |
| 2010/0312096 A1 | 12/2010 | Guttman et al. |
| 2010/0312300 A1 | 12/2010 | Ryu et al. |
| 2010/0331838 A1* | 12/2010 | Ibrahim ............ A61B 17/28 600/301 |
| 2011/0028962 A1 | 2/2011 | Werneth et al. |
| 2011/0028964 A1 | 2/2011 | Edwards |
| 2011/0040199 A1 | 2/2011 | Hopenfeld |
| 2011/0098694 A1 | 4/2011 | Long |
| 2011/0106221 A1 | 5/2011 | Neal, II et al. |
| 2011/0130708 A1 | 6/2011 | Perry et al. |
| 2011/0144524 A1 | 6/2011 | Fish et al. |
| 2011/0144633 A1 | 6/2011 | Govari |
| 2011/0160785 A1 | 6/2011 | Mori et al. |
| 2011/0190659 A1 | 8/2011 | Long et al. |
| 2011/0190727 A1 | 8/2011 | Edmunds et al. |
| 2011/0208185 A1 | 8/2011 | Diamant et al. |
| 2011/0213231 A1 | 9/2011 | Hall et al. |
| 2011/0276047 A1 | 11/2011 | Sklar et al. |
| 2011/0276075 A1 | 11/2011 | Fung et al. |
| 2011/0288544 A1 | 11/2011 | Verin et al. |
| 2011/0288547 A1 | 11/2011 | Morgan et al. |
| 2011/0313417 A1 | 12/2011 | De La Rama et al. |
| 2012/0029512 A1 | 2/2012 | Willard et al. |
| 2012/0046570 A1 | 2/2012 | Villegas et al. |
| 2012/0053581 A1 | 3/2012 | Wittkampf et al. |
| 2012/0059255 A1 | 3/2012 | Paul et al. |
| 2012/0071872 A1 | 3/2012 | Rubinsky et al. |
| 2012/0078320 A1 | 3/2012 | Schotzko et al. |
| 2012/0078343 A1 | 3/2012 | Fish |
| 2012/0089089 A1 | 4/2012 | Swain et al. |
| 2012/0095459 A1 | 4/2012 | Callas et al. |

(56) References Cited

U.S. PATENT DOCUMENTS

| | | |
|---|---|---|
| 2012/0101413 A1 | 4/2012 | Beetel et al. |
| 2012/0158021 A1 | 6/2012 | Morrill |
| 2012/0165667 A1 | 6/2012 | Altmann et al. |
| 2012/0172859 A1 | 7/2012 | Condie et al. |
| 2012/0172867 A1 | 7/2012 | Ryu et al. |
| 2012/0197100 A1 | 8/2012 | Razavi et al. |
| 2012/0209260 A1 | 8/2012 | Lambert et al. |
| 2012/0220998 A1 | 8/2012 | Long et al. |
| 2012/0265198 A1 | 10/2012 | Crow et al. |
| 2012/0283582 A1 | 11/2012 | Mahapatra et al. |
| 2012/0303019 A1 | 11/2012 | Zhao et al. |
| 2012/0310052 A1 | 12/2012 | Mahapatra et al. |
| 2012/0310230 A1 | 12/2012 | Willis |
| 2012/0310237 A1 | 12/2012 | Swanson |
| 2012/0316557 A1 | 12/2012 | Sartor et al. |
| 2013/0030430 A1 | 1/2013 | Stewart et al. |
| 2013/0060247 A1 | 3/2013 | Sklar et al. |
| 2013/0060248 A1 | 3/2013 | Sklar et al. |
| 2013/0079768 A1 | 3/2013 | De Luca et al. |
| 2013/0090651 A1 | 4/2013 | Smith |
| 2013/0096655 A1 | 4/2013 | Moffitt et al. |
| 2013/0103027 A1 | 4/2013 | Sklar et al. |
| 2013/0103064 A1 | 4/2013 | Arenson et al. |
| 2013/0131662 A1 | 5/2013 | Wittkampf |
| 2013/0158538 A1 | 6/2013 | Govari |
| 2013/0158621 A1 | 6/2013 | Ding et al. |
| 2013/0172715 A1 | 7/2013 | Just et al. |
| 2013/0172864 A1 | 7/2013 | Ibrahim et al. |
| 2013/0172875 A1 | 7/2013 | Govari et al. |
| 2013/0184702 A1 | 7/2013 | Neal, II et al. |
| 2013/0218157 A1 | 8/2013 | Callas et al. |
| 2013/0226174 A1 | 8/2013 | Ibrahim et al. |
| 2013/0237984 A1 | 9/2013 | Sklar |
| 2013/0253415 A1 | 9/2013 | Sano et al. |
| 2013/0274733 A1* | 10/2013 | Hancock ............... A61B 18/18 606/33 |
| 2013/0296679 A1 | 11/2013 | Condie et al. |
| 2013/0310829 A1 | 11/2013 | Cohen |
| 2013/0317385 A1 | 11/2013 | Sklar et al. |
| 2013/0331831 A1 | 12/2013 | Werneth et al. |
| 2013/0338467 A1 | 12/2013 | Grasse et al. |
| 2014/0005664 A1 | 1/2014 | Govari et al. |
| 2014/0024911 A1 | 1/2014 | Harlev et al. |
| 2014/0039288 A1 | 2/2014 | Shih |
| 2014/0051993 A1 | 2/2014 | McGee |
| 2014/0052118 A1 | 2/2014 | Laske et al. |
| 2014/0052126 A1 | 2/2014 | Long et al. |
| 2014/0052216 A1 | 2/2014 | Long et al. |
| 2014/0058377 A1 | 2/2014 | Deem et al. |
| 2014/0081113 A1 | 3/2014 | Cohen et al. |
| 2014/0100563 A1 | 4/2014 | Govari et al. |
| 2014/0107644 A1 | 4/2014 | Falwell et al. |
| 2014/0142408 A1 | 5/2014 | De La Rama et al. |
| 2014/0148804 A1 | 5/2014 | Ward et al. |
| 2014/0163480 A1 | 6/2014 | Govari et al. |
| 2014/0163546 A1 | 6/2014 | Govari et al. |
| 2014/0171942 A1 | 6/2014 | Werneth et al. |
| 2014/0180035 A1 | 6/2014 | Anderson |
| 2014/0187916 A1 | 7/2014 | Clark et al. |
| 2014/0194716 A1 | 7/2014 | Diep et al. |
| 2014/0194864 A1* | 7/2014 | Martin .................... A61B 18/18 606/33 |
| 2014/0194867 A1 | 7/2014 | Fish et al. |
| 2014/0200567 A1 | 7/2014 | Cox et al. |
| 2014/0235986 A1 | 8/2014 | Harlev et al. |
| 2014/0235988 A1 | 8/2014 | Ghosh |
| 2014/0235989 A1 | 8/2014 | Wodlinger et al. |
| 2014/0243851 A1 | 8/2014 | Cohen et al. |
| 2014/0276760 A1 | 9/2014 | Bonyak et al. |
| 2014/0276782 A1 | 9/2014 | Paskar |
| 2014/0276791 A1 | 9/2014 | Ku et al. |
| 2014/0288556 A1 | 9/2014 | Ibrahim et al. |
| 2014/0303721 A1 | 10/2014 | Fung et al. |
| 2014/0343549 A1 | 11/2014 | Spear et al. |
| 2014/0364845 A1 | 12/2014 | Rashidi |
| 2014/0371613 A1 | 12/2014 | Narayan et al. |
| 2015/0005767 A1 | 1/2015 | Werneth et al. |
| 2015/0011995 A1 | 1/2015 | Avitall et al. |
| 2015/0066108 A1 | 3/2015 | Shi et al. |
| 2015/0119674 A1 | 4/2015 | Fischell et al. |
| 2015/0126840 A1 | 5/2015 | Thakur et al. |
| 2015/0133914 A1 | 5/2015 | Koblish |
| 2015/0138977 A1 | 5/2015 | Dacosta |
| 2015/0141978 A1 | 5/2015 | Subramaniam et al. |
| 2015/0142041 A1 | 5/2015 | Kendale et al. |
| 2015/0148796 A1 | 5/2015 | Bencini |
| 2015/0150472 A1 | 6/2015 | Harlev et al. |
| 2015/0157402 A1 | 6/2015 | Kunis et al. |
| 2015/0157412 A1 | 6/2015 | Wallace et al. |
| 2015/0164584 A1 | 6/2015 | Davalos et al. |
| 2015/0173824 A1 | 6/2015 | Davalos et al. |
| 2015/0173828 A1 | 6/2015 | Avitall |
| 2015/0174404 A1 | 6/2015 | Rousso et al. |
| 2015/0182740 A1 | 7/2015 | Mickelsen |
| 2015/0196217 A1 | 7/2015 | Harlev et al. |
| 2015/0223726 A1 | 8/2015 | Harlev et al. |
| 2015/0230699 A1 | 8/2015 | Berul et al. |
| 2015/0258344 A1 | 9/2015 | Tandri et al. |
| 2015/0265342 A1 | 9/2015 | Long et al. |
| 2015/0265344 A1 | 9/2015 | Aktas et al. |
| 2015/0272656 A1 | 10/2015 | Chen |
| 2015/0272664 A9 | 10/2015 | Cohen |
| 2015/0272667 A1 | 10/2015 | Govari et al. |
| 2015/0282729 A1 | 10/2015 | Harlev et al. |
| 2015/0289923 A1 | 10/2015 | Davalos et al. |
| 2015/0304879 A1 | 10/2015 | Dacosta |
| 2015/0320481 A1 | 11/2015 | Cosman et al. |
| 2015/0321021 A1 | 11/2015 | Tandri et al. |
| 2015/0342532 A1 | 12/2015 | Basu et al. |
| 2015/0343212 A1 | 12/2015 | Rousso et al. |
| 2015/0351836 A1 | 12/2015 | Prutchi |
| 2015/0359583 A1 | 12/2015 | Swanson |
| 2016/0000500 A1 | 1/2016 | Salahieh et al. |
| 2016/0008061 A1 | 1/2016 | Fung et al. |
| 2016/0008065 A1 | 1/2016 | Gliner et al. |
| 2016/0029960 A1 | 2/2016 | Toth et al. |
| 2016/0038772 A1 | 2/2016 | Thapliyal et al. |
| 2016/0051204 A1 | 2/2016 | Harlev et al. |
| 2016/0051324 A1 | 2/2016 | Stewart et al. |
| 2016/0058493 A1 | 3/2016 | Neal, II et al. |
| 2016/0058506 A1 | 3/2016 | Spence et al. |
| 2016/0066993 A1 | 3/2016 | Avitall et al. |
| 2016/0074679 A1 | 3/2016 | Thapliyal et al. |
| 2016/0095531 A1 | 4/2016 | Narayan et al. |
| 2016/0095642 A1 | 4/2016 | Deno et al. |
| 2016/0095653 A1 | 4/2016 | Lambert et al. |
| 2016/0100797 A1 | 4/2016 | Mahapatra et al. |
| 2016/0100884 A1 | 4/2016 | Fay et al. |
| 2016/0106498 A1 | 4/2016 | Highsmith et al. |
| 2016/0106500 A1 | 4/2016 | Olson |
| 2016/0113709 A1 | 4/2016 | Maor |
| 2016/0113712 A1 | 4/2016 | Cheung et al. |
| 2016/0120564 A1 | 5/2016 | Kirkpatrick et al. |
| 2016/0128770 A1 | 5/2016 | Afonso et al. |
| 2016/0166167 A1 | 6/2016 | Narayan et al. |
| 2016/0166310 A1 | 6/2016 | Stewart et al. |
| 2016/0166311 A1 | 6/2016 | Long et al. |
| 2016/0174865 A1 | 6/2016 | Stewart et al. |
| 2016/0183877 A1 | 6/2016 | Williams et al. |
| 2016/0184003 A1 | 6/2016 | Srimathveeravalli et al. |
| 2016/0184004 A1 | 6/2016 | Hull et al. |
| 2016/0213282 A1 | 7/2016 | Leo et al. |
| 2016/0220307 A1 | 8/2016 | Miller et al. |
| 2016/0235470 A1 | 8/2016 | Callas et al. |
| 2016/0287314 A1 | 10/2016 | Arena et al. |
| 2016/0310211 A1 | 10/2016 | Long |
| 2016/0324564 A1 | 11/2016 | Gerlach et al. |
| 2016/0324573 A1 | 11/2016 | Mickelsen et al. |
| 2016/0331441 A1 | 11/2016 | Konings |
| 2016/0331459 A1 | 11/2016 | Townley et al. |
| 2016/0354142 A1 | 12/2016 | Pearson et al. |
| 2016/0361109 A1 | 12/2016 | Weaver et al. |
| 2017/0001016 A1 | 1/2017 | De Ridder |
| 2017/0035499 A1 | 2/2017 | Stewart et al. |

(56) References Cited

U.S. PATENT DOCUMENTS

| | | |
|---|---|---|
| 2017/0042449 A1 | 2/2017 | Deno et al. |
| 2017/0042615 A1 | 2/2017 | Salahieh et al. |
| 2017/0056648 A1 | 3/2017 | Syed et al. |
| 2017/0065330 A1 | 3/2017 | Mickelsen et al. |
| 2017/0065339 A1 | 3/2017 | Mickelsen |
| 2017/0065340 A1 | 3/2017 | Long |
| 2017/0065343 A1 | 3/2017 | Mickelsen |
| 2017/0071543 A1 | 3/2017 | Basu et al. |
| 2017/0095291 A1 | 4/2017 | Harrington et al. |
| 2017/0105793 A1 | 4/2017 | Cao et al. |
| 2017/0146584 A1 | 5/2017 | Daw et al. |
| 2017/0151029 A1 | 6/2017 | Mickelsen |
| 2017/0172654 A1 | 6/2017 | Wittkampf et al. |
| 2017/0181795 A1 | 6/2017 | Debruyne |
| 2017/0189097 A1 | 7/2017 | Viswanathan et al. |
| 2017/0215953 A1 | 8/2017 | Long et al. |
| 2017/0245928 A1 | 8/2017 | Xiao et al. |
| 2017/0246455 A1 | 8/2017 | Athos et al. |
| 2017/0312024 A1 | 11/2017 | Harlev et al. |
| 2017/0312025 A1 | 11/2017 | Harlev et al. |
| 2017/0312027 A1 | 11/2017 | Harlev et al. |
| 2018/0001056 A1 | 1/2018 | Leeflang et al. |
| 2018/0001085 A1* | 1/2018 | Cadossi ............... A61B 90/98 |
| 2018/0042674 A1 | 2/2018 | Mickelsen |
| 2018/0042675 A1 | 2/2018 | Long |
| 2018/0043153 A1 | 2/2018 | Viswanathan et al. |
| 2018/0064488 A1 | 3/2018 | Long et al. |
| 2018/0085160 A1 | 3/2018 | Viswanathan et al. |
| 2018/0093088 A1 | 4/2018 | Mickelsen |
| 2018/0133460 A1 | 5/2018 | Townley et al. |
| 2018/0154142 A1* | 6/2018 | Guo .................. A61B 18/1206 |
| 2018/0168511 A1 | 6/2018 | Hall et al. |
| 2018/0184982 A1 | 7/2018 | Basu et al. |
| 2018/0193090 A1 | 7/2018 | de la Rama et al. |
| 2018/0200497 A1 | 7/2018 | Mickelsen |
| 2018/0303488 A1 | 10/2018 | Hill |
| 2018/0311497 A1 | 11/2018 | Viswanathan et al. |
| 2018/0344393 A1 | 12/2018 | Gruba et al. |
| 2018/0360534 A1 | 12/2018 | Teplitsky et al. |
| 2019/0069950 A1 | 3/2019 | Viswanathan et al. |
| 2019/0151015 A1 | 5/2019 | Viswanathan et al. |
| 2019/0183378 A1 | 6/2019 | Mosesov et al. |
| 2019/0231421 A1 | 8/2019 | Viswanathan et al. |
| 2019/0269912 A1 | 9/2019 | Viswanathan et al. |
| 2019/0336198 A1 | 11/2019 | Viswanathan et al. |
| 2019/0336207 A1 | 11/2019 | Viswanathan |
| 2020/0397498 A1 | 12/2020 | Mickelsen et al. |
| 2021/0031020 A1 | 2/2021 | Mickelsen |
| 2021/0052325 A1 | 2/2021 | Viswanathan et al. |
| 2021/0077188 A1 | 3/2021 | Long et al. |

FOREIGN PATENT DOCUMENTS

| | | |
|---|---|---|
| EP | 0797956 | 6/2003 |
| EP | 1127552 | 6/2006 |
| EP | 1340469 | 3/2007 |
| EP | 1009303 | 6/2009 |
| EP | 2213729 | 8/2010 |
| EP | 2425871 | 3/2012 |
| EP | 1803411 | 8/2012 |
| EP | 2532320 A2 | 12/2012 |
| EP | 2587275 | 5/2013 |
| EP | 2663227 | 11/2013 |
| EP | 1909678 | 1/2014 |
| EP | 2217165 | 3/2014 |
| EP | 2376193 | 3/2014 |
| EP | 2708181 | 3/2014 |
| EP | 2777579 A1 | 9/2014 |
| EP | 2934307 | 10/2015 |
| EP | 2777585 | 6/2016 |
| EP | 2382935 B1 | 3/2018 |
| EP | 3111871 B1 | 3/2018 |
| EP | 3151773 B1 | 4/2018 |
| EP | 3056242 B1 | 7/2018 |
| JP | H06-507797 | 9/1994 |
| JP | H10-510745 | 10/1998 |
| JP | 2000-508196 | 7/2000 |
| JP | 2005-516666 | 6/2005 |
| JP | 2006-506184 | 2/2006 |
| JP | 2007-325935 | 12/2007 |
| JP | 2008-538997 | 11/2008 |
| JP | 2009-500129 | 1/2009 |
| JP | 2011-509158 | 3/2011 |
| JP | 2012-050538 | 3/2012 |
| WO | WO 92/07622 | 5/1992 |
| WO | WO 92/21278 | 12/1992 |
| WO | WO 92/21285 | 12/1992 |
| WO | WO 94/07413 | 4/1994 |
| WO | WO 97/24073 | 7/1997 |
| WO | WO 97/25917 | 7/1997 |
| WO | WO 97/37719 | 10/1997 |
| WO | WO 1999/004851 | 2/1999 |
| WO | WO 1999/022659 | 5/1999 |
| WO | WO 1999/056650 | 11/1999 |
| WO | WO 1999/059486 | 11/1999 |
| WO | WO 2002/056782 | 7/2002 |
| WO | WO 2003/053289 | 7/2003 |
| WO | WO 2003/065916 | 8/2003 |
| WO | WO 2004/045442 | 6/2004 |
| WO | WO 2004/086994 | 10/2004 |
| WO | WO 2005/046487 | 5/2005 |
| WO | WO 2006/115902 | 11/2006 |
| WO | WO 2007/006055 | 1/2007 |
| WO | WO 2007/079438 | 7/2007 |
| WO | WO 2009/082710 | 7/2009 |
| WO | WO 2009/089343 | 7/2009 |
| WO | WO 2009/137800 | 11/2009 |
| WO | WO 2010/014480 | 2/2010 |
| WO | WO 2011/028310 | 3/2011 |
| WO | WO 2011/154805 | 12/2011 |
| WO | WO 2012/051433 | 4/2012 |
| WO | WO 2012/153928 | 11/2012 |
| WO | WO 2013/019385 | 2/2013 |
| WO | WO 2014/008489 | 1/2014 |
| WO | WO 2014/025394 | 2/2014 |
| WO | WO 2014/031800 | 2/2014 |
| WO | WO 2014/036439 | 3/2014 |
| WO | WO 2014/160832 | 10/2014 |
| WO | WO 2015/066322 | 5/2015 |
| WO | WO 2015/099786 | 7/2015 |
| WO | WO 2015/103530 | 7/2015 |
| WO | WO 2015/103574 | 7/2015 |
| WO | WO 2015/130824 | 9/2015 |
| WO | WO 2015/140741 | 9/2015 |
| WO | WO 2015/143327 | 9/2015 |
| WO | WO 2015/171921 | 11/2015 |
| WO | WO 2015/175944 | 11/2015 |
| WO | WO 2015/192018 | 12/2015 |
| WO | WO 2015/192027 | 12/2015 |
| WO | WO 2016/059027 | 4/2016 |
| WO | WO 2016/060983 | 4/2016 |
| WO | WO 2016/081650 | 5/2016 |
| WO | WO 2016/090175 | 6/2016 |
| WO | WO 2017/093926 | 6/2017 |
| WO | WO 2017/119934 | 7/2017 |
| WO | WO 2017/120169 | 7/2017 |
| WO | WO 2017/192477 | 11/2017 |
| WO | WO 2017/192495 | 11/2017 |
| WO | WO 2017/218734 | 12/2017 |
| WO | WO 2018/005511 | 1/2018 |
| WO | WO 2018/200800 | 11/2018 |
| WO | WO 2019/133606 | 7/2019 |

OTHER PUBLICATIONS

Partial Supplementary European Search Report for European Application No. 13827672.0, mailed Mar. 23, 2016, 6 pages.

Supplementary European Search Report for European Application No. 13827672.0, mailed Jul. 11, 2016, 12 pages.

Office Action for European Application No. 13827672.0, mailed Feb. 5, 2018, 6 pages.

Notice of Reasons for Rejection for Japanese Application No. 2015-526522, mailed Mar. 6, 2017, 3 pages.

(56) References Cited

OTHER PUBLICATIONS

Office Action for U.S. Appl. No. 14/400,455, mailed Mar. 30, 2017, 10 pages.
International Search Report and Written Opinion for International Application No. PCT/US2013/031252, mailed Jul. 19, 2013, 12 pages.
Extended European Search Report for European Application No. 19182099.2, mailed Dec. 13, 2019, 7 pages.
Office Action for Japanese Application No. 2018-036714, dated Jan. 16, 2019, 8 pages.
Office Action for Japanese Application No. 2018-036714, dated Nov. 27, 2019, 5 pages.
Office Action for U.S. Appl. No. 15/819,726, mailed Jun. 4, 2018, 17 pages.
Office Action for U.S. Appl. No. 15/917,194, mailed Jun. 4, 2018, 17 pages.
Office Action for U.S. Appl. No. 15/917,194, mailed Oct. 9, 2018, 13 pages.
Office Action for U.S. Appl. No. 15/917,194, mailed Apr. 29, 2019, 10 pages.
Office Action for U.S. Appl. No. 15/917,194, mailed Dec. 20, 2019, 10 pages.
First Office Action for Chinese Application No. 201580006848.8, dated Jan. 29, 2018, 15 pages.
Office Action for European Application No. 15701856.5, mailed Dec. 11, 2017, 6 pages.
Notice of Reasons for Rejection for Japanese Application No. 2016-544072, mailed Oct. 1, 2018, 11 pages.
Office Action for U.S. Appl. No. 15/201,983, mailed Apr. 3, 2019, 16 pages.
Office Action for U.S. Appl. No. 15/201,983, mailed Nov. 15, 2019, 15 pages.
International Search Report and Written Opinion for International Application No. PCT/US2015/010138, mailed Mar. 26, 2015, 14 pages.
International Preliminary Report on Patentability for International Application No. PCT/US2015/010138, dated Jul. 12, 2016, 9 pages.
Supplementary European Search Report for European Application No. 15733297.4, mailed Aug. 10, 2017, 7 pages.
Office Action for U.S. Appl. No. 15/201,997, mailed Apr. 3, 2017, 6 pages.
Office Action for U.S. Appl. No. 15/201,997, mailed Aug. 29, 2017, 12 pages.
Office Action for U.S. Appl. No. 15/201,997, mailed Jul. 12, 2018, 12 pages.
Office Action for U.S. Appl. No. 15/201,997, mailed Dec. 17, 2018, 17 pages.
International Search Report and Written Opinion for International Application No. PCT/US2015/010223, mailed Apr. 10, 2015, 19 pages.
International Preliminary Report on Patentability for International Application No. PCT/US2015/010223, dated Jul. 12, 2016, 12 pages.
Office Action for U.S. Appl. No. 15/341,512, mailed Aug. 1, 2019, 19 pages.
Office Action for U.S. Appl. No. 15/341,512, mailed Nov. 12, 2019, 18 pages.
International Search Report and Written Opinion for International Application No. PCT/US2015/029734, mailed Nov. 24, 2015, 15 pages.
Extended European Search Report for European Application No. 18189811.5, mailed May 14, 2019, 7 pages.
Office Action for U.S. Appl. No. 15/795,062, mailed Dec. 19, 2017, 14 pages.
Office Action for U.S. Appl. No. 15/795,062, mailed Apr. 9, 2018, 20 pages.
Office Action for U.S. Appl. No. 15/795,062, mailed May 3, 2019, 21 pages.
Office Action for U.S. Appl. No. 15/795,062, mailed Nov. 4, 2019, 23 pages.
Office Action for U.S. Appl. No. 15/341,523, mailed Jan. 29, 2019, 10 pages.
Office Action for U.S. Appl. No. 15/341,523, mailed Jul. 30, 2019, 8 pages.
International Search Report and Written Opinion for International Application No. PCT/US2015/031086, mailed Oct. 21, 2015, 16 pages.
Office Action for U.S. Appl. No. 15/795,075, mailed Feb. 6, 2018, 9 pages.
Office Action for U.S. Appl. No. 15/795,075, mailed Jun. 15, 2018, 10 pages.
Office Action for U.S. Appl. No. 15/795,075, mailed Apr. 10, 2019, 11 pages.
Office Action for U.S. Appl. No. 15/795,075, mailed Jul. 31, 2019, 12 pages.
Extended European Search Report for European Application No. 15849844.4, mailed May 3, 2018, 8 pages.
Office Action for U.S. Appl. No. 15/484,969, mailed Sep. 4, 2019, 12 pages.
Office Action for U.S. Appl. No. 15/484,969, mailed Jul. 16, 2020, 12 pages.
International Search Report and Written Opinion for International Application No. PCT/US2015/055105, mailed Mar. 1, 2016, 15 pages.
Office Action for U.S. Appl. No. 15/796,255, mailed Jan. 10, 2018, 12 pages.
Extended European Search Report for European Application No. 15806855.1, mailed Jan. 3, 2018, 8 pages.
Office Action for U.S. Appl. No. 15/354,475, mailed May 23, 2019, 7 pages.
International Search Report and Written Opinion for International Application No. PCT/US2015/035582, mailed Oct. 2, 2015, 17 pages.
Extended European Search Report for European Application No. 15806278.6, mailed Feb. 9, 2018, 5 pages.
International Search Report and Written Opinion for International Application No. PCT/US2015/035592, mailed Oct. 2, 2015, 13 pages.
Extended European Search Report for European Application No. 16884132.8, mailed Jul. 8, 2019, 7 pages.
Office Action for U.S. Appl. No. 15/334,646, mailed Jul. 25, 2017, 19 pages.
Office Action for U.S. Appl. No. 15/334,646, mailed Nov. 16, 2017, 26 pages.
International Search Report and Written Opinion for International Application No. PCT/US2016/057664, mailed Feb. 24, 2017, 11 pages.
Office Action for U.S. Appl. No. 15/796,375, mailed Jan. 24, 2018, 25 pages.
Office Action for U.S. Appl. No. 15/796,375, mailed May 30, 2018, 26 pages.
Office Action for U.S. Appl. No. 15/796,375, mailed Nov. 16, 2018, 27 pages.
Office Action for U.S. Appl. No. 16/416,677, mailed Aug. 15, 2019, 8 pages.
Extended European Search Report for European Application No. 17736218.3 mailed Aug. 23, 2019, 9 pages.
International Search Report and Written Opinion for International Application No. PCT/US2017/012099, mailed May 18, 2017, 17 pages.
Office Action for U.S. Appl. No. 15/711,266, mailed Feb. 23, 2018, 14 pages.
International Search Report and Written Opinion for International Application No. PCT/US2018/029938, mailed Aug. 29, 2018, 14 pages.
Office Action for U.S. Appl. No. 16/181,027, mailed Sep. 4, 2019, 12 pages.
International Search Report and Written Opinion for International Application No. PCT/US2019/014226, mailed Apr. 29, 2019, 15 pages.
Office Action for U.S. Appl. No. 16/240,066, mailed May 29, 2019, 7 pages.

(56) References Cited

OTHER PUBLICATIONS

Office Action for U.S. Appl. No. 16/375,561, mailed Oct. 17, 2019, 15 pages.
International Search Report and Written Opinion for International Application No. PCT/US2017/037609, mailed Nov. 8, 2017, 13 pages.
Office Action for U.S. Appl. No. 15/672,916, mailed Feb. 13, 2018, 16 pages.
Office Action for U.S. Appl. No. 15/672,916, mailed Jul. 20, 2018, 23 pages.
Office Action for U.S. Appl. No. 15/672,916, mailed Apr. 9, 2019, 31 pages.
Office Action for U.S. Appl. No. 15/499,804, mailed Jan. 3, 2018, 20 pages.
Office Action for U.S. Appl. No. 15/794,717, mailed Feb. 1, 2018, 10 pages.
International Search Report and Written Opinion for International Application No. PCT/US2018/029552, mailed Jun. 29, 2018, 13 pages.
Partial European Search Report for European Application No. 18170210.1, mailed Feb. 14, 2019, 13 pages.
Extended European Search Report for European Application No. 18170210.1, mailed May 17, 2019, 11 pages.
International Search Report and Written Opinion for International Application No. PCT/US2018/050660, mailed Nov. 26, 2018, 13 pages.
Office Action for U.S. Appl. No. 15/970,404, mailed Oct. 9, 2018, 21 pages.
Office Action for U.S. Appl. No. 15/970,404, mailed Apr. 12, 2019, 20 pages.
Office Action for U.S. Appl. No. 15/970,404, mailed Nov. 12, 2019, 19 pages.
International Search Report and Written Opinion for International Application No. PCT/US2019/028943, mailed Sep. 17, 2019, 17 pages.
International Search Report and Written Opinion for International Application No. PCT/US2019/017322, mailed May 10, 2019, 15 pages.
International Search Report and Written Opinion for International Application No. PCT/US2019/030922, mailed Sep. 6, 2019, 12 pages.
International Search Report and Written Opinion for International Application No. PCT/US2019/030882, mailed Sep. 10, 2019, 17 pages.
Office Action for U.S. Appl. No. 16/573,704, mailed Dec. 17, 2019, 6 pages.
Office Action for U.S. Appl. No. 16/405,515, mailed Sep. 6, 2019, 9 pages.
International Search Report and Written Opinion for International Application No. PCT/US2019/031135, mailed Aug. 5, 2019, 11 pages.
Du Pre, B.C. et al., "Minimal coronary artery damage by myocardial electroporation ablation," Europace, 15(1):144-149 (2013).
Hobbs, E. P., "Investor Relations Update: Tissue Ablation via Irreversible Electroporation (IRE)," Powerpoint (2004), 16 pages.
Lavee, J. et al., "A Novel Nonthermal Energy Source for Surgical Epicardial Atrial Ablation: Irreversible Electroporation," The Heart Surgery Forum #2006-1202, 10(2), 2007 [Epub Mar. 2007].
Madhavan, M. et al., "Novel Percutaneous Epicardial Autonomic Modulation in the Canine for Atrial Fibrillation: Results of an Efficacy and Safety Study," Pace, 00:1-11 (2016).
Neven, K. et al., "Safety and Feasibility of Closed Chest Epicardial Catheter Ablation Using Electroporation," Circ Arrhythm Electrophysiol., 7:913-919 (2014).
Neven, K. et al., "Myocardial Lesion Size After Epicardial Electroporation Catheter Ablation After Subxiphoid Puncture," Circ Arrhythm Electrophysiol., 7(4):728-733 (2014).
Neven, K. et al., "Epicardial linear electroporation ablation and lesion size," Heart Rhythm, 11:1465-1470 (2014).
Van Driel, V.J.H.M. et al., "Pulmonary Vein Stenosis After Catheter Ablation Electroporation Versus Radiofrequency," Circ Arrhythm Electrophysiol., 7(4):734-738 (2014).
Van Driel, V.J.H.M. et al., "Low vulnerability of the right phrenic nerve to electroporation ablation," Heart Rhythm, 12:1838-1844 (2015).
Wittkampf, F.H. et al., "Myocardial Lesion Depth With Circular Electroporation Ablation," Circ. Arrhythm Electrophysiol., 5(3):581-586 (2012).
Wittkampf, F.H. et al., "Feasibility of Electroporation for the Creation of Pulmonary Vein Ostial Lesions," J Cardiovasc Electrophysiol, 22(3):302-309 (Mar. 2011).
Office Action for European Application No. 15806855.1, mailed Jun. 4, 2021, 7 pages.

* cited by examiner

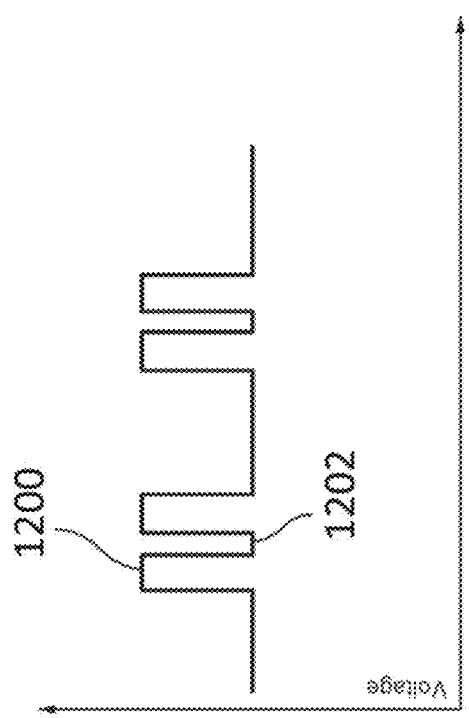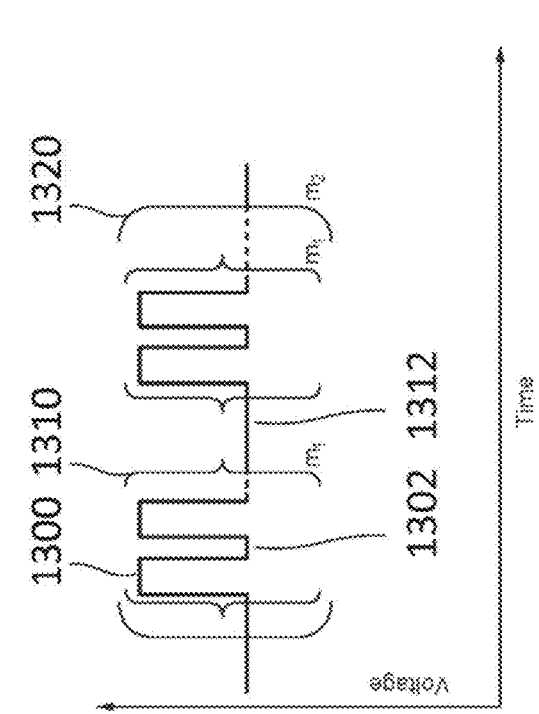

SYSTEMS, DEVICES, AND METHODS FOR ABLATION USING SURGICAL CLAMPS

CROSS-REFERENCE TO RELATED APPLICATIONS

This application is a continuation of International Application No. PCT/US2019/028943, filed on Apr. 24, 2019, which claims the benefit of and is a continuation of U.S. application Ser. No. 15/970,404, filed on May 3, 2018, now abandoned, the entire disclosure of each of which is incorporated herein by reference in its entirety.

TECHNICAL FIELD

The embodiments described herein relate generally to medical devices for therapeutic electrical energy delivery, and more particularly to a surgical clamp device for delivering electrical energy to ablate tissue.

BACKGROUND

In the past two decades, the technique of electroporation has advanced from the laboratory to clinical applications, while the effects of brief pulses of high voltages and large electric fields on tissue has been investigated for the past forty years or more. Application of brief, high DC voltages to tissue, thereby generating locally high electric fields typically in the range of hundreds of Volts/centimeter, can disrupt cell membranes by generating pores in the cell membrane. While the precise mechanism of this electrically-driven pore generation (or electroporation) is not well understood, it is thought that the application of relatively large electric fields generates instabilities in the lipid bilayers in cell membranes, causing the occurrence of a distribution of local gaps or pores in the membrane. If the applied electric field at the membrane is larger than a threshold value, the electroporation is irreversible and the pores remain open, permitting exchange of material across the membrane and leading to necrosis and/or apoptosis (cell death). Subsequently the tissue heals in a natural process. While pulsed DC voltages are known to drive electroporation under the right circumstances, known approaches do not provide for ease of navigation, placement and therapy delivery from one or more devices and for safe energy delivery, especially in the context of ablation therapy for cardiac arrhythmias with epicardial catheter devices.

Thus, there is a need for devices that can effectively deliver electroporation ablation therapy selectively to tissue in regions of interest while minimizing damage to healthy tissue. In particular, there is a need for devices that can efficiently deliver electroporation therapy to desired tissue regions while at the same time minimizing the occurrence of irreversible electroporation in undesired tissue regions.

SUMMARY

Described here are systems, devices, and methods for ablating tissue through irreversible electroporation. Such electroporation delivery systems, devices, and methods can enhance safety of energy delivery and broaden the areas of clinical application of electroporation including therapeutic treatment of a variety of cardiac arrhythmias. In some embodiments, an apparatus may include a first jaw including a plurality of first electrodes. A second jaw may include a plurality of second electrodes. The first jaw and the second jaw may be substantially rigid, elongate, and may collectively define a longitudinal axis. The first jaw and the second jaw may be further configured to engage tissue therebetween during use. Each electrode of the plurality of first electrodes may have a width orthogonal to the longitudinal axis that is less than a length of that electrode measured parallel to the longitudinal axis. The plurality of first electrodes may be spaced apart laterally with respect to the longitudinal axis. Each electrode of the plurality of second electrodes may have a width orthogonal to the longitudinal axis that is less than a length of that electrode measured parallel to the longitudinal axis. The plurality of second electrodes may be spaced apart laterally with respect to the longitudinal axis. Each electrode of the plurality of first electrodes and the plurality of second electrodes may be configured to deliver a pulse waveform of at least about 200 Volts.

In some embodiments, an apparatus includes a first jaw including a plurality of first electrodes; and a second jaw including a plurality of second electrodes, the first jaw and the second jaw being substantially rigid, elongate, and collectively defining a longitudinal axis, the first jaw and the second jaw further configured to engage tissue therebetween during use. Each electrode of the plurality of first electrodes can have, within a cross-section of the first jaw and the second jaw that is orthogonal to the longitudinal axis, a width that is less than a length of that electrode, the plurality of first electrodes spaced apart laterally with respect to the longitudinal axis. Each electrode of the plurality of second electrodes can have, within the cross-section orthogonal to the longitudinal axis, a width that is less than a length of that electrode, the plurality of second electrodes spaced apart laterally with respect to the longitudinal axis. The plurality of first electrodes and the plurality of second electrodes can include electrode pairs or sets of electrodes configured to deliver ablative energy to the tissue in response to receiving a pulse waveform having an amplitude of at least about 200 Volts, at least one electrode pair or set of electrodes including an electrode of the plurality of first electrodes and an electrode of the plurality of second electrodes disposed diagonally across from one another within the cross-section orthogonal to the longitudinal axis.

In some embodiments, each electrode of the plurality of first electrodes and the plurality of second electrodes may be independently addressable. In some embodiments, the longitudinal axis has one or more of a straight portion and curved portion. In some embodiments, an electrode of the plurality of first electrodes may be configured as an anode and an electrode from the plurality of second electrodes may be configured as a cathode, the anode being disposed directly across from the cathode. In some embodiments, an electrode from the plurality of first electrodes may be configured as an anode and another electrode from the plurality of first electrodes is configured as a cathode. The anode may be spaced apart laterally from the cathode. In some embodiments, at least two of the plurality of first electrodes may be spaced apart by a first measure. The first jaw and the second jaw may be spaced apart by a second measure, e.g., when engaged with tissue therebetween during use. A ratio of the second measure to the first measure may be between about 0.1:1 and about 12:1. In some embodiments, a distance between a midpoint of at least two of the plurality of first electrodes in a cross-section orthogonal to the longitudinal axis may be between about 1 mm and about 10 mm.

In some embodiments, any two adjacent electrodes of the plurality of first electrodes may be spaced apart by a first measure of between about 0.5 mm and about 10 mm and any two adjacent electrodes of the plurality of second electrodes may be spaced apart by a second measure of between about 0.5 mm and about 10 mm. In some embodiments, any two adjacent electrodes of the plurality of first electrodes may be spaced apart by a first measure and any two adjacent electrodes of the plurality of second electrodes are spaced apart by a second measure. A ratio of the first measure to the second measure may be between about 0.05:1 and about 20:1.

In some embodiments, any two adjacent electrodes of the plurality of first electrodes may be spaced apart by a first measure and any two adjacent electrodes of the plurality of second electrodes may be spaced apart by a second measure. A ratio of the width of any electrode of the plurality of first electrodes to the width of any electrode of the plurality of second electrodes to the first measure may be between about 0.01:1 and about 10:1. In some embodiments, each electrode of the plurality of first electrodes and the plurality of second electrodes may have a length of between about 10 mm and about 120 mm.

In some embodiments, the first and second jaws may be configured to transition between a first configuration for positioning the first and second jaws through or around a body cavity, organ system, or anatomical structure and a second configuration for engaging the tissue. In some embodiments, the first and second jaws may be spaced apart by a spacing distance in the second configuration. In some embodiments, the cross-section (or cross-sectional shape) of each electrode of the plurality of first electrodes and the plurality of second electrodes may be substantially rectangular. In some embodiments, each electrode of the plurality of first electrodes and the plurality of second electrodes may include a curved portion. In some of these embodiments, the curved portion may have a radius of curvature of about 1 cm or larger. In some embodiments, the curved portion may have a J shape.

In some embodiments, each electrode of the plurality of first electrodes and the plurality of second electrodes may include an exposed portion in electrical contact with the tissue during use. In some of these embodiments, the exposed portion of each electrode of the plurality of first electrodes and the plurality of second electrodes may be flat or convex. In some embodiments, the first and second jaws may be parallel, e.g., extend in parallel to one another. In some embodiments, a pulse generator may include a generator. The generator may be coupled to each electrode of the plurality of first electrodes and the plurality of second electrodes. The controller may include a processor and memory. The generator may be configured to generate a pulse waveform of at least about 200 Volts. A first set of electrodes of the plurality of first electrodes and the plurality of second electrodes may be configured for pulse waveform delivery. In some embodiments, the pulse waveform may be delivered to the first set of electrodes. In some of these embodiments, the generator may be further configured to configure a second set of electrodes of the plurality of first electrodes and the plurality of second electrodes for receiving electrical activity of tissue, and receive signal data corresponding to electrical activity of the tissue using the second set of electrodes. Electrocardiography data may be generated using the signal data.

In some embodiments, a handle may be coupled to the first jaw and the second jaw. In some of these embodiments, the handle may include one or more of a jaw control, electrode selection control, and pulse waveform control. In some embodiments, a pivot may couple the first jaw to the second jaw. In some embodiments, a spring may be configured to bias the first and second jaws closed. In some embodiments, one or more lead wires may be coupled to the plurality of first electrodes and the plurality of second electrodes.

In some embodiments, an apparatus may include a first jaw including a first electrode and a second electrode. A second jaw may include a third electrode and a fourth electrode. The first jaw and the second jaw may be substantially rigid, elongate, and collectively define a longitudinal axis. The first jaw and the second jaw may be further configured to engage tissue therebetween during use. The first electrode may be disposed directly across the third electrode. The second electrode may be disposed directly across the fourth electrode. A processor may be operably coupled to the first jaw and the second jaw. The processor may be configured to, during use, configure the first electrode as an anode and the third electrode as a cathode. Pulsed electric field ablative energy may be delivered via the first electrode and the third electrode.

In some embodiments, each of the first electrode, second electrode, third electrode, and fourth electrode are independently addressable. In some embodiments, the longitudinal axis may have one or more of a straight portion and a curved portion. In some embodiments, the first electrode and the second electrode may be spaced apart by a first measure of between about 0.5 mm and about 10 mm, and the third electrode and the fourth electrode may be spaced apart by a second measure of between about 0.5 mm and about 10 mm. In some embodiments, the first electrode and the second electrode may be spaced apart by a first measure and the third electrode and the fourth electrode may be spaced apart by a second measure. A ratio of the first measure to the second measure may be between about 0.05:1 and about 20:1. In some embodiments, the first electrode and the second electrode may be spaced apart by a first measure. A ratio of a width of the first electrode to the first measure may be between about 0.01:1 and about 10:1. In some embodiments, the first, second, third, and fourth electrode may each have a length of between about 10 mm and about 120 mm.

In some embodiments, the first and second jaws may be configured to transition between a first configuration for positioning the first and second jaws through or around a body cavity, organ system, or anatomical structure and a second configuration for engaging the tissue. In some of these embodiments, the first and second jaws may be spaced apart by a spacing distance in the second configuration. In some embodiments, the cross-section of the first, second, third, and fourth electrodes may be substantially rectangular. In some embodiments, the first, second, third, and fourth electrodes may include a curved portion.

In some of these embodiments, the curved portion may have a radius of curvature of about 1 cm or larger. In some of these embodiments, the curved portion may have a J shape. In some embodiments, the first, second, third, and fourth electrodes may include an exposed portion in electrical contact with the tissue during use. In some of these embodiments, the exposed portion of each of the electrodes may be flat or convex. In some embodiments, the first and second jaws may be parallel.

In some embodiments, a pulse generator may include a controller. The pulse generator may be coupled to the first, second, third, and fourth electrodes. The controller may include a processor and memory. The generator may be configured to generate a pulse waveform of at least about 200 Volts. A first set of electrodes of the first, second, third, and fourth electrodes may be configured for pulse waveform delivery. The pulse waveform may be delivered to the first set of electrodes.

In some embodiments, the generator may be further configured to configure a second set of electrodes of the first, second, third, and fourth electrodes for receiving electrical activity of tissue. Signal data may be received corresponding to electrical activity of the tissue using the second set of electrodes. Electrocardiography data may be generated using the signal data.

In some embodiments, a handle may be coupled to the first jaw and the second jaw. In some of these embodiments, the handle may include one or more of a jaw control, electrode selection control, and pulse waveform control. In some embodiments, a pivot may couple the first jaw to the second jaw. In some embodiments, a spring may be configured to bias the first and second jaws closed. In some embodiments, one or more lead wires may be coupled to the first, second, third, and fourth electrodes.

In some embodiments, a method of ablating tissue via irreversible electroporation may include the steps of clamping tissue between a first jaw and a second jaw of an apparatus. The first jaw may include a plurality of first electrodes and the second jaw may include a plurality of second electrodes. The first jaw and the second jaw may be substantially rigid, elongate, and may collectively define a longitudinal axis. Each electrode of the plurality of first electrodes may have a width orthogonal to the longitudinal axis that is less than a length parallel to the longitudinal axis of that electrode. The plurality of first electrodes may be spaced apart laterally with respect to the longitudinal axis. Each electrode of the plurality of second electrodes may have a width orthogonal to the longitudinal axis that is less than a length parallel to the longitudinal axis of that electrode. The plurality of second electrodes may be spaced apart laterally with respect to the longitudinal axis. An electrode of the plurality of first electrodes may be configured as an anode. An electrode of the plurality of second electrodes may be configured as a cathode. The anode and the cathode may be disposed diagonally across the longitudinal axis and may be spaced apart laterally with respect to the longitudinal axis. Ablative energy may be delivered to the tissue via the anode and the cathode.

In some embodiments, the longitudinal axis may have one or more of a straight portion and curved portion. In some embodiments, clamping the tissue may include transitioning the first and second jaws between a first configuration for advancing the apparatus and a second configuration for clamping the tissue. In some embodiments, the tissue may be a region of the atrial base of a pulmonary vein. In some embodiments, the pulse waveform may include a first level of a hierarchy of the pulsed waveform includes a first set of pulses, each pulse having a pulse time duration, and a first time interval separating successive pulses. A second level of the hierarchy of the pulsed waveform may include a plurality of first sets of pulses as a second set of pulses, a second time interval separating successive first sets of pulses, the second time interval being at least three times the duration of the first time interval. A third level of the hierarchy of the pulsed waveform may include a plurality of second sets of pulses as a third set of pulses, a third time interval separating successive second sets of pulses, the third time interval being at least thirty times the duration of the second level time interval.

In some embodiments, signal data may be received corresponding to electrical activity of the tissue using one or more of the plurality of first electrodes and the plurality of second electrodes. Electrocardiography data may be generated using the signal data. In some embodiments, the first and second jaws may be positioned through or around a body cavity, organ system, or anatomical structure. In some embodiments, each electrode of the plurality of first electrodes and the plurality of second electrodes may be independently addressable.

BRIEF DESCRIPTION OF THE DRAWINGS

FIG. 12 is an example waveform including a sequence of voltage pulses with a pulse width defined for each pulse, according to embodiments.

FIG. 13 schematically illustrates a hierarchy of pulses including pulse widths, intervals between pulses, and groupings of pulses, according to embodiments.

DETAILED DESCRIPTION

Figure 1A:
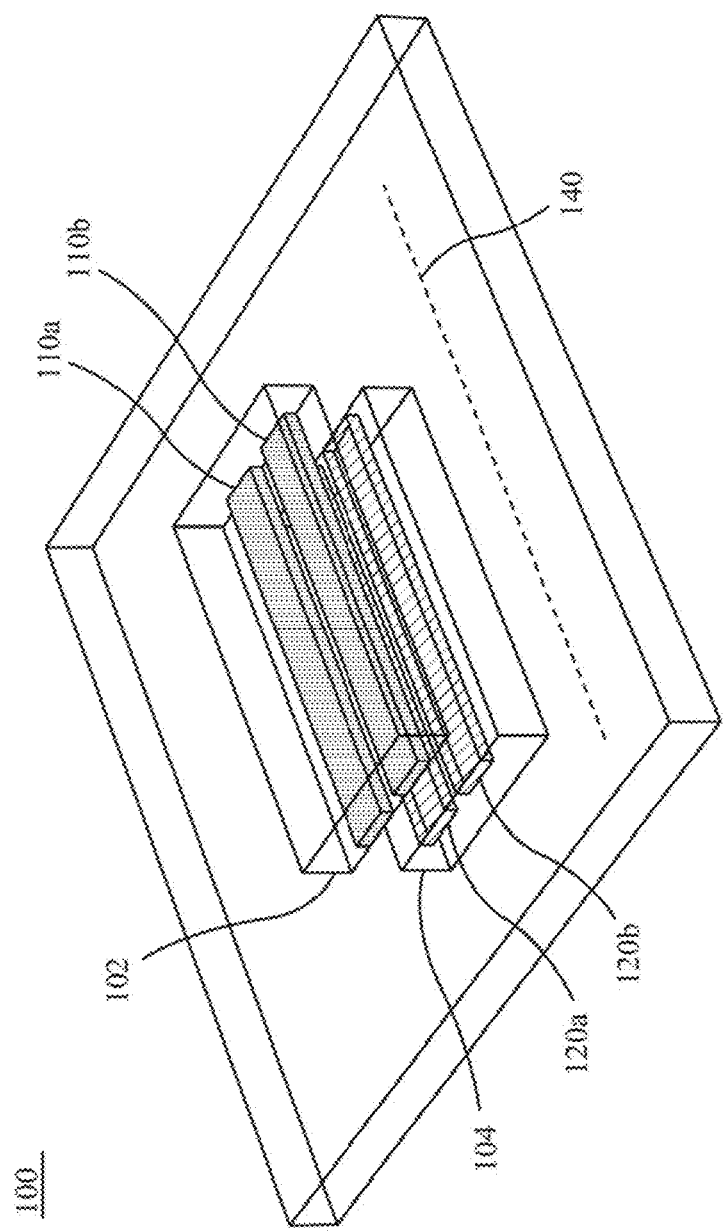
FIG. 1A is a schematic perspective view of an ablation device, according to embodiments.

Described herein are systems, devices, and methods for selective and rapid application of pulsed electric fields to ablate tissue by irreversible electroporation. Generally, the systems, devices, and methods described herein may be used to generate electric field magnitudes at desired regions of interest while tissue is clamped (e.g., held) in order to treat atrial fibrillation via irreversible electroporation. An ablation device may include a set of jaws or arms each having a set of electrodes that may be configured to hold (e.g., clamp, grasp, compress) a portion of tissue therebetween and provide tissue ablation with reduced energy delivery. The set of electrodes may be configured to contact tissue during use. The jaws may transition from a closed configuration to an open configuration for grasping tissue such as a pulmonary vein. It is understood that the set of jaws may be transformed into any intermediate configuration between the open and closed configurations, continuously or in discrete steps. For example, the jaws may transition from a closed configuration to an open configuration to allow tissue to be placed between the jaws. Then, the jaws may be brought closer together to apply compression force to tissue disposed therebetween to target energy delivery to a desired portion of tissue.

An irreversible electroporation system as described herein may include a signal generator and a processor configured to apply one or more voltage pulse waveforms to a selected set of electrodes of an ablation device (e.g., clamp, clip, forcep, hemostat) to deliver energy to a region of interest (e.g., portion of a pulmonary vein) and provide a highly configurable a set of electrode channels (e.g., allow independent and arbitrary electrode selection). The ablation device may generally include a pair of opposable members configured to hold tissue therebetween. In some embodiments, the opposable members may be movable relative to each other. The pulse waveforms disclosed herein may aid in therapeutic treatment of a variety of cardiac arrhythmias (e.g., atrial fibrillation). In order to deliver the pulse waveforms generated by the signal generator, the ablation device may comprise one or more elongate parallel electrodes. In some embodiments, the electrodes may be independently addressable such that each electrode may be controlled (e.g., deliver energy) independently of any other electrode of the device. For example, an anode-cathode energy delivery sequence may be selected to ablate desired regions of tissue and/or to reduce the possibility of shorting. In this manner, the electrodes may deliver different energy waveforms with different timing synergistically for electroporation of tissue.

The term "electroporation" as used herein refers to the application of an electric field to a cell membrane to change the permeability of the cell membrane to the extracellular environment. The term "reversible electroporation" as used herein refers to the application of an electric field to a cell membrane to temporarily change the permeability of the cell membrane to the extracellular environment. For example, a cell undergoing reversible electroporation may observe the temporary and/or intermittent formation of one or more pores in its cell membrane that close up upon removal of the electric field. The term "irreversible electroporation" as used herein refers to the application of an electric field to a cell membrane to permanently change the permeability of the cell membrane to the extracellular environment. For example, a cell undergoing irreversible electroporation may observe the formation of one or more pores in its cell membrane that persist upon removal of the electric field.

Pulse waveforms for electroporation energy delivery as disclosed herein may enhance the safety, efficiency, and effectiveness of energy delivery to tissue by reducing the electric field threshold associated with irreversible electroporation, thus yielding more effective ablative lesions with a reduction in total energy delivered. In some embodiments, the voltage pulse waveforms disclosed herein may be hierarchical and have a nested structure. For example, the pulse waveform may include hierarchical groupings of pulses having associated timescales. In some embodiments, the methods, systems, and devices disclosed herein may comprise one or more of the methods, systems, and devices described in International Application Serial No. PCT/US2016/057664, filed on Oct. 19, 2016, and titled "SYSTEMS, APPARATUSES AND METHODS FOR DELIVERY OF ABLATIVE ENERGY TO TISSUE," and U.S. application Ser. No. 15/796,375, filed on Oct. 27, 2017, and titled "SYSTEMS, APPARATUSES AND METHODS FOR DELIVERY OF ABLATIVE ENERGY TO TISSUE," the contents of each of which are hereby incorporated by reference in their entirety.

In some embodiments, the systems may further include a cardiac stimulator used to synchronize the generation of the pulse waveform to a paced heartbeat. The cardiac stimulator may electrically pace the heart with a cardiac stimulator and ensure pacing capture to establish periodicity and predictability of the cardiac cycle. A time window within a refractory period of the periodic cardiac cycle may be selected for voltage pulse waveform delivery. Thus, voltage pulse waveforms may be delivered in the refractory period of the cardiac cycle to avoid disruption of the sinus rhythm of the heart. The ablation device may transform into different configurations (e.g., compact and expanded) to navigate and position the device within a body cavity. In some embodiments, the system may optionally include one or more return electrodes.

Generally, to ablate tissue, the device may be surgically placed at a target location. In a cardiac application, the electrodes through which the voltage pulse waveform is delivered may be disposed on opposing sides of a pair of jaws of an ablation device. The methods described here may include placing tissue (e.g., pulmonary vein) between the jaws in contact with the electrodes. A pulse waveform may be generated and delivered to one or more electrodes of the device to ablate tissue. In some embodiments, the pulse waveform may be generated in synchronization with a pacing signal of the heart to avoid disruption of the sinus rhythm of the heart. In some embodiments, the electrodes may be configured in anode-cathode (e.g., bipole) subsets. The pulse waveform may include hierarchical waveforms to aid in tissue ablation and reduce damage to healthy tissue.

I. Systems

Overview

Disclosed herein are systems and devices configured for tissue ablation via the selective and rapid application of voltage pulse waveforms to aid tissue ablation, resulting in irreversible electroporation. Generally, a system for ablating tissue described here may include a signal generator and an ablation device having one or more electrodes for the selective and rapid application of DC voltage to drive electroporation. Voltages may be applied to a selected subset of the electrodes, with independent subset selections for anode and cathode electrode selections. The ablation device may be coupled to one or more electrode channels of the signal generator. Each electrode channel may be independently configured as an anode or cathode and a voltage pulse waveform may be delivered through one or more of the electrode channels in a predetermined sequence. A pacing signal for cardiac stimulation may be generated and used to generate the pulse waveform by the signal generator in synchronization with the pacing signal.

Figure 7:
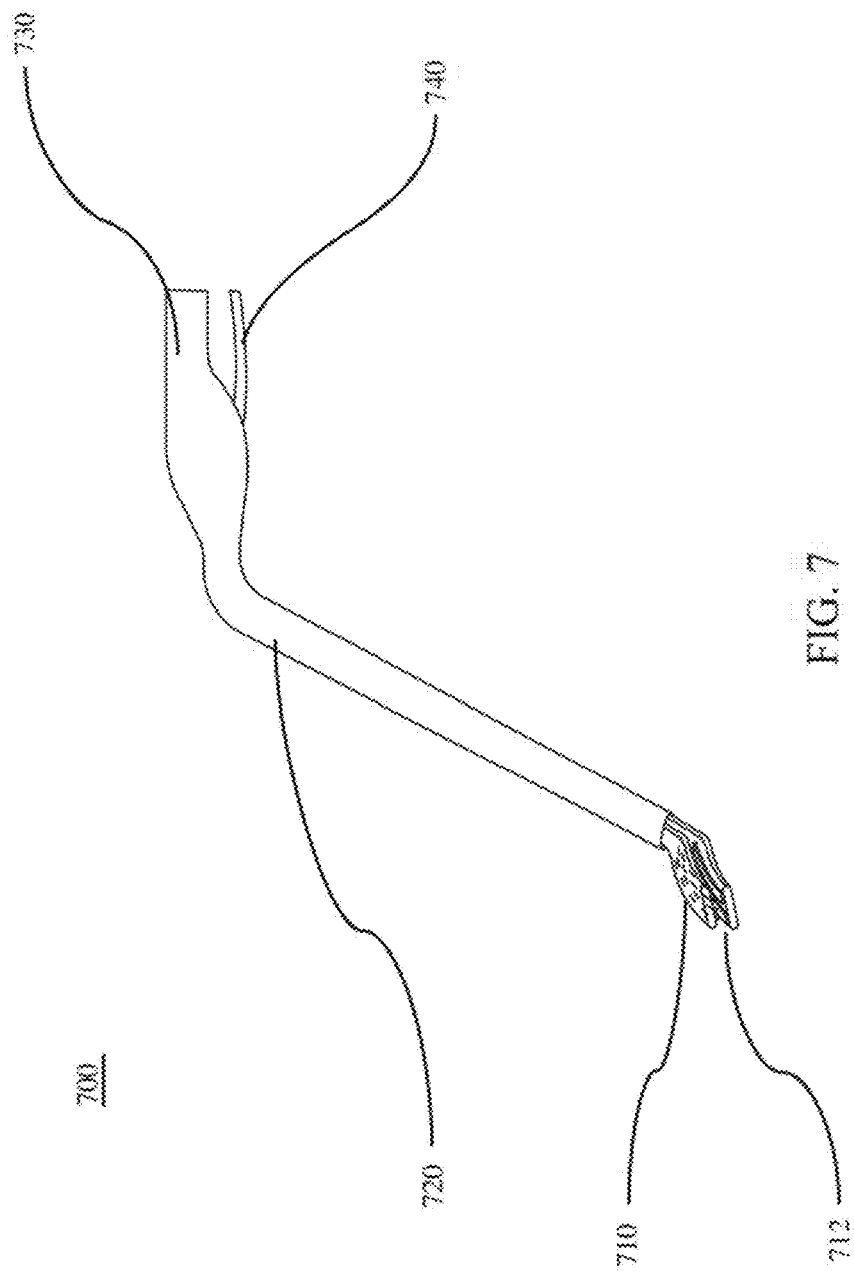
FIG. 7 is a side view of an ablation device, according to embodiments.

Generally, the systems and devices described herein include one or more ablation devices configured to ablate tissue held between jaws of the device. FIG. 7 is a side view of an ablation device (700) configured to hold tissue and deliver energy for tissue ablation. The ablation device (700) may include a first jaw (710) and a second jaw (712) coupled to a distal end of a body (e.g., shaft, elongate member) (720). A proximal end of the body (720) may be coupled to a handle (730). In some embodiments, the handle (730) may include an actuator (740) that may be configured to control one or more of the jaws (710, 720) and energy delivery, as described in more detail herein. In some embodiments, the actuator (740) may include an input device such as one or more of a lever, trigger, button, slide, switch, and the like. For example, a user may engage the actuator to transition and hold the jaws in an open configuration to permit the release of tissue held therebetween. When a desired portion of tissue is positioned between the open jaws, the user may disengage the actuator to transition the jaws to a closed configuration suitable for tissue ablation. Alternatively, a user may engage the actuator to transition the jaws from an open configuration to a closed configuration to allow, for example, the device to be advanced into a body cavity. When the device is adjacent to a desired portion of tissue, the user may disengage the actuator to transition the jaws to an open configuration to allow the desired portion of tissue to be positioned between the open jaws. With the tissue disposed between the jaws, the user may then engage the actuator to transition the jaws to a closed configuration suitable for tissue ablation.

In some embodiments, the actuator may be configured for direct movement of the jaws such that when engaged, the actuator causes the jaws to move in a 1:1 ratio or some other ratio. That is, the actuator may be configured to limit, attenuate, and/or amplify a force applied by the jaws based on an amount of force applied to the actuator. In some embodiments, the ablation device (740) may include a spring configured to bias the jaws (710, 720) between different configurations. For example, a spring may be coupled to the jaws (710, 720) and be configured to bias the jaws (710, 720) towards the tissue ablation configuration in order to apply a compressive force to tissue held between the jaws (710, 720) when the ablation device is advanced into or retracted from a body cavity, the jaws may transition to a closed configuration where the jaws contact each other.

Figure 6:
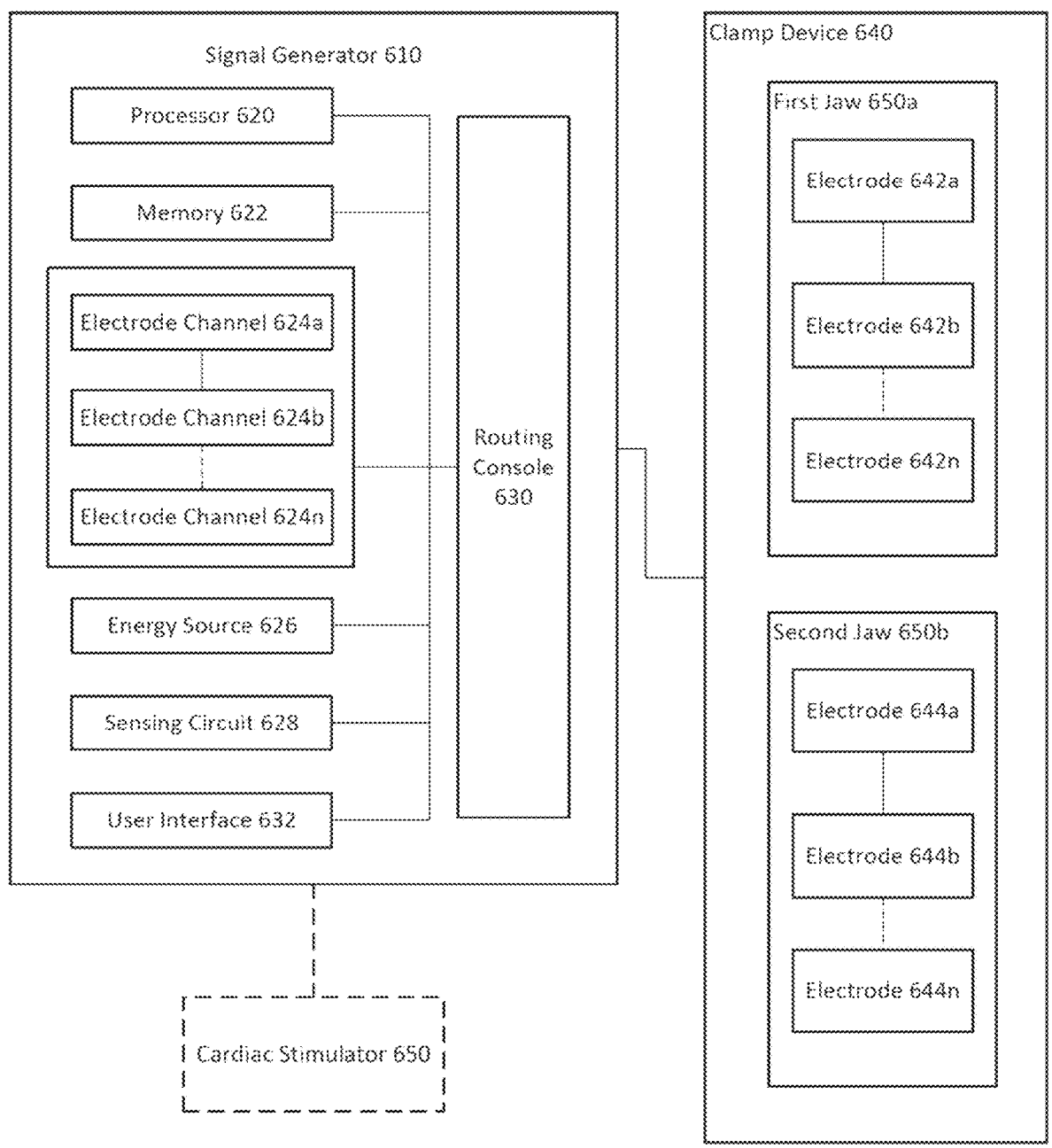
FIG. 6 is a block diagram of an electroporation system, according to embodiments.

FIG. 6 illustrates an ablation system (600) configured to deliver voltage pulse waveforms for tissue ablation. The system (600) may include a signal generator (610), ablation device (640), and optionally a cardiac stimulator (650). The signal generator (610) may be coupled to at least one ablation device (640), and optionally to the cardiac stimulator (650). The ablation device (640) may include a first jaw (650*a*) and a second jaw (650*b*). The first jaw (650*a*) may include a set of one or more electrodes (642*a*, 642*b*, . . . , 642*n*). The second jaw (650*a*) may include a set of one or more electrodes (644*a*, 644*b*, . . . , 644*n*).

Signal Generator

The signal generator (610) may be configured to generate pulse waveforms for irreversible electroporation of tissue, such as, for example, heart tissue. The signal generator (610) may be a voltage pulse waveform generator and deliver a pulse waveform to a set of electrodes (642*a*, 642*b*, . . . , 642*n*, and 644*a*, 644*b*, . . . , 644*n*) of the ablation device (640). The signal generator (610) may generate and deliver several types of signals including, but not limited to, radiofrequency (RF), direct current (DC) impulses (such as high-voltage, ultra-short pulses used in electroporation), stimulus range impulses, and/or hybrid electrical impulses. For example, the signal generator (610) may generate monophasic (DC) pulses or biphasic pulses (pulses of both polarities). The signal generator (610) may include a processor (620), memory (622), a set of electrode channels (624*a*, 624*b*, . . . , 624*n*, and 625*a*, 625*b*, . . . , 625*n*), energy source (626), sensing circuit (628), routing console (630), and user interface (632). One or more signal generator components may be coupled using a communication bus. The processor (620) may incorporate data received from one or more of memory (622), electrode channels (624*a*, 624*b*, . . . , 624*n*, and 625*a*, 625*b*, . . . , 625*n*), energy source (626), sensing circuit (628), routing console (630), user interface (632), ablation device (640), and cardiac stimulator (650) to determine the parameters (e.g., amplitude, width, duty cycle, timing, etc.) of the voltage pulse waveform to be generated by the signal generator (610). The memory (622) may further store instructions to cause the processor (620) to execute modules, processes and/or functions associated with the system (600), such as pulse waveform generation and delivery, electrode channel configuration, and/or cardiac pacing synchronization. For example, the memory (622) may be configured to store anode/cathode configuration data, electrode channel configuration data, pulse waveform data, fault data, energy discharge data, heart pacing data, patient data, clinical data, procedure data, electromyography data, sensor data, temperature data, and/or the like.

In some embodiments, the ablation device (640) may include a catheter configured to receive and/or deliver the pulse waveforms described herein. For example, the ablation device (640) may be introduced into an epicardial space of the left atrium and positioned to align one or more electrodes (642a, 642b, . . . , 642n, and 644a, 644b, . . . , 644n) to heart tissue (e.g., pulmonary vein), and then deliver the pulse waveforms to ablate tissue. The ablation device (140) may include one or more electrodes (642a, 642b, . . . , 642n, and 644a, 644b, . . . , 644n), which may, in some embodiments, be a set of independently addressable electrodes. For example, the electrodes (642a, 642b, . . . , 642n, and 644a, 644b, . . . , 644n) may be grouped into one or more anode-cathode subsets such as, for example, a subset including one anode and one cathode, a subset including two anodes and two cathodes, a subset including two anodes and one cathode, a subset including one anode and two cathodes, a subset including three anodes and one cathode, a subset including three anodes and two cathodes, and/or the like. The set of electrodes (642a, 642b, . . . , 642n, and 644a, 644b, . . . , 644n) may include any number of electrodes, for example, 2, 3, 4, 5, 6, 7, 8, 9, 10, 12, or more electrodes. In some embodiments, the methods, systems, and devices disclosed herein may comprise one or more of the methods, systems, and devices described in International Patent Application Serial No. PCT/US2018/029552, filed on Apr. 26, 2018, and titled "SYSTEMS, DEVICES, AND METHODS FOR SIGNAL GENERATION," International Application Serial No. PCT/US2019/014226, filed on Jan. 18, 2019, and titled "SYSTEMS, DEVICES, AND METHODS FOR FOCAL ABLATION," and International Application Serial No. PCT/US2013/031252, filed on Mar. 14, 2013, and titled "CATHETERS, CATHETER SYSTEMS, AND METHODS FOR PUNCTURING THROUGH A TISSUE STRUCTURE AND ABLATING A TISSUE REGION," the contents of which are hereby incorporated by reference in their entirety.

In some embodiments, the processor (620) may be any suitable processing device configured to run and/or execute a set of instructions or code and may include one or more data processors, image processors, graphics processing units, physics processing units, digital signal processors, and/or central processing units. The processor (620) may be, for example, a general purpose processor, Field Programmable Gate Array (FPGA), an Application Specific Integrated Circuit (ASIC), and/or the like. The processor (620) may be configured to run and/or execute application processes and/or other modules, processes and/or functions associated with the system and/or a network associated therewith (not shown). In some embodiments, the processor may comprise both a microcontroller unit and an FPGA unit, with the microcontroller sending electrode sequence instructions to the FPGA. The underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, and/or the like.

In some embodiments, the memory (622) may include a database (not shown) and may be, for example, a random access memory (RAM), a memory buffer, a hard drive, an erasable programmable read-only memory (EPROM), an electrically erasable read-only memory (EEPROM), a read-only memory (ROM), Flash memory, etc. The memory (622) may store instructions to cause the processor (620) to execute modules, processes and/or functions associated with the system (600), such as pulse waveform generation, electrode channel configuration, and/or cardiac pacing.

In some embodiments, a set of electrode channels (624a, 624b, . . . , 624n, and 625a, 625b, . . . , 625n) may include a set of active solid-state switches. The set of electrode channels (624a, 624b, . . . , 624n, and 625a, 625b, . . . , 625n) may be configured in a number of ways, including independent anode/cathode configuration for each electrode channel. For example, the electrode channels (624a, 624b, . . . , 624n, and 625a, 625b, . . . , 625n) may be grouped into one or more anode-cathode subsets such as, for example, a subset including one anode and one cathode, a subset including two anodes and two cathodes, a subset including two anodes and one cathode, a subset including one anode and two cathodes, a subset including three anodes and one cathode, a subset including three anodes and two cathodes, and/or the like. The set of electrode channels (624a, 624b, . . . , 624n, and 625a, 625b, . . . , 625n) may include any number of channels, for example, 2, 3, 4, 5, 6, 7, 8, 9, 10, 12, or more electrode channels. Energy delivery may use any combination of electrode channels (624a, 624b, . . . , 624n, and 625a, 625b, . . . , 625n) and any order for an energy delivery sequence.

The set of electrode channels (624a, 624b, . . . , 624n, and 625a, 625b, . . . , 625n) may be coupled to a routing console (630) to deliver energy to a set of electrodes (642) coupled to the routing console (630). The set of electrode channels (624a, 624b, . . . , 624n, and 625a, 625b, . . . , 625n) may be coupled to an energy source (626) to receive energy (e.g., a pulse waveform). Processor (620) may be coupled to each electrode channel (624a, 624b, . . . , 624n, and 625a, 625b, . . . , 625n) to configure an anode/cathode configuration for each electrode channel (624), which may be configured on a per pulse basis, per operator input, and/or the like. The processor (620) and energy source (626) may be collectively configured to deliver a pulse waveform to the set of electrodes (642, 644) through the set of electrode channels (624a, 624b, . . . , 624n, and 625a, 625b, . . . , 625n). In some embodiments, each electrode channel (624a, 624b, . . . , 624n, and 625a, 625b, . . . , 625n) may include an electronic switch (e.g., bipolar transistor) and a drive circuit, as described in detail herein. In some embodiments, each electrode channel (624a, 624b, . . . , 624n, and 625a, 625b, . . . , 625n) may have a bootstrap configuration for low and high frequency operation. For example, the pulse duration of voltage pulses delivered through an electrode channel may be in the range of between about 1 microsecond and about 1000 microseconds. In biphasic mode, this corresponds to an approximate frequency range of between about 500 Hz and about 500 KHz for the frequency associated with the voltage pulses.

In some embodiments, a pulse generator including a controller with the processor (620) and memory (622) may be coupled to each electrode of the set of first electrodes (642) and the set of second electrodes (644). The pulse generator and/or controller may be configured to generate a pulse waveform, configure a first set of electrodes of the set of first electrodes (642) and the set of second electrodes (644) for pulse waveform delivery. The pulse waveform may be delivered to the first set of electrodes (642). In some embodiments, a second set of electrodes of the set of first electrodes (642) and the set of second electrodes (644) may be configured for receiving electrical activity of tissue. Signal data corresponding to the electrical activity of the tissue may be received using the second set of electrodes. Electrocardiography data may be generated using the signal data.

In some embodiments, an energy source (626) may be configured to convert and supply energy to a set of electrodes (642, 644) coupled to the signal generator (610). The energy source (626) of the signal generator (610) may include a DC power supply and be configured as an AC/DC switcher. In some embodiments, an energy source (626) of the signal generator (610) may deliver rectangular-wave pulses with a voltage in the range between about 300 V and about 5000 V. In some of these embodiments, the energy source (626) may be configured to store energy. For example, the energy source (626) may include one or more capacitors to store energy from a power supply. While these examples are included for purely non-limiting illustrative purposes, it is noted that a variety of pulse waveforms with a range of pulse durations, intervals between pulses, pulse groupings, etc. may be generated depending on the clinical application.

In some embodiments, a sensing circuit (628) may be configured to determine an amount of current being delivered to a device coupled to the signal generator (610) (e.g., electrode (642) coupled to the electrode channel (624)). As described in more detail herein, the sensing circuit (628) may also be used to classify an electrode channel fault, monitor capacitor discharge, and/or sense arcing. In some embodiments, the sensing circuit (628) may be a direct current sensing circuit and/or a low-side sensing circuit. The sensing circuit may include one or more operational amplifiers, difference amplifiers (DA), instrumentation amplifiers (IA), and/or current shunt monitors (CSM).

In some embodiments, the routing console (630) may be configured to electrically couple a set of electrodes (642) of an ablation device (640) to a set of electrode channels (624a, 624b, . . . , 624n, and 625a, 625b, . . . , 625n). The routing console (630) may be configured to selectively deliver energy to the set of electrodes (642) using the set of electrode channels (624a, 624b, . . . , 624n, and 625a, 625b, . . . , 625n). One or more ablation devices (640) each having a set of electrodes (642, 644) may be coupled to the routing console (630). The set of electrodes (642, 644) may include any number of electrodes, for example, 1, 2, 3, 4, 5, 6, 7, 8, 9, 10, 12, or more electrodes. In some embodiments, an ablation device (640) may include three electrodes with a first jaw (650a) having a first electrode (642a) and a second jaw (650b) having a second electrode (644a) and a third electrode (644b).

In some embodiments, the electrode channels (624a, 624b, . . . , 624n, and 625a, 625b, . . . , 625n) configured for energy delivery (e.g., configured as an anode/cathode pair of electrode channels) may not be adjacent to each other. For example, the set of electrode channels (624a, 624b, . . . , 624n, and 625a, 625b, . . . , 625n) may include a set of N electrode channels (624a, 624b, . . . , 624n, and 625a, 625b, . . . , 625n) in a parallel array. In one embodiment, a first electrode channel may correspond to a first electrode channel (624a) in the parallel array of N electrode channels (624a, 624b, . . . , 624n, and 625a, 625b, . . . , 625n). One or more of a second and third electrode channel (624b, 624c) may not be adjacent to the first electrode channel (624a) in the parallel array of N electrode channels (624a, 624b, . . . , 624n, and 625a, 625b, . . . , 625n).

A multi-electrode ablation device may allow targeted and precise energy delivery to tissue. In some embodiments, the electrodes (642, 644) of an ablation device (640) may be configured for energy delivery (e.g., as an anode/cathode pair of electrodes (642, 644)) and may be disposed on opposing jaws on respective parallel arrays of the ablation device (640). For example, an ablation device (640) may include a first jaw (650a) having a set of first electrodes (642) as a parallel array of N electrodes (142n) and a second jaw (650b) having a set of second electrodes (644) as a parallel array of M electrodes (644n). The signal generator (610) coupled to the ablation device (640) may include a set of electrode channels (624a, 624b, . . . , 624n, and 625a, 625b, . . . , 625n) having N electrode channels corresponding to the M electrodes (642n, 644n) of the ablation device (640). In one embodiment, the first electrode channel (624a) of the N electrode channels (624a, 624b, . . . , 624n, and 625a, 625b, . . . , 625n) may correspond to a first electrode (642a) in the parallel array of M electrodes (642n) of the first jaw (650a). One or more of second and third electrode channel (624b, 624c) of the N electrode channels (624n) may not correspond to any of the electrodes adjacent to the first electrode (642a) in the parallel array of M electrodes (642n). For example, the second electrode channel (642b) may correspond to a second electrode (644a) in the parallel array of M electrodes (644n) of the second jaw (650b).

Configurable electrode channel and electrode selection may provide flexibility in positioning the electrodes for ablating a desired region of interest, as described in more detail herein. In some embodiments, the routing console (630) may couple to a set of four or six electrodes (642, 644) of an ablation device (640). The routing console (630) may receive input from the processor (620) and/or user interface (632) for electrode channel selection and energy delivery to one or more electrodes (642, 644). Additionally or alternatively, the routing console (630) may couple to a cardiac stimulator (650) and be configured to receive data from devices (e.g., heart pacing data from a pacing device) used for synchronization of a pulse waveform with a patient cardiac cycle.

In some embodiments, a user interface (632) may be configured as a communication interface between an operator and the system (600). The user interface (632) may include an input device and output device (e.g., touch surface and display). For example, patient data from memory (622) may be received by user interface (632) and output visually and/or audibly. Electric current data from sensing circuit (628) may be received and output on a display of user interface (632). As another example, operator control of an input device having one or more buttons, knobs, dials, switches, trackball, touch surface, and/or the like, may generate a control signal to the signal generator (610) and/or ablation device (640).

In some embodiments, an input device of the user interface (632) may include a touch surface for operator input and may be configured to detect contact and movement on the touch surface using any of a plurality of touch sensitivity technologies including capacitive, resistive, infrared, optical imaging, dispersive signal, acoustic pulse recognition, and surface acoustic wave technologies. Additionally or alternatively, the user interface (632) may include a step switch or foot pedal.

In some embodiments, an output device of the user interface (632) may include one or more of a display device and audio device. The display device may include at least one of a light emitting diode (LED), liquid crystal display (LCD), electroluminescent display (ELD), plasma display panel (PDP), thin film transistor (TFT), and organic light emitting diodes (OLED). An audio device may audibly output patient data, sensor data, system data, other data, alarms, warnings, and/or the like. The audio device may include at least one of a speaker, piezoelectric audio device, magnetostrictive speaker, and/or digital speaker. In one embodiment, the audio device may output an audible warning upon detection of a fault in the signal generator (610) and/or ablation device (640).

In some embodiments, the signal generator (610) may be mounted on a trolley or cart. In some embodiments, the user interface (632) may be formed in the same or different housing as the signal generator (610). The user interface (632) may be mounted to any suitable object, such as furniture (e.g., a bed rail), a wall, a ceiling, or may be self-standing. In some embodiments, the input device may include a wired and/or wireless transmitter configured to transmit a control signal to a wired and/or wireless receiver of the signal generator (610).

In some embodiments, a cardiac stimulator (650) including a pacing device may be configured to generate a heart pacing signal to be delivered to a patient via the pacing device. An indication of the pacing signal may be transmitted by the cardiac stimulator (650) to the signal generator (610). Based on the pacing signal, an indication of a voltage pulse waveform may be selected, computed, and/or otherwise identified by the processor (620) and generated by the signal generator (610). In some embodiments, the signal generator (610) may be configured to generate the voltage pulse waveform in synchronization with the indication of the pacing signal (e.g., within a common refractory window). For example, in some embodiments, the common refractory window may start substantially immediately following a ventricular pacing signal (or after a very small delay) and last for a duration of between about 150 ms and about 250 ms thereafter. In such embodiments, an entire pulse waveform may be delivered within this duration.

In some embodiments, the systems described herein may include one or more sterile coverings configured to create a sterile barrier around portions of the system (600). In some embodiments, the system (600) may include one or more sterile coverings to form a sterile field. For example, a sterile covering may be placed over the user interface of the signal generator. The sterile covering may include, for example, a sterile drape configured to cover at least a portion of a system component. In one embodiment, a sterile covering (e.g., sterile drape) may be configured to create a sterile barrier with respect to a user interface (632) of the system (600). The sterile drape may be clear and allow an operator to visualize and manually manipulate the user interface (632). The sterile covering may conform tightly around one or more system components or may drape loosely to allow components to be adjusted within the sterile field.

Ablation Device

The systems described here may include one or more multi-electrode ablation devices configured to ablate tissue for treating atrial fibrillation. Generally, the ablation devices may include a first jaw and a second jaw sized and shaped to physically engage, hold, and (optionally) compress tissue therebetween for delivery of ablation energy. In some embodiments, a distal end of the first jaw and the second jaw may be generally atraumatic to decrease the risk of damage to tissue through laceration, puncture, and other damage when releasably coupled thereto. For example, the first jaw and second jaw may form atraumatic surfaces and edges (e.g., rounded, blunt) to contact and/or hold tissue without causing damage. A set of metallic electrodes disposed on each of the jaws and may also be generally atraumatic to decrease the risk of damage to tissue through laceration and puncture. For example, the edges of the electrodes may be rounded to reduce tissue damage and to increase the uniformity of the electric field generated at a central portion and a peripheral portion of the electrodes. The electrodes may generally form an elongate member (e.g., bar, strip) that extends generally parallel to a length of the jaws. The electrodes may have a length greater than a width or height/depth dimension of the electrode. The jaws as described in more detail herein may be composed of an electrically insulating material such as a polymeric or ceramic material.

In order to deliver the pulse waveforms generated by the signal generator, one or more electrodes of the ablation device may have an insulated electrical lead configured for sustaining a voltage potential of at least about 300 V without dielectric breakdown of its corresponding insulation. In some embodiments, the insulation on each of the electrical leads may sustain an electrical potential difference of between about 200 V to about 3,000 V across its thickness without dielectric breakdown, including all values and subranges in between. In some embodiments, the electrodes may be independently addressable such that each electrode may be controlled (e.g., deliver energy) independently of any other electrode of the device. In this manner, the electrodes may deliver different energy waveforms with different timing synergistically for electroporation of tissue. The electrodes may, for example, be connected to an insulated electrical lead leading to a handle to receive pulse waveforms generated by a signal generator as discussed above with respect to FIG. 6.

Figure 1B:
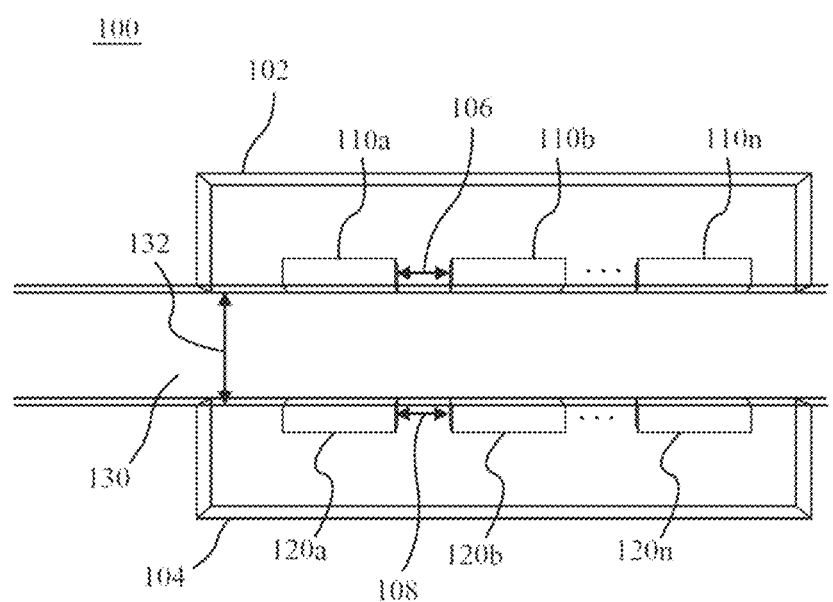
FIG. 1B is a schematic cross-sectional side view of an ablation device, according to embodiments.

FIG. 1A is a schematic perspective view of an exemplary ablation device (100) including a first jaw (102) and a second jaw (104) that may be structurally and/or functionally similar to the ablation device in FIG. 6. The first jaw (102) may include a set of first electrodes (110*a*, 110*b*, . . . , 110*n*) (e.g., first plurality of electrodes) and the second jaw (104) may include a set of second electrodes (120*a*, 120*b*, . . . , 120*n*) (e.g., second plurality of electrodes), as shown in FIG. 1B. The first jaw (102) and the second jaw (104) may be spaced apart and substantially parallel (e.g., extend parallel to one another) and configured to engage tissue (130) therebetween during use. In some embodiments, the first jaw (102) and the second jaw (104) may transition between a set of configurations having different jaw measures (132) (e.g., spacing, distance). In some embodiments, the first jaw (102) and second jaw (104) may be configured to transition between a first configuration for passing the first and second jaws through a body cavity, organ system, or anatomical structure and a second configuration for engaging the tissue (130). The first jaw (102) and the second jaw (104) may be spaced apart by a spacing distance in the second configuration (e.g., third measure (132) as described in more detail herein). The first jaw (102) and the second jaw (104) may be collectively configured to define a longitudinal axis (140). The first jaw (102) and the second jaw (104) may be substantially rigid.

The set of first electrodes (110) and the set of second electrodes (120) may be arranged parallel to the longitudinal axis (140) of the jaws (102, 104). Each of the first electrodes (110) may be spaced apart from an adjacent first electrode (110) by a first measure (106) (e.g., spacing, distance) and each of the second electrodes (120) may be spaced apart from an adjacent second electrode (120) by a second measure (108). The set of first electrodes (110) may be disposed on a side of the first jaw (102) facing the second jaw (104) with each of the set of first electrodes (110) spaced apart laterally with respect to the longitudinal axis (140). Similarly, the set of second electrodes (120) may be disposed on a side of the second jaw (104) facing the first jaw (102) with each of the set of second electrodes (120) spaced apart laterally with respect to the longitudinal axis (140). As shown in FIG. 1B, each electrode of the set of first electrodes (110) and the set of second electrodes (120) may include an exposed portion in electrical contact with tissue (130) during use. The exposed portion of each electrode of the set of first electrodes (110) and the set of second electrodes (120) may be flat or convex.

At least two of the set of first electrodes (110) may be spaced apart by a first measure (106), and at least two of the set of second electrodes (120) may be spaced apart by a second measure (108), as shown in FIG. 1B. The first jaw (102) and the second jaw (104) may be spaced apart by a third measure (132). For example, the set of first electrodes may be spaced apart by a distance between about 1 mm and about 6 mm, while the set of second electrodes may be spaced apart by a distance between about 1 mm and about 4 mm. The first jaw and the second jaw may be spaced apart by a distance between about 1 mm and about 15 mm.

In some embodiments, each electrode of the set of first electrodes (110) and the set of second electrodes (120) may have a width orthogonal to the longitudinal axis that is less than a length of that electrode that is parallel to the longitudinal axis (140) where the set of first electrodes (110) are spaced apart laterally with respect to the longitudinal axis (140). In particular, each electrode of the set of first electrodes (110) has, within a cross-section of the apparatus (e.g., a cross-section of the first jaw (102) and the second jaw (104)) that is orthogonal to the longitudinal axis, a width that is less than a length of that electrode, where the set of first electrodes (110) are spaced apart laterally. In some embodiments, any two adjacent electrodes of the set of first electrodes (110) may have a first measure of between about 0.5 mm and about 10 mm and any two adjacent electrodes of the set of second electrodes (120) may have a second measure of between about 0.5 mm and about 10 mm.

In some embodiments, each electrode of the set of first electrodes (110) and the set of second electrodes (120) may have a length of between about 1 cm and about 8 cm, a width of between about 1 mm and about 5 mm, and a height of between about 0.5 mm and about 3 mm. In some embodiments, the set of first electrodes (110) and the set of second electrodes (120) may have a length to width ratio of at least about 3:1.

The set of first electrodes (110) and the set of second electrodes (120) may have a shape of an elongate electrode. In some embodiments, each electrode of the set of first electrodes (110) and the set of second electrodes (120) may be substantially rectangular, e.g., have a cross-sectional shape that is rectangular. In other embodiments, each electrode of the set of first electrodes (110) and the set of second electrodes (120) may include a curved portion.

In some embodiments, each electrode of the set of first electrodes (110) and the set of second electrodes (120) may be independently addressable. One or more lead wires may be coupled to the set of first electrodes (110) and the set of second electrodes (120). In some embodiments, the electrodes may comprise a generally elliptical or circular cross-section. A length of a semi-major axis of the electrode may be between about 0.5 mm and about 5 mm. In some of these embodiments, a length to width ratio of the electrode may be at least about 3:1.

In some embodiments, an electrode of the set of first electrodes (110) may be configured as an anode and an electrode of the set of second electrodes (120) may be configured as a cathode. For example, the anode may be disposed directly across from the cathode. For example, a first electrode pairing may include electrodes (110a, 120a) directly across from each other on opposing jaws (102, 104) within the cross-section of FIG. 1B (e.g., a cross-section of the opposing jaws (102, 104)) orthogonal to the longitudinal axis, a second electrode pairing may include electrodes (110b, 120b) directly across from each other on opposing jaws (102, 104) within the cross-section orthogonal to the longitudinal axis, and so forth for n electrodes.

In other embodiments, the anode may be diagonal from the cathode within the cross-section orthogonal to the longitudinal axis. In some embodiments, the anode may generally be spaced apart laterally from the cathode with respect to the longitudinal axis. In some embodiments, a first electrode pairing may include electrodes (110a, 120b) spaced apart laterally from each other on opposing jaws (102, 104) within the cross-section orthogonal to the longitudinal axis and a second electrode pairing may include electrodes (110b, 120a) spaced apart laterally from each other on opposing jaws (102, 104) with respect to the longitudinal axis, and so forth for n electrodes.

In some embodiments, one electrode of the set of first electrodes (110) may be configured as an anode while another electrode of the set of first electrodes (110) may be configured as a cathode. In some embodiments, one electrode of one of the jaws may be configured as an anode while another electrode of the same jaw may be configured as a cathode. In some embodiments, a first electrode pairing may include electrodes (110a, 110b) adjacent to each other on the same first jaw (102) within the cross-section orthogonal to the longitudinal axis, a second electrode pairing may include electrodes (120a, 120b) adjacent to each other on the same second jaw (104) within the cross-section orthogonal to the longitudinal axis, and so forth for n electrodes.

A pre-determined ablation sequence may include delivering ablation pulse waveforms over a sequence of pre-defined electrode pairings. In some embodiments, the sequenced delivery may be triggered from a cardiac stimulator and/or pacing device. In some embodiments, the ablation pulse waveforms may be applied in a refractory period of the cardiac cycle to avoid disruption of the sinus rhythm of the heart, as described in more detail herein. One or more of the electrodes may be configured to receive signal data corresponding to electrical activity of the tissue (e.g., electrocardiography data).

In some embodiments, a handle such as the handle shown in FIG. 7 may be coupled to the first jaw (102) and the second jaw (104). The handle may include one or more of a jaw control configured to control a spacing and/or angle between the first jaw (102) and the second jaw (104), electrode selection control, and pulse waveform control. In some embodiments, the first jaw (102) and the second jaw (104) may be coupled by a pivot (not shown) in which case, the jaws may form an angle with respect to each other. In some embodiments, the device (100) may include a spring (not shown) configured to bias the first jaw (102) and the second jaw (104) toward each other. In some embodiments, the first jaw (102) may be fixed relative to the handle while the second jaw (104) is configured to move relative to the first jaw (102).

Figure 8:
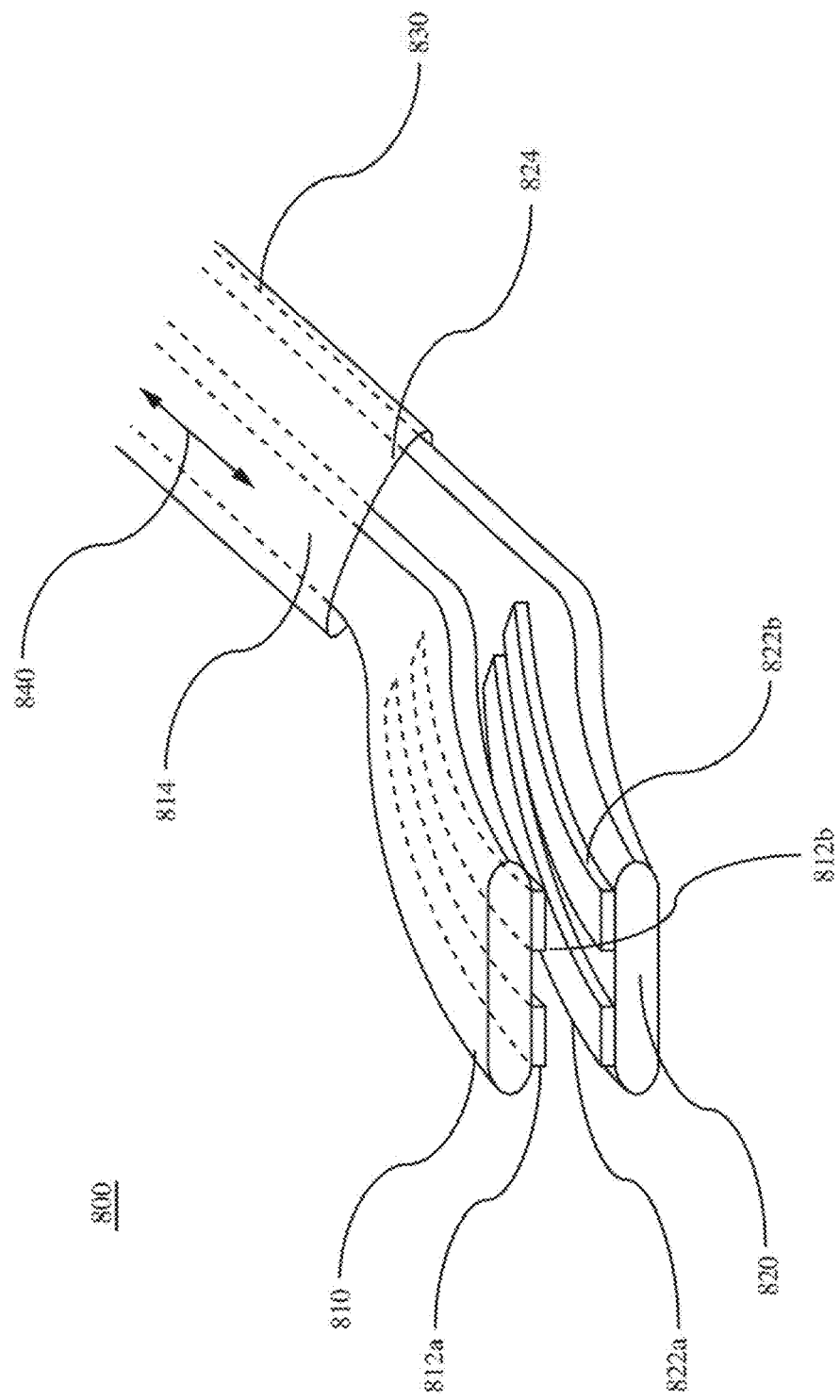
FIG. 8 is a perspective view of a distal end of an ablation device, according to embodiments.

FIG. 8 is a perspective view of a distal end of an ablation device (800) that may be structurally and/or functionally similar to the ablation device in FIG. 6. The ablation device (800) may include a body (830) having a lumen extending therethrough, a first jaw (810), and a second jaw (820). The first jaw (810) may include a first shaft (814) that extends through the lumen of the body (830). Likewise, the second jaw (820) may include a second shaft (824) that extends through the lumen of the body (830). In some embodiments, one or both of the jaws (810, 820) may move in a direction (840) relative to each other in order to modify a spacing between the first and second jaws (810, 820). In some embodiments, the jaws (810, 820) may be movable relative to the body (830) such that the jaws (810, 820) may advance and retract into and out of the body (830). Retraction of the jaws (810, 820) permits grasping a portion of tissue between the jaws. When the moveable jaw is released, the tissue may then be firmly held in place between the jaws. FIG. 8 shows a first jaw (810) and a second jaw (820) having a generally elliptical (e.g., arcuate) shape. The jaws (810, 820) may be substantially rigid and parallel to each other.

A distal end of the first jaw (810) may include a set of first electrodes such as the two electrodes (812a, 812b) shown in FIG. 8. Likewise, a distal end of the second jaw (812) may include a set of second electrodes such as the two electrodes (822a, 822b) shown in FIG. 8. The pair of first electrodes (812a, 812b) and the pair of second electrodes (822a, 822b) may be arranged to be parallel, although they may be arcuate along their lengths. A set of tangent vectors to the elongate shape of each jaw may be defined, and a local longitudinal axis may, for example, pass through the center of the cross-section of either jaw such that the local longitudinal axis is parallel to the local tangent vector. Each of the first electrodes (812a, 812b) may be spaced apart from each other and each of the second electrodes (822a, 822b) may be spaced apart from each other. The local electrode cross-section may be generally perpendicular to the local longitudinal axis. The set of first electrodes (812) and the set of second electrodes (822) may be elongate electrodes. Some electrodes on opposite jaws may be directly across from each other, such that the normal to an electrode on one jaw points directly towards an electrode on the other jaw. In some embodiments, each electrode of the set of first electrodes (812) and the set of second electrodes (822) may be substantially rectangular. In other embodiments, each electrode of the set of first electrodes (812) and the set of second electrodes (822) may include a curved portion such as a generally arcuate shape or rounded edges. The electrodes may include a curvature that generally follows a curvature of its respective jaw.

The first electrodes (812a, 812b) may be disposed on a side of the first jaw (810) facing the second jaw (820). Similarly, the second electrodes (822a, 822b) may be disposed on a side of the second jaw (820) facing the first jaw (810). Each electrode of the first electrodes (812a, 812b) and the second electrodes (822a, 822b) may include an exposed portion in electrical contact with tissue during use. The exposed portion of each electrode of the first electrodes (812a, 812b) and the second electrodes (822a, 822b) may be flat or convex. Each electrode (812a, 812b, 822a, 822b) may have an insulated electrical lead associated therewith. The insulated electrical leads may be disposed in a corresponding shaft. In some embodiments, each electrode of the set of first electrodes (812) and the set of second electrodes (822) may be independently addressable. In some embodiments, the electrodes (812a, 812b, 822a, 822b) may have a length of between about 1 cm and about 8 cm, a width of between about 1 mm and about 5 mm, and a height of between about 0.5 mm and about 3 mm. In some embodiments the electrodes (812a, 812b, 822a, 822b) may have a length to width ratio of at least about 3:1.

In some embodiments, an electrode of the set of first electrodes (812) may be configured as an anode and an electrode of the set of second electrodes (822) may be configured as a cathode. For example, the anode may be disposed directly across from the cathode within the cross-section orthogonal to the longitudinal axis. In some embodiments, a first electrode pairing may include electrodes (812a, 822a) directly across from each other on opposing jaws (810, 820) within the cross-section orthogonal to the longitudinal axis and a second electrode pairing may include electrodes (812b, 822b) directly across from each other on opposing jaws (810, 820) within the cross-section orthogonal to the longitudinal axis.

In other embodiments, the anode may be diagonal from the cathode such that the anode is laterally spaced apart from the cathode with respect to the longitudinal axis and/or does not intersect a line perpendicular to the cathode. In some embodiments, a first electrode pairing may include electrodes (812a, 822b) spaced apart laterally from each other on opposing jaws (810, 820) and a second electrode pairing may include electrodes (812b, 822a) spaced apart laterally from each other on opposing jaws (810, 820) with respect to the longitudinal axis. This combination of electrode pairing may reduce, if not eliminate, the risk of the electrodes electrically shorting in cases where tissue is incompletely grasped between the jaws and/or portions of the jaws touch each other.

In some embodiments, one electrode of one of the jaws may be configured as an anode while another electrode of the same jaw may be configured as a cathode. In some embodiments, a first electrode pairing may include electrodes (812a, 812b) adjacent to each other on the same jaw (810) and a second electrode pairing may include electrodes (822a, 822b) adjacent to each other on the same jaw (820).

Generally in the embodiments described herein, pulsed electric field ablation is delivered in order to generate irreversible electroporation in the tissue between the jaws. A pre-determined ablation sequence may include delivering ablation pulse waveforms sequentially over a pre-defined set of electrode pairings, for example first and second electrode pairings when a set of two electrode pairings are configured. In some embodiments, the sequenced delivery may be triggered from a cardiac stimulator and/or pacing device. In some embodiments, the ablation pulse waveforms may be applied in a refractory period of the cardiac cycle to avoid disruption of the sinus rhythm of the heart, as described in more detail herein. One or more of the electrodes may be configured to receive signal data corresponding to electrical activity of the tissue (e.g., electrocardiography data).

In some embodiments, a handle such as the handle shown in FIG. 7 may be coupled to the first jaw (810) and the second jaw (820). The handle may include one or more of a jaw control configured to control a spacing and/or angle between the first jaw (810) and the second jaw (820), electrode selection control, and pulse waveform control. In some embodiments, the first jaw (810) and the second jaw (820) may be coupled by a pivot (not shown) in which case, the jaws may form an angle with respect to each other. In some embodiments, the device (800) may include a spring (not shown) configured to bias the first jaw (810) and the second jaw (820) toward each other. In some embodiments, the first jaw (810) may be fixed relative to the handle while the second jaw (820) is configured to move relative to the first jaw (810).

Figure 9A:
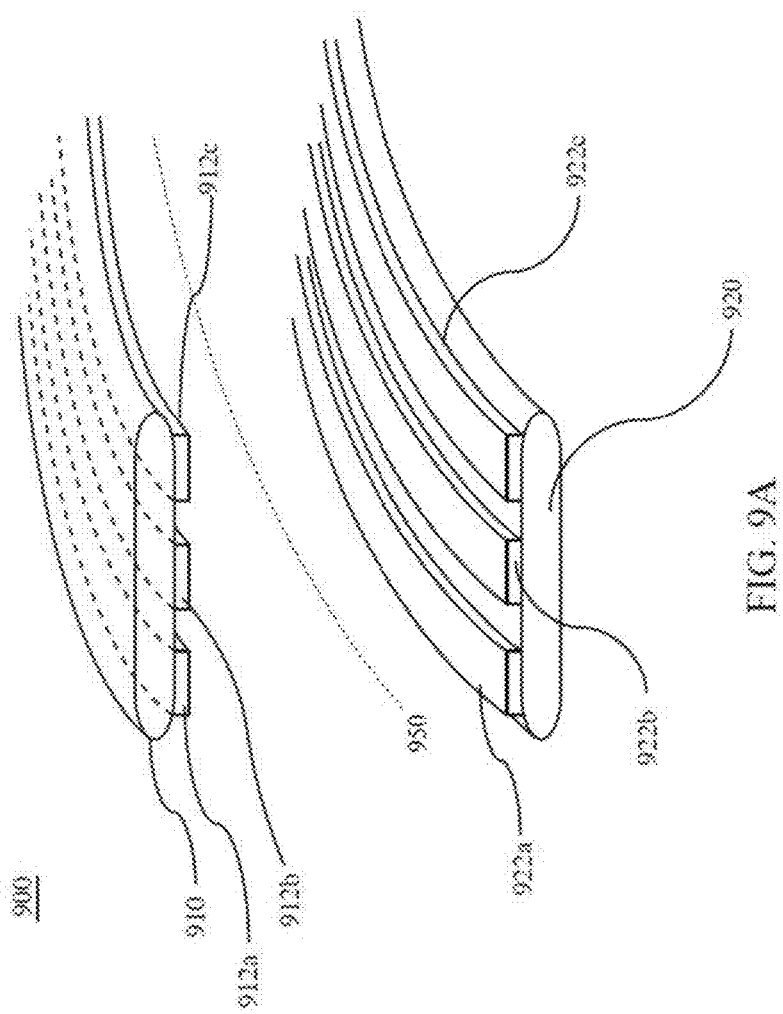
FIG. 9A is a perspective view of a distal end of an ablation device, according to embodiments.
Figure 9B:
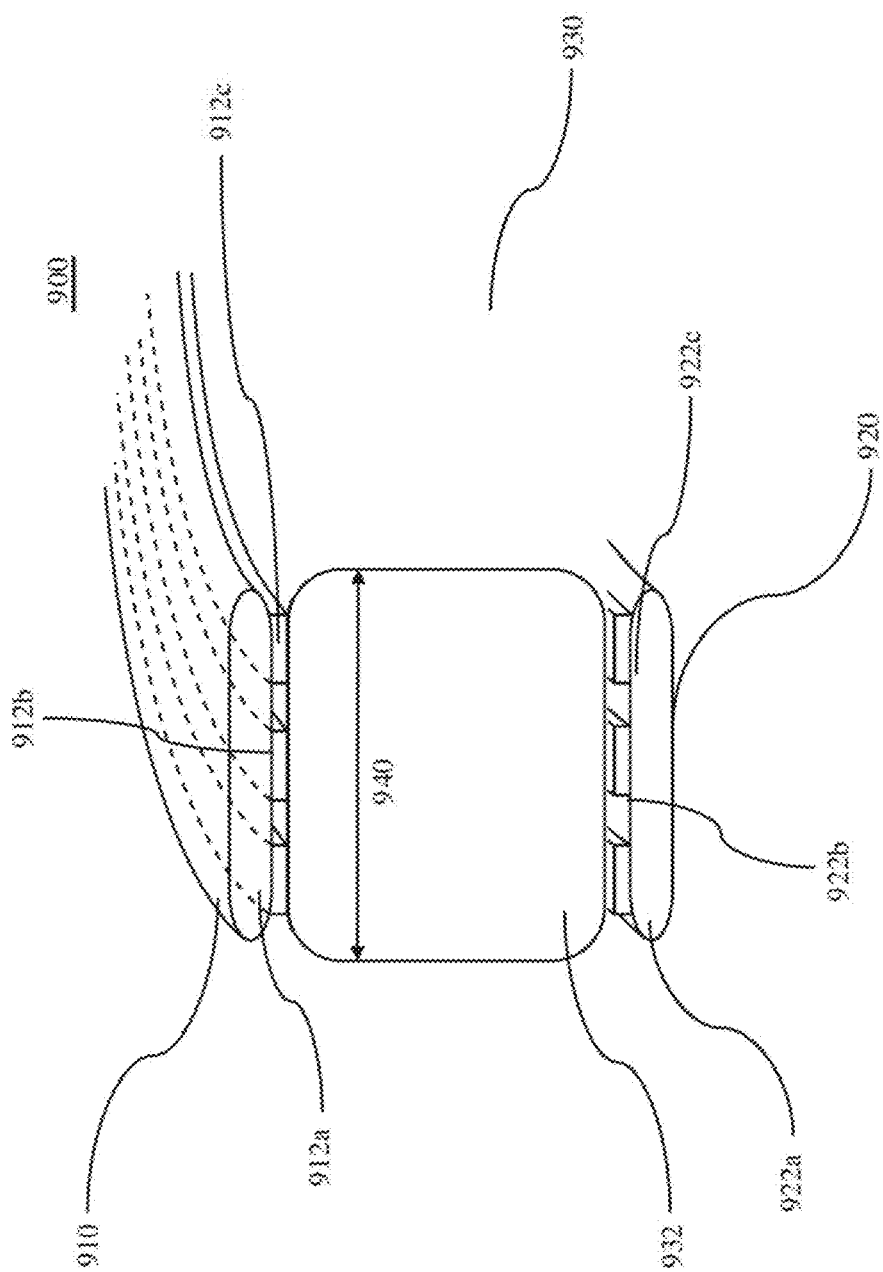
FIG. 9B is a perspective view of a distal end of an ablation device shown in FIG. 9A having tissue disposed in between the arms of the device, according to embodiments.

FIGS. 9A-9B are perspective views of a distal end of an ablation device (900) that may be structurally and/or functionally similar to the ablation device in FIG. 6. The ablation device (900) may include a first jaw (910) and a second jaw (920). In some embodiments, one or both of the jaws (910, 920) may move in a direction relative to each other in order to modify a spacing between the first and second jaws (910, 920). FIGS. 9A-9B show a first jaw (910) and a second jaw (920) having a generally elliptical (e.g., arcuate) shape. The jaws (910, 920) may be substantially rigid and parallel to each other. The jaws (910, 920) may collectively define a curved longitudinal axis (950).

A distal end of the first jaw (910) may include a set of first electrodes such as the three electrodes (912a, 912b, 912c) shown in FIGS. 9A-9B. Likewise, a distal end of the second jaw (912) may include a set of second electrodes such as the three electrodes (922a, 922b, 922c) shown in FIGS. 9A-9B. The trio of first electrodes (912a, 912b, 912c) and the trio of second electrodes (922a, 922b, 922c) orthogonal to the longitudinal axis may be arranged parallel to the curve of a long edge of the jaws.

Each of the first electrodes (912a, 912b, 912c) may be spaced apart from each other within the cross-section orthogonal to the longitudinal axis and each of the second electrodes (922a, 922b, 922c) may be spaced apart from each other within the cross-section orthogonal to the longitudinal axis. The set of first electrodes (912) and the set of second electrodes (922) may be elongate electrodes. In some embodiments, each electrode of the set of first electrodes (912) and the set of second electrodes (922) may be substantially rectangular. In other embodiments, each electrode of the set of first electrodes (912) and the set of second electrodes (922) may include a curved portion such as a generally arcuate shape or rounded edges. The electrodes may include a curvature such that generally each electrode follows the curvature of its respective jaw.

The first electrodes (912a, 912b, 912c) may be disposed on a side of the first jaw (910) facing the second jaw (920). Similarly, the second electrodes (922a, 922b, 922c) may be disposed on a side of the second jaw (920) facing the first jaw (910). Each electrode of the first electrodes (912a, 912b, 912c) and the second electrodes (922a, 922b, 922c) may include an exposed portion in electrical contact with tissue during use (FIG. 9B). The exposed portion of each electrode of the first electrodes (912a, 912b, 912c) and the second electrodes (922a, 922b, 922c) may be flat or convex. Each electrode (912a, 912b, 912c, 922a, 922b, 922c) may have an insulated electrical lead associated therewith. The insulated electrical leads may be disposed in a corresponding shaft. In some embodiments, each electrode of the set of first electrodes (912) and the set of second electrodes (922) may be independently addressable. In some embodiments, the electrodes (912a, 912b, 912c, 922a, 922b, 922c) may have a length of between about 1 cm and about 8 cm, a width of between about 1 mm and about 5 mm, and a height of between about 0.5 mm and about 3 mm. In some embodiments the electrodes (912a, 912b, 912c, 922a, 922b, 922c) may have a length to width ratio of at least about 3:1.

In some embodiments, an electrode of the set of first electrodes (912) may be configured as an anode and an electrode of the set of second electrodes (922) may be configured as a cathode. For example, the anode may be disposed directly across from the cathode. In some embodiments, a first electrode pairing may include electrodes (912a, 922a) directly across from each other on opposing jaws (910, 920), a second electrode pairing may include electrodes (912b, 922b) directly across from each other on opposing jaws (810, 820), and a third electrode pairing may include electrodes (912c, 922c) directly across from each other on opposing jaws (910, 920).

In other embodiments, the anode may be diagonal from the cathode within the cross-section orthogonal to the longitudinal axis such that the anode is laterally spaced apart from the cathode with respect to the longitudinal axis and/or does not intersect a line perpendicular to the cathode. In some embodiments, a first electrode pairing may include electrodes (912a, 922b) spaced apart laterally from each other on opposing jaws (910, 920) with respect to the longitudinal axis, a second electrode pairing may include electrodes (912b, 922a) spaced apart laterally from each other on opposing jaws (910, 920) with respect to the longitudinal axis, a third electrode pairing may include electrodes (912b, 922c) spaced apart laterally from each other on opposing jaws (910, 920) with respect to the longitudinal axis, and a fourth electrode pairing may include electrodes (912c, 922b) spaced apart laterally from each other on opposing jaws (910, 920) with respect to the longitudinal axis.

In some embodiments, one electrode of one of the jaws may be configured as an anode while another electrode of the same jaw may be configured as a cathode. In some embodiments, a first electrode pairing may include electrodes (912a, 912b) adjacent to each other on the same first jaw (910), a second electrode pairing may include electrodes (912b, 912c) adjacent to each other on the same first jaw (910), a third electrode pairing may include electrodes (922a, 922b) adjacent to each other on the same second jaw (920), and a fourth electrode pairing may include electrodes (922b, 922c) adjacent to each other on the same second jaw (920).

A pre-determined ablation sequence may include delivering ablation pulse waveforms sequentially over a pre-defined set of electrode pairings. In some embodiments, the sequenced delivery may be triggered from a cardiac stimulator and/or pacing device. In some embodiments, the ablation pulse waveforms may be applied in a refractory period of the cardiac cycle to avoid disruption of the sinus rhythm of the heart, as described in more detail herein. One or more of the electrodes may be configured to receive signal data corresponding to electrical activity of the tissue (e.g., electrocardiography data).

FIG. 9B is a perspective view of the ablation device (900) coupled to tissue (930) after undergoing one or more ablation sequences as described herein. In FIG. 9B, at least a portion of tissue (930) is held between the jaws (910, 920) of the device (900). In some embodiments, a tissue ablation zone (932) may have a width (940) that substantially corresponds to at least an end-to-end width between the electrodes (912a and 912c, 922a and 922c) of a jaw (910, 920). In some embodiments, the tissue (930) may comprise a portion of a pulmonary vein as shown, for example, in FIG. 10. Tissue between the jaws (910, 920) may be compressed relative to other portions of tissue (940).

In some embodiments, a handle such as the handle shown in FIG. 7 may be coupled to the first jaw (910) and the second jaw (920). The handle may include one or more of a jaw control configured to control a spacing and/or angle between the first jaw (910) and the second jaw (920), electrode selection control, and pulse waveform control. In some embodiments, the first jaw (910) and the second jaw (920) may be coupled by a pivot (not shown) in which case, the jaws may form an angle with respect to each other. In some embodiments, the device (900) may include a spring (not shown) configured to bias the first jaw (910) and the second jaw (920) toward each other. In some embodiments, the first jaw (910) may be fixed relative to the handle while the second jaw (920) is configured to move relative to the first jaw (910).

The electrodes as described may be composed of any suitable biocompatible conductive material including, but not limited to, one or more of silver, palladium, stainless steel, platinum, titanium, platinum-iridium alloys, gold, copper, nickel, combinations thereof, and the like. In some embodiments, the electrode materials may be plated, coated, and/or otherwise applied in an appropriately thick layer on top of a different substrate material. In some embodiments, electrode portions may be coupled using annealing, soldering, welding, crimping, lamination, combinations thereof, and the like. The jaws and body of the ablation devices disclosed may be composed of any suitable electrically insulating biocompatible material including polymers, ceramics, glasses, combinations thereof, and the like.

II. Methods

Also described here are methods for ablating tissue (e.g., pulmonary vein) using the systems and devices described above. The ablation devices described herein may be used for ablation of cardiac features/structures identified to cause arrhythmia. The pulmonary vein may be connected to the left atrium of the heart. Generally, the methods described here include introducing and disposing a device in contact with one or more pulmonary vein regions. A pulse waveform may be delivered by one or more electrodes of the device to ablate tissue. In some embodiments, a cardiac pacing signal may synchronize the delivered pulse waveforms with the cardiac cycle. Additionally or alternatively, the pulse waveforms may include a set of levels of a hierarchy. The tissue ablation thus performed may be delivered in synchrony with paced heartbeats. It should be appreciated that any of the ablation devices described herein may be used to ablate tissue using the methods discussed below as appropriate.

Figure 10:
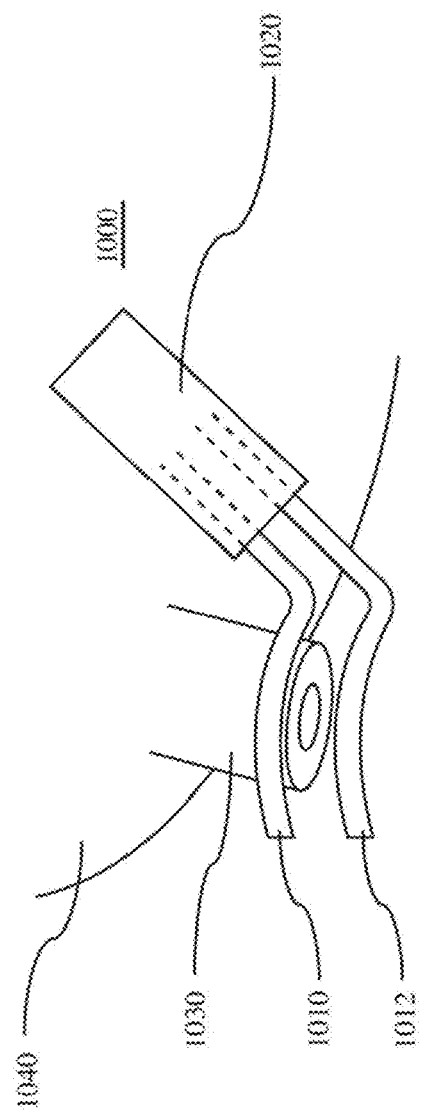
FIG. 10 is a perspective view of a distal end of an ablation device having a pulmonary vein disposed between the arms of the device, according to embodiments.
Figure 11:
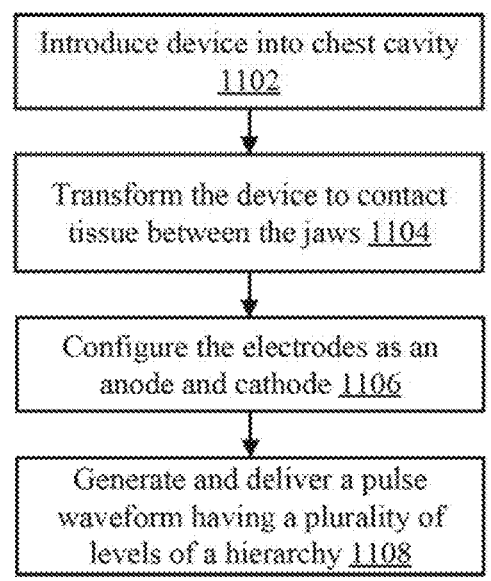
FIG. 11 illustrates a method for tissue ablation, according to embodiments.

As a non-limiting example, in some embodiments, a system may include any of the devices described in the disclosure herein. FIG. 11 is a method (1100) for one embodiment of a tissue ablation process. In some embodiments, the voltage pulse waveforms described herein may be applied during a refractory period of the cardiac cycle to avoid disruption of the sinus rhythm of the heart. Generally, the method (1100) includes introduction of a device (e.g., ablation device, such as the ablation device (100), and/or any of the ablation devices (200, 300, 400, 500, 640, 700, 800, 900, 1000) into a chest cavity of a patient by any suitable means at step (1102). The chest of the patient may be surgically exposed to provide access to a desired ablation site, for example pulmonary vein in the region of the posterior left atrium. For example, the jaws/arms and body of the ablation device may enter the chest cavity at an oblique angle. It may be helpful to angle the jaws/arms in a manner that permits access to a posterior side of a patient's body (where the pulmonary veins may be located) through access from an anterior side of the patient's body. For example, a surgical excision may open and expose the chest cavity. In some embodiments, the ablation device may be advanced in a first configuration where the jaws/arms are closely spaced and/or in contact with each other to aid advancement of the ablation device towards a target tissue (e.g., pulmonary vein). For example, FIG. 10 is a perspective view of a distal end of an ablation device (1000) having a first jaw (1010) and a second jaw (1012) coupled to a pulmonary vein (1030) at a basal location (at the portion of tissue connecting the pulmonary vein to the left atrium) on a posterior side of the left atrium (1040). The ablation device (1000) may be transformed to contact tissue between the jaws/arms at step (1104). For example, the jaws of the ablation device (1000) may transition from a closed configuration to an open configuration to allow a portion of the pulmonary vein (1030) to be held between the jaws (1010, 1020). Saline may be introduced into the chest cavity to at least partially surround the electrodes and create an electrically conductive environment for optimal delivery of current to tissue.

Returning to FIG. 11, at step 1106, the electrodes of the device may be configured in one or more anode/cathode subsets using, for example, the signal generator as described with respect to FIG. 6. For example, electrodes on opposing jaws and which are laterally spaced apart from each other with respect to the longitudinal axis may be configured in anode-cathode sets, as described with respect to FIGS. 8 and 9. This configuration may reduce the risk of shorting and may help generate uniform ablation across the compressed portion of tissue. In some embodiments, one or more electrodes may be configured to receive signal data corresponding to electrocardiography data. Electrocardiography data may be generated for display from the recorded signal data.

In some embodiments, a pacing signal may be generated for cardiac stimulation of the heart. The pacing signal may then be applied to the heart. For example, the heart may be electrically paced with a cardiac stimulator to ensure pacing capture to establish periodicity and predictability of the cardiac cycle. One or more of atrial and ventricular pacing may be applied. An indication of the pacing signal may be transmitted to a signal generator. A time window within the refractory period of the cardiac cycle may then be defined within which one or more voltage pulse waveforms may be delivered. In some embodiments, a refractory time window may follow a pacing signal. For example, a common refractory time window may lie between both atrial and ventricular refractory time windows.

A pulse waveform may be generated in synchronization with the pacing signal (1108). For example, a voltage pulse waveform may be applied in the common refractory time window. In some embodiments, the pulse waveform may be generated with a time offset with respect to the indication of the pacing signal. For example, the start of a refractory time window may be offset from the pacing signal by a time offset. The voltage pulse waveform(s) may be applied over a series of heartbeats over corresponding common refractory time windows.

In some embodiments, hierarchical voltage pulse waveforms having a nested structure and a hierarchy of time intervals as described herein may be useful for irreversible electroporation, providing control and selectivity in different tissue types. A pulse waveform may be generated by a signal generator (e.g., the signal generator 610) and may include a set of levels in a hierarchy. A variety of hierarchical waveforms may be generated with a signal generator as disclosed herein. For example, the pulse waveform may include a first level of a hierarchy of the pulse waveform including a first set of pulses. Each pulse has a pulse time duration and a first time interval separating successive pulses. A second level of the hierarchy of the pulse waveform may include a plurality of first sets of pulses as a second set of pulses. A second time interval may separate successive first sets of pulses. The second time interval may be at least three times the duration of the first time interval. A third level of the hierarchy of the pulse waveform may include a plurality of second sets of pulses as a third set of pulses. A third time interval may separate successive second sets of pulses. The third time interval may be at least thirty times the duration of the second level time interval.

It is understood that while the examples herein identify separate monophasic and biphasic waveforms, it should be appreciated that combination waveforms, where some portions of the waveform hierarchy are monophasic while other portions are biphasic, may also be generated. A voltage pulse waveform having a hierarchical structure may be applied across different anode-cathode subsets (optionally with a time delay). As discussed above, one or more of the waveforms applied across the anode-cathode subsets may be applied during the refractory period of a cardiac cycle. The generated pulse waveform may be delivered to tissue. Accordingly, in the embodiments described herein, a contiguous, transmural zone of ablated tissue may be generated to electrically isolate the pulmonary vein from a main body of the left atrium.

In some embodiments, the pulse waveform may be delivered to pulmonary vein of a heart of a patient via one or more electrodes of a set of jaws of an ablation device. In other embodiments, voltage pulse waveforms as described herein may be selectively delivered to electrode subsets such as paired anode-cathode subsets for ablation and isolation of the pulmonary vein. For example, a first electrode of a first jaw may be configured as an anode and a second electrode of a second jaw may be configured as a cathode. These steps may be repeated for a desired number of pulmonary vein regions to be ablated.

EXAMPLES

Figure 2A:
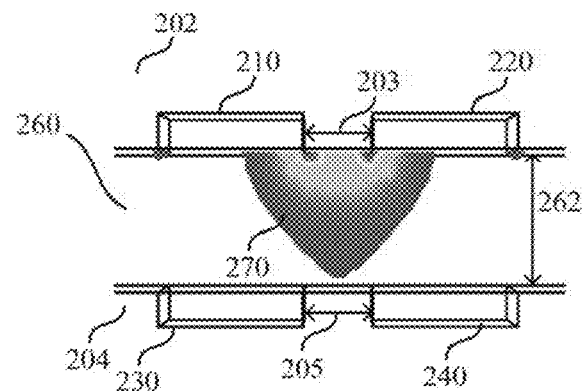
FIG. 2A is a simulation result in the form of a shaded contour plot of the electric potential in a cross-sectional side view of an ablation device, according to embodiments.
Figure 2B:
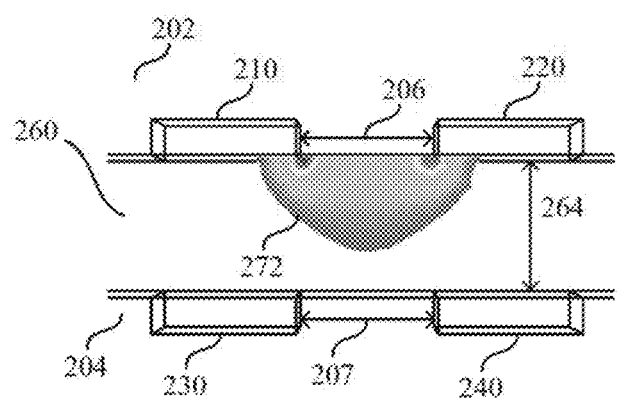
FIG. 2B is a simulation result in the form of a shaded contour plot of the electric potential in a cross-sectional side view of an ablation device with the electrodes spaced further apart than those in FIG. 2A, according to embodiments.
Figure 2C:
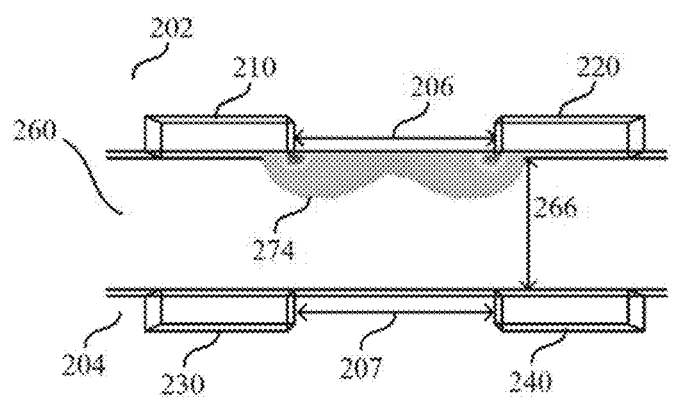
FIG. 2C is a simulation result in the form of a shaded contour plot of the electric potential in a cross-sectional side view of an ablation device with the electrodes spaced further apart than those in FIG. 2B, according to embodiments.

FIGS. 2A-2C depict a set of simulation results in the form of a shaded contour plot of the electric potential in a cross-sectional side view of an ablation device (200) that may be structurally and/or functionally similar to the ablation device in FIG. 6. The ablation device (200) includes a first jaw (202) and a second jaw (204). The first jaw (202) may include a first electrode (210) and a second electrode (220). The second jaw (204) may include a third electrode (230) and a fourth electrode (240). The first jaw (202) and the second jaw (204) may be spaced apart and substantially parallel, and configured to engage tissue (260) therebetween during use. The first jaw (202) and the second jaw (204) may be spaced apart by a third measure (262, 264, 266). The first electrode (210) and the second electrode (220) may be may be disposed on a side of the first jaw (202) facing the second jaw (204). Similarly, the third electrode (230) and the fourth electrode (240) may be disposed on a side of the second jaw (204) facing the first jaw (202). Each electrode (210, 220, 230, 240) may include an exposed portion in electrical contact with tissue (260) during use. The first electrode (210) and the second electrode (220) may be spaced apart by a first measure (203, 206). The third electrode (230) and the fourth electrode (240) may be spaced apart by a second measure (205, 207). The electrodes (210, 220, 230, 240) may be elongate electrodes as described herein. In some embodiments, each electrode (210, 220, 230, 240) may be independently addressable.

In some embodiments, the electrodes configured to deliver energy to tissue (260) may be adjacent electrodes on the same jaw. For example, a first electrode (210) may be configured as an anode and a second electrode (220) may be configured as a cathode. In FIGS. 2A-2C, the first jaw (202) may deliver about 200 V to tissue (260) between first electrode (210) and second electrode (220) to generate respective ablation zones (270, 272, 274) having an electric field strength of about 460 V/cm. The first measure (203, 206) may be 1 mm in FIG. 2A, 2 mm in FIG. 2B, and 3 mm in FIG. 2C. As shown in FIGS. 2A-2C, decreasing separation between electrodes (210, 220) may generate an ablation zone of lesser width and greater depth.

Figure 3A:
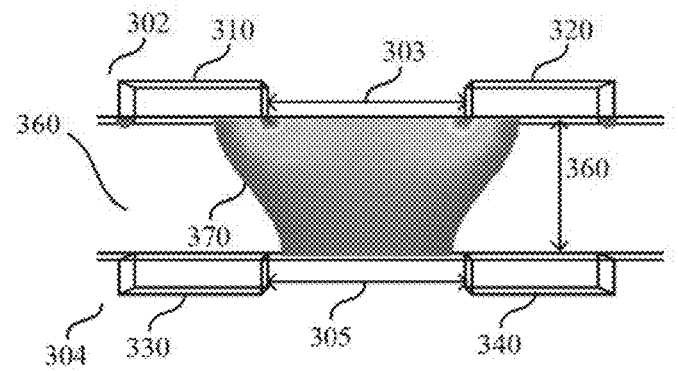
FIG. 3A is a simulation result in the form of a shaded contour plot of the electric potential in a cross-sectional side view of an ablation device, according to embodiments.
Figure 3B:
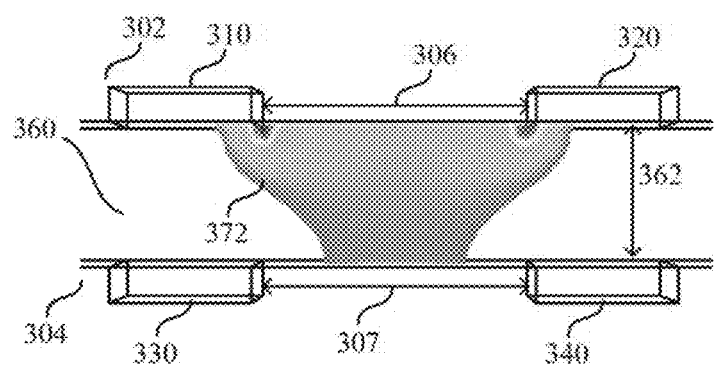
FIG. 3B is a simulation result in the form of a shaded contour plot of the electric potential in a cross-sectional side view of an ablation device with the electrodes spaced further apart than those in FIG. 3A, according to embodiments.
Figure 3C:
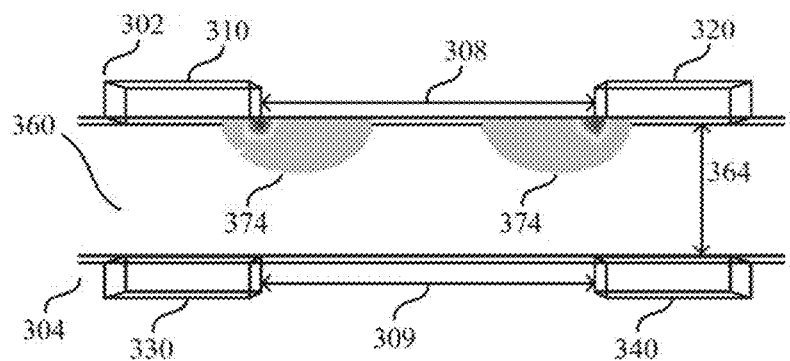
FIG. 3C is a simulation result in the form of a shaded contour plot of the electric potential in a cross-sectional side view of an ablation device with the electrodes spaced further apart than those in FIG. 3B, according to embodiments.

FIGS. 3A-3C depict a set of simulation results in the form of a shaded contour plot of the electric potential in a cross-sectional side view of an ablation device (300). The plots in FIGS. 3A-3C simulate higher voltages and greater separation between electrodes than the plots in FIGS. 2A-2C. The ablation device (300) includes a first jaw (302) and a second jaw (304). The first jaw (302) may include a first electrode (310) and a second electrode (320). The second jaw (304) may include a third electrode (330) and a fourth electrode (340). The first jaw (302) and the second jaw (304) may be spaced apart and substantially parallel and configured to engage tissue (360) therebetween during use. The first jaw (302) and the second jaw (304) may be spaced apart by a third measure (360, 362, 364). The first electrode (310) and the second electrode (320) may be may be disposed on a side of the first jaw (302) facing the second jaw (304). Similarly, the third electrode (330) and the fourth electrode (340) may be disposed on a side of the second jaw (304) facing the first jaw (302). Each electrode (310, 320, 330, 340) may include an exposed portion in electrical contact with tissue (360) during use. The first electrode (310) and the second electrode (320) may be spaced apart by a first measure (303, 306, 308). The third electrode (330) and the fourth electrode (340) may be spaced apart by a second measure (305, 307, 309). The electrodes (310, 320, 330, 340) may be elongate electrodes as described herein. In some embodiments, each electrode (310, 320, 330, 340) may be independently addressable.

In some embodiments, the electrodes configured to deliver energy to tissue (360) may be adjacent electrodes on the same jaw. For example, a first electrode (310) may be configured as an anode and a second electrode (320) may be configured as a cathode. In FIGS. 3A-3C, the first jaw (302) may deliver about 300 V to tissue (360) between first electrode (310) and second electrode (320) to generate respective ablation zones (370, 372, 374) having an electric field strength of about 460 V/cm. The first measure (303, 306, 308) may be 3 mm in FIG. 3A, 4 mm in FIG. 3B, and 5 mm in FIG. 3C. As shown in FIGS. 3A-3C, decreasing separation between electrodes (310, 320) may generate an ablation zone of lesser width and greater depth. A separation of 5 mm in FIG. 3C may generate non-contiguous ablation zones (374).

FIGS. 4A-4E depict a set of simulation results in the form of a shaded contour plot of the electric potential in a cross-sectional side view of an ablation device (400). The plots in FIGS. 4A-4E generate electric fields using electrodes on opposing jaws rather than adjacent electrodes on the same jaw as shown in FIGS. 2A-3C. The ablation device (400) includes a first jaw (402) and a second jaw (404). The first jaw (402) may include a first electrode (410) and a second electrode (420). The second jaw (404) may include a third electrode (430) and a fourth electrode (440). The first jaw (402) and the second jaw (404) may be spaced apart and substantially parallel and configured to engage tissue (460) therebetween during use. The first jaw (402) and the second jaw (404) may be spaced apart by a third measure (460, 462, 464, 466, 468). The first electrode (410) and the second electrode (420) may be may be disposed on a side of the first jaw (402) facing the second jaw (404). Similarly, the third electrode (430) and the fourth electrode (440) may be disposed on a side of the second jaw (404) facing the first jaw (402). Each electrode (410, 420, 430, 440) may include an exposed portion in electrical contact with tissue (460) during use. The first electrode (410) and the second electrode (420) may be spaced apart by a first measure (403). The third electrode (430) and the fourth electrode (440) may be spaced apart by a second measure (405). The electrodes (410, 420, 430, 440) may be elongate electrodes as described herein. In some embodiments, each electrode (410, 420, 430, 440) may be independently addressable.

Figure 4A:
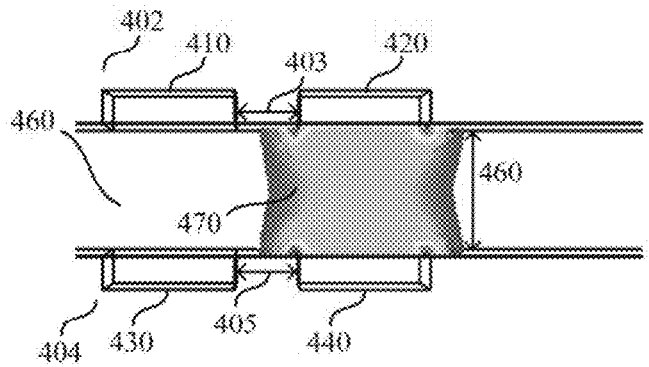
FIG. 4A is a simulation result in the form of a shaded contour plot of the electric potential in a cross-sectional side view of an ablation device, according to embodiments.
Figure 4B:
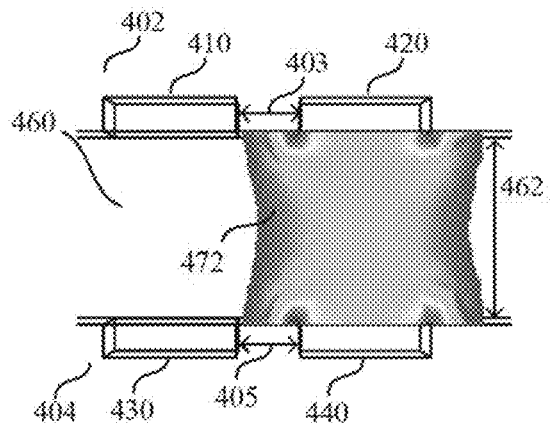
FIG. 4B is a simulation result in the form of a shaded contour plot of the electric potential in a cross-sectional side view of an ablation device with the jaws spaced further apart than those in FIG. 4A, according to embodiments.
Figure 4C:
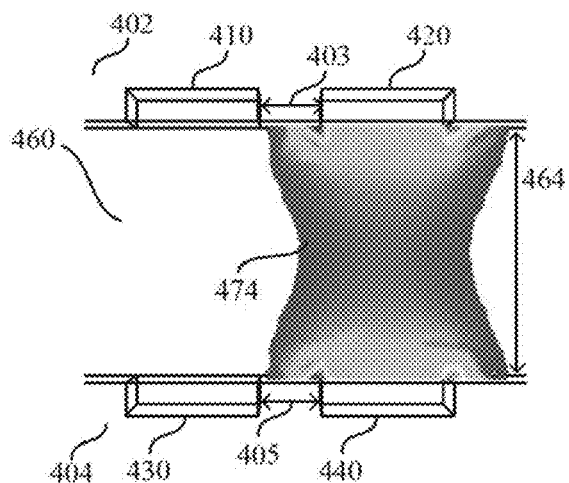
FIG. 4C is a simulation result in the form of a shaded contour plot of the electric potential in a cross-sectional side view of an ablation device with the jaws spaced further apart than those in FIG. 4B, according to embodiments.
Figure 4D:
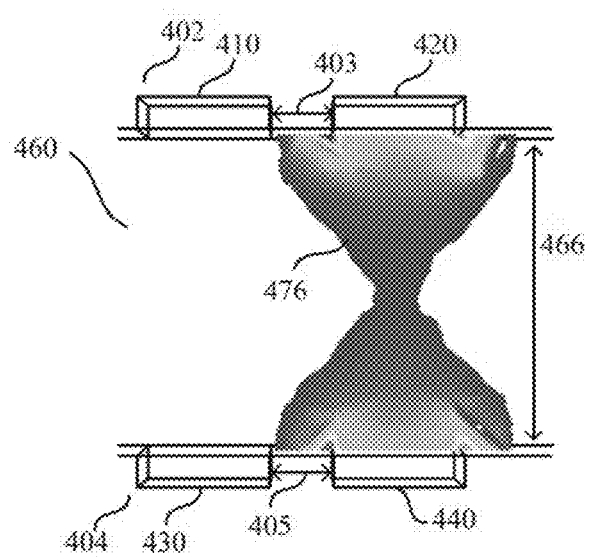
FIG. 4D is a simulation result in the form of a shaded contour plot of the electric potential in a cross-sectional side view of an ablation device with the jaws spaced further apart than those in FIG. 4C, according to embodiments.
Figure 4E:
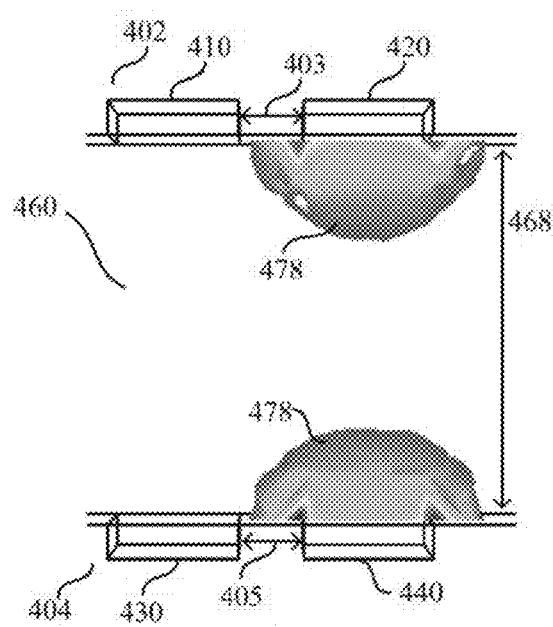
FIG. 4E is a simulation result in the form of a shaded contour plot of the electric potential in a cross-sectional side view of an ablation device with the jaws spaced further apart than those in FIG. 4D, according to embodiments.

In some embodiments, the electrodes configured to deliver energy to tissue (460) may be electrodes that directly oppose each other on different jaws within the cross-section orthogonal to the longitudinal axis. For example, a second electrode (420) may be configured as an anode and a fourth electrode (440) may be configured as a cathode. In FIG. 4A, the first jaw (402) may deliver about 200 V to tissue (460) between second electrode (420) and fourth electrode (440) to generate ablation zones (470) having an electric field strength of about 460 V/cm across a depth of the tissue (460) held by between the jaws (402, 404). In FIGS. 4B-4E, the first jaw (402) may deliver about 300 V to tissue (360) between second electrode (420) and fourth electrode (440) to generate respective ablation zones (470, 472, 474, 476, 478) having an electric field strength of about 460 V/cm. The third measure (460) may be 2 mm in FIG. 4A, third measure (462) may be 3 mm in FIG. 4B, third measure (464) may be and 4 mm in FIG. 4C, third measure (466) may be 5 mm in FIG. 4D, and third measure (468) may be 6 mm in FIG. 4E. As shown in FIGS. 4B-4E, decreasing separation between electrodes (420, 440) may generate an ablation zone of greater intensity. A separation of 6 mm in FIG. 4E may generate non-contiguous ablation zones (478).

FIGS. 5A-5F depict a set of simulation results in the form of a shaded contour plot of the electric potential in a cross-sectional side view of an ablation device (500). The plots in FIGS. 5A-5F generate electric fields using electrodes disposed diagonally on opposing jaws rather than adjacent electrodes on the same jaw as shown in FIGS. 2A-3C. The ablation device (500) includes a first jaw (502) and a second jaw (504). The first jaw (502) may include a first electrode (510) and a second electrode (520). The second jaw (504) may include a third electrode (530) and a fourth electrode (540). The first jaw (502) and the second jaw (504) may be spaced apart and substantially parallel and configured to engage tissue (560) therebetween during use. The first jaw (502) and the second jaw (504) may be spaced apart by a third measure (560, 562, 564, 566, 568, 569). The first electrode (510) and the second electrode (520) may be disposed on a side of the first jaw (502) facing the second jaw (504). Similarly, the third electrode (530) and the fourth electrode (540) may be disposed on a side of the second jaw (504) facing the first jaw (502). Each electrode (510, 520, 530, 540) may include an exposed portion in electrical contact with tissue (560) during use. The first electrode (510) and the second electrode (520) may be spaced apart by a first measure (503). The third electrode (530) and the fourth electrode (540) may be spaced apart by a second measure (505). The electrodes (510, 520, 530, 540) may be elongate electrodes as described herein. In some embodiments, each electrode (510, 520, 530, 540) may be independently addressable.

Figure 5A:
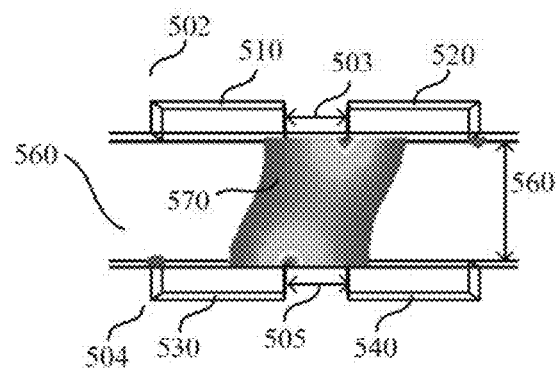
FIG. 5A is a schematic cross-sectional side view of an ablation device generating an electric field, according to embodiments.
Figure 5B:
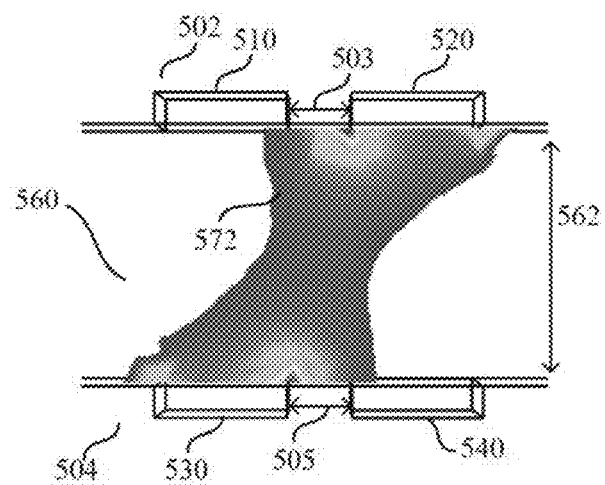
FIG. 5B is a simulation result in the form of a shaded contour plot of the electric potential in a cross-sectional side view of an ablation device with the jaws spaced further apart than those in FIG. 5A, according to embodiments.
Figure 5C:
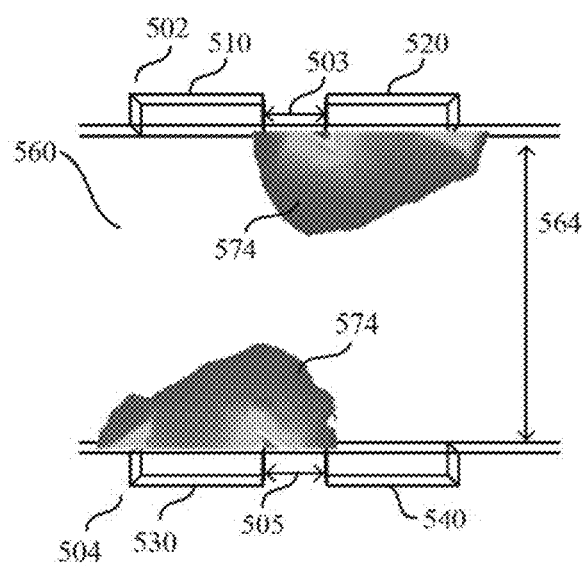
FIG. 5C is a simulation result in the form of a shaded contour plot of the electric potential in a cross-sectional side view of an ablation device with the jaws spaced further apart than those in FIG. 5B, according to embodiments.
Figure 5D:
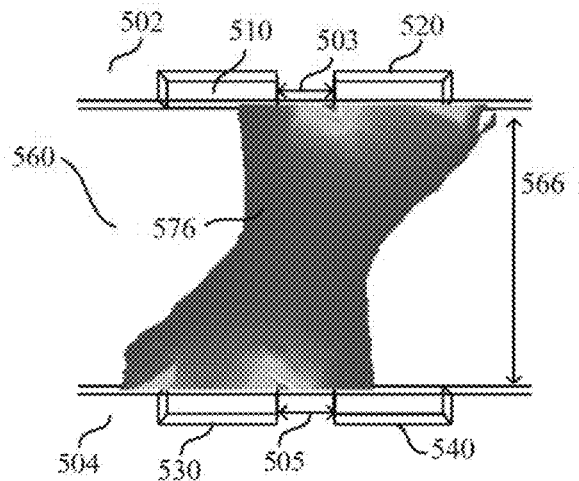
FIG. 5D is a simulation result in the form of a shaded contour plot of the electric potential in a cross-sectional side view of an ablation device using a higher voltage than applied in FIG. 5C, according to embodiments.
Figure 5E:
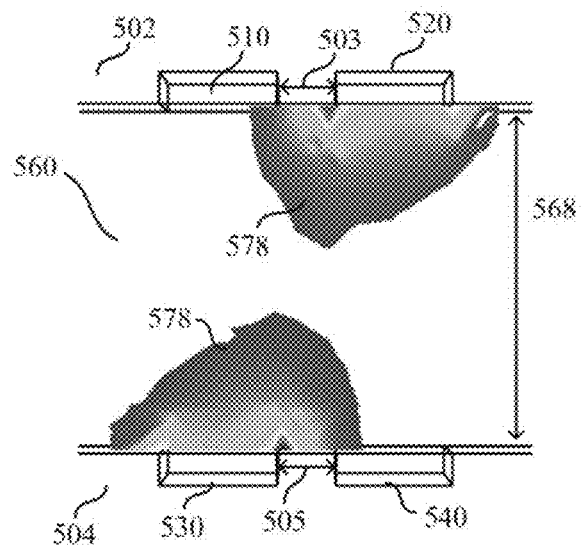
FIG. 5E is a simulation result in the form of a shaded contour plot of the electric potential in a cross-sectional side view of an ablation device with the jaws spaced further apart than those in FIG. 5D, according to embodiments.
Figure 5F:
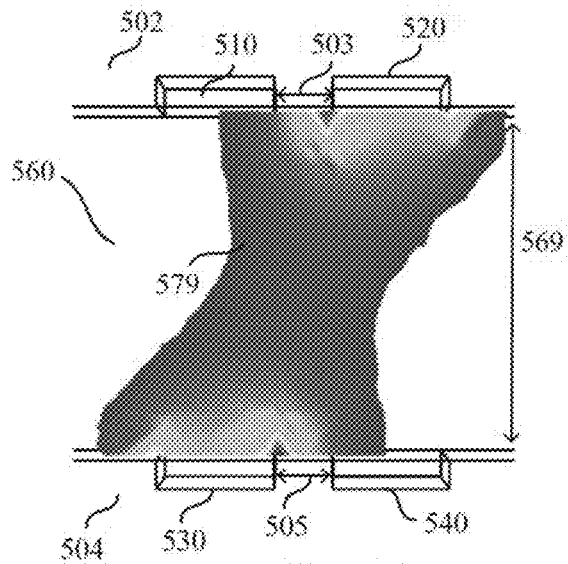
FIG. 5F is a simulation result in the form of a shaded contour plot of the electric potential in a cross-sectional side view of an ablation device using a higher voltage than applied in FIG. 5E, according to embodiments.

In some embodiments, the electrodes configured to deliver energy to tissue (560) may be electrodes that are laterally spaced apart and adjacent on opposing different jaws. For example, a second electrode (520) may be configured as an anode and a third electrode (530) may be configured as a cathode. This anode-cathode configuration of the electrodes reduces the risk of electrical shorting since the anode and cathode will not contact each other even if the jaws are brought into contact with each other. In FIG. 5A, the first jaw (502) may deliver about 200 V to tissue (560) between second electrode (520) and third electrode (540) to generate ablation zone (560) having an electric field strength of about 460 V/cm across a depth of the tissue (460) held between the jaws (502, 504). In FIGS. 5B-5C, the first jaw (502) may deliver about 300 V to tissue (560) between second electrode (520) and third electrode (530) to generate respective ablation zones (572, 574) having an electric field strength of about 460 V/cm. In FIGS. 5D-5E, the first jaw (502) may deliver about 400 V to tissue (560) between second electrode (520) and third electrode (530) to generate respective ablation zones (576, 578) having an electric field strength of about 460 V/cm). In FIG. 5F, the first jaw (502) may deliver about 500 V to tissue (560) between second electrode (520) and third electrode (530) to generate ablation zone (579) having an electric field strength of about 460 V/cm. Thus, by increasing the applied voltage, deeper ablation zones may be produced which may be useful when the tissue between the clamps is relatively thicker. As a set of non-limiting examples, the third measure (560) may be 2 mm in FIG. 5A, third measure (562) may be 4 mm in FIG. 5B, third measure (564) may be and 5 mm in FIG. 5C, third measure (566) may be 5 mm in FIG. 5D, third measure (568) may be 6 mm in FIG. 5E, and third measure (569) may be 6 mm in FIG. 5F.

Pulse Waveform

Disclosed herein are methods, systems and apparatuses for the selective and rapid application of pulsed electric fields/waveforms to effect tissue ablation with irreversible electroporation. The pulse waveform(s) as disclosed herein are usable with any of the systems (600), devices (e.g., 200, 300, 400, 500, 640, 700, 800, 900, 1000), and methods (e.g., 1100) described herein. Some embodiments are directed to pulsed high voltage waveforms together with a sequenced delivery scheme for delivering energy to tissue via sets of electrodes. In some embodiments, peak electric field values may be reduced and/or minimized while at the same time sufficiently large electric field magnitudes may be maintained in regions where tissue ablation is desired. This also reduces the likelihood of excessive tissue damage or the generation of electrical arcing, and locally high temperature increases. In some embodiments, a system useful for irreversible electroporation includes a signal generator and a processor capable of being configured to apply pulsed voltage waveforms to a selected plurality or a subset of electrodes of an ablation device. In some embodiments, the processor is configured to control inputs whereby selected pairs of anode-cathode subsets of electrodes may be sequentially triggered based on a pre-determined sequence, and in one embodiment the sequenced delivery may be triggered from a cardiac stimulator and/or pacing device. In some embodiments, the ablation pulse waveforms are applied in a refractory period of the cardiac cycle to avoid disruption of the sinus rhythm of the heart. One example method of enforcing this is to electrically pace the heart with a cardiac stimulator and ensure pacing capture to establish periodicity and predictability of the cardiac cycle, and then to define a time window well within the refractory period of this periodic cycle within which the ablation waveform is delivered.

In some embodiments, the pulsed voltage waveforms disclosed herein are hierarchical in organization and have a nested structure. In some embodiments, the pulsed waveform includes hierarchical groupings of pulses with a variety of associated timescales. Furthermore, the associated timescales and pulse widths, and the numbers of pulses and hierarchical groupings, may be selected to satisfy one or more of a set of Diophantine inequalities involving the frequency of cardiac pacing.

Pulsed waveforms for electroporation energy delivery as disclosed herein may enhance the safety, efficiency and effectiveness of the energy delivery by reducing the electric field threshold associated with irreversible electroporation, yielding more effective ablative lesions with reduced total energy delivered. This in turn may broaden the areas of clinical application of electroporation including therapeutic treatment of a variety of cardiac arrhythmias.

FIG. 12 illustrates a pulsed voltage waveform in the form of a sequence of rectangular double pulses, with each pulse, such as the pulse (1200) being associated with a pulse width or duration. The pulse width/duration may be about 0.5 microseconds, about 1 microsecond, about 5 microseconds, about 10 microseconds, about 25 microseconds, about 50 microseconds, about 100 microseconds, about 125 microseconds, about 140 microseconds, about 150 microseconds, including all values and sub-ranges in between. The pulsed waveform of FIG. 12 illustrates a set of monophasic pulses where the polarities of all the pulses are the same (all positive in FIG. 12, as measured from a zero baseline). In some embodiments, such as for irreversible electroporation applications, the height of each pulse (1200) or the voltage amplitude of the pulse (1200) may be in the range of about 300 volts, about 1,000 volts, or about 5,000 volts, including all values and sub ranges in between. As illustrated in FIG. 12, the pulse (1200) is separated from a neighboring pulse by a time interval (1202), also sometimes referred to as a first time interval. The first time interval may be about 10 microseconds, about 50 microseconds, about 100 microseconds, about 200 microseconds, about 500 microseconds, about 800 microseconds, about 1 millisecond including all values and sub ranges in between, in order to generate irreversible electroporation.

FIG. 13 introduces a pulse waveform with the structure of a hierarchy of nested pulses. FIG. 13 shows a series of monophasic pulses such as pulse (1300) with pulse width/pulse time duration w, separated by a time interval (also sometimes referred to as a first time interval) such as (1302) of duration $t_1$ between successive pulses, a number $m_1$ of which are arranged to form a group of pulses (1310) (also sometimes referred to as a first set of pulses). Furthermore, the waveform has a number $m_2$ of such groups of pulses (also sometimes referred to as a second set of pulses) separated by a time interval (1312) (also sometimes referred to as a second time interval) of duration $t_2$ between successive groups. The collection of $m_2$ such pulse groups, marked by (1320) in FIG. 13, constitutes the next level of the hierarchy, which may be referred to as a packet and/or as a third set of pulses. The pulse width and the time interval $t_1$ between pulses may both be in the range of microseconds to hundreds of microseconds, including all values and sub ranges in between. In some embodiments, the time interval $t_2$ may be at least three times larger than the time interval $t_1$. In some embodiments, the ratio $t_2/t_1$ may be in the range between about 3 and about 300, including all values and sub-ranges in between.

Figure 14:
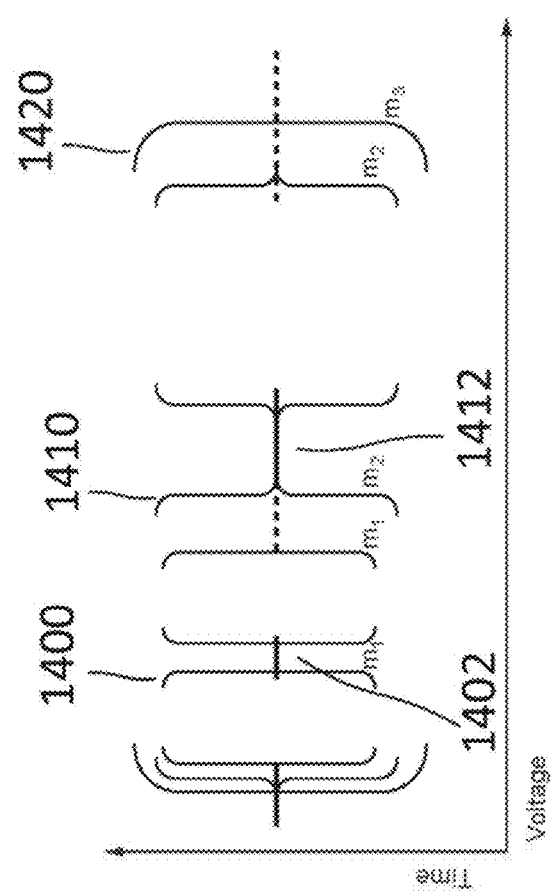
FIG. 14 provides a schematic illustration of a nested hierarchy of monophasic pulses including different levels of the nested hierarchy, according to embodiments.

FIG. 14 further elaborates the structure of a nested pulse hierarchy waveform. In this figure, a series of $m_1$ pulses (individual pulses not shown) form a group of pulses (1400) (e.g., a first set of pulses). A series of $m_2$ such groups separated by an inter-group time interval (1410) of duration $t_2$ (e.g., a second time interval) between one group and the next form a packet 132 (e.g., a second set of pulses). A series of $t_3$ such packets separated by time intervals (1412) of duration $t_3$ (e.g., a third time interval) between one packet and the next form the next level in the hierarchy, a super-packet labeled (1420) (e.g., a third set of pulses) in the figure. In some embodiments, the time interval $t_3$ may be at least about thirty times larger than the time interval $t_2$. In some embodiments, the time interval $t_3$ may be at least fifty times larger than the time interval $t_2$. In some embodiments, the ratio $t_3/t_2$ may be in the range between about 30 and about 800, including all values and sub-ranges in between. The amplitude of the individual voltage pulses in the pulse hierarchy may be anywhere in the range from 300 volts to 7,000 volts or higher, including all values and sub ranges in between.

Figure 15:
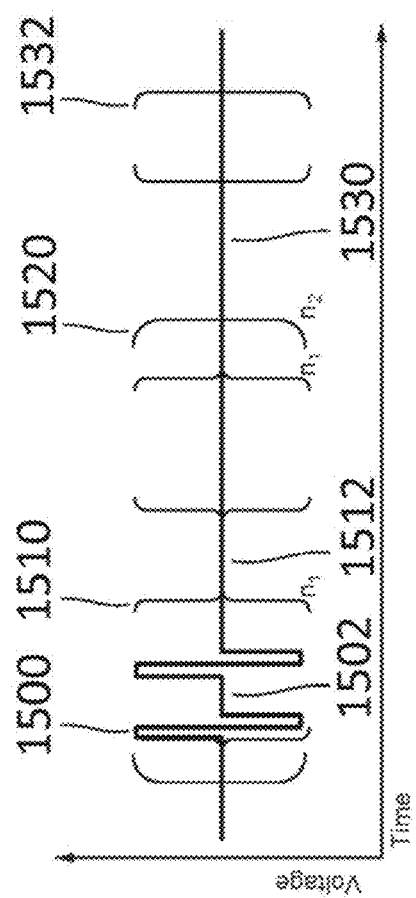
FIG. 15 is a schematic illustration of a nested hierarchy of biphasic pulses including different levels of the nested hierarchy, according to embodiments.

FIG. 15 provides an example of a biphasic waveform sequence with a hierarchical structure. In the example shown in the figure, biphasic pulses such as (1500) have a positive voltage portion as well as a negative voltage portion to complete one cycle of the pulse. There is a time delay (1502) (e.g., a first time interval) between adjacent cycles of duration $t_1$, and $n_1$ such cycles form a group of pulses (1510) (e.g., a first set of pulses). A series of $n_2$ such groups separated by an inter-group time interval (1512) (e.g., a second time interval) of duration $t_2$ between one group and the next form a packet (1520) (e.g., a second set of pulses). The figure also shows a second packet (1530), with a time delay (1532) (e.g., a third time interval) of duration $t_3$ between the packets. Just as for monophasic pulses, higher levels of the hierarchical structure may be formed as well. The amplitude of each pulse or the voltage amplitude of the biphasic pulse may be anywhere in the range from 300 volts to 7,000 volts or higher, including all values and sub ranges in between. The pulse width/pulse time duration may be in the range from nanoseconds or even sub-nanoseconds to tens of microseconds, while the delays $t_1$ may be in the range from zero to several microseconds. The inter-group time interval $t_2$ may be at least ten times larger than the pulse width. In some embodiments, the time interval $t_3$ may be at least about twenty times larger than the time interval $t_2$. In some embodiments, the time interval $t_3$ may be at least fifty times larger than the time interval $t_2$.

Embodiments disclosed herein include waveforms structured as hierarchical waveforms that include waveform elements/pulses at various levels of the hierarchy. The individual pulses such as (1300) in FIG. 13 includes the first level of the hierarchy, and have an associated pulse time duration and a first time interval between successive pulses. A set of pulses, or elements of the first level structure, form a second level of the hierarchy such as the group of pulses/second set of pulses (1310) in FIG. 13. Among other parameters, associated with the waveform are parameters such as a total time duration of the second set of pulses (not shown), a total number of first level elements/first set of pulses, and second time intervals between successive first level elements that describe the second level structure/second set of pulses. In some embodiments, the total time duration of the second set of pulses may be between about 20 microseconds and about 10 milliseconds, including all values and subranges in between. A set of groups, second set of pulses, or elements of the second level structure, form a third level of the hierarchy such as the packet of groups/third set of pulses (1320) in FIG. 13. Among other parameters, there is a total time duration of the third set of pulses (not shown), a total number of second level elements/second set of pulses, and third time intervals between successive second level elements that describe the third level structure/third set of pulses. In some embodiments, the total time duration of the third set of pulses may be between about 60 microseconds and about 200 milliseconds, including all values and sub ranges in between. The generally iterative or nested structure of the waveforms may continue to a higher plurality of levels, such as ten levels of structure, or more.

In some embodiments, hierarchical waveforms with a nested structure and hierarchy of time intervals as described herein are useful for irreversible electroporation ablation energy delivery, providing a good degree of control and selectivity for applications in different tissue types. A variety of hierarchical waveforms may be generated with a suitable pulse generator. It is understood that while the examples herein identify separate monophasic and biphasic waveforms for clarity, it should be noted that combination waveforms, where some portions of the waveform hierarchy are monophasic while other portions are biphasic, may also be generated/implemented.

Figure 16:
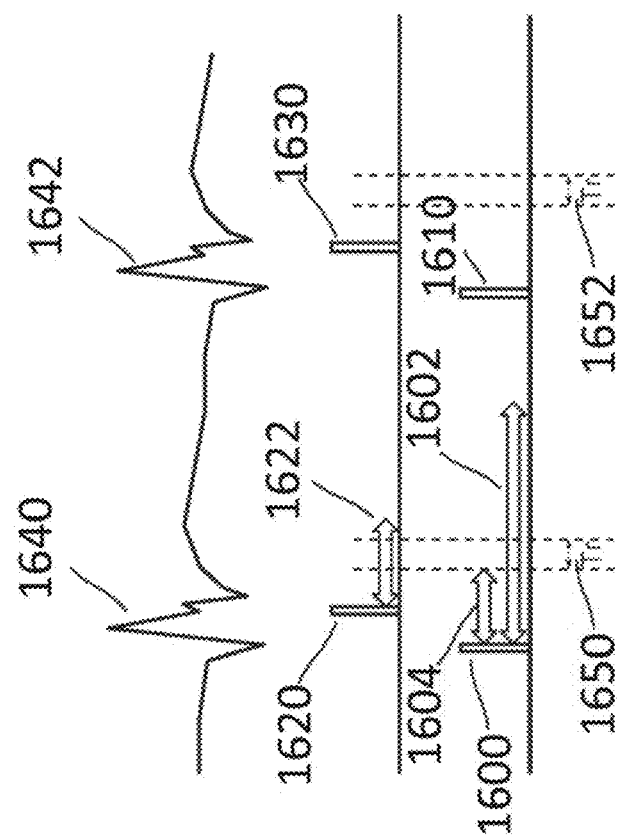
FIG. 16 illustrates schematically a time sequence of electrocardiograms and cardiac pacing signals together with atrial and ventricular refractory time periods and indicating a time window for irreversible electroporation ablation, according to embodiments.

In some embodiments, the ablation pulse waveforms described herein are applied during the refractory period of the cardiac cycle to avoid disruption of the sinus rhythm of the heart. In some embodiments, a method of treatment includes electrically pacing the heart with a cardiac stimulator to ensure pacing capture to establish periodicity and predictability of the cardiac cycle, and then defining a time window within the refractory period of the cardiac cycle within which one or more pulsed ablation waveforms may be delivered. FIG. 16 illustrates an example where both atrial and ventricular pacing is applied (for instance, with pacing leads or catheters situated in the right atrium and right ventricle respectively). With time represented on the horizontal axis, FIG. 16 illustrates a series of ventricular pacing signals such as (1600) and (1610), and a series of atrial pacing signals (1620, 1630), along with a series of ECG waveforms (1640, 1642) that are driven by the pacing signals. As indicated in FIG. 16 by the thick arrows, there is an atrial refractory time window (1622) and a ventricular refractory time window (1602) that respectively follow the atrial pacing signal (1622) and the ventricular pacing signal (1600). As shown in FIG. 16, a common refractory time window (1650) of duration $T_r$ may be defined that lies within both atrial and ventricular refractory time windows (1622, 1602). In some embodiments, the electroporation ablation waveform(s) may be applied in this common refractory time window (1650). The start of this refractory time window (1622) is offset from the pacing signal (1600) by a time offset (1604) as indicated in FIG. 16. The time offset (1604) may be smaller than about 25 milliseconds, in some embodiments. At the next heartbeat, a similarly defined common refractory time window (1652) is the next time window available for application of the ablation waveform(s). In this manner, the ablation waveform(s) may be applied over a series of heartbeats, at each heartbeat remaining within the common refractory time window. In one embodiment, each packet of pulses as defined above in the pulse waveform hierarchy may be applied over a heartbeat, so that a series of packets is applied over a series of heartbeats, for a given electrode set.

It should be understood that the examples and illustrations in this disclosure serve exemplary purposes and departures and variations such as the shape and size of the jaws and electrodes, number of electrodes, and so on may be built and deployed according to the teachings herein without departing from the scope of this invention.

As used herein, the terms "about" and/or "approximately" when used in conjunction with numerical values and/or ranges generally refer to those numerical values and/or ranges near to a recited numerical value and/or range. In some instances, the terms "about" and "approximately" may mean within ±10% of the recited value. For example, in some instances, "about 100 [units]" may mean within ±10% of 100 (e.g., from 90 to 110). The terms "about" and "approximately" may be used interchangeably.

Some embodiments described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which may include, for example, the instructions and/or computer code disclosed herein.

The systems, devices, and/or methods described herein may be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) may be expressed in a variety of software languages (e.g., computer code), including C, C++, Java®, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

The specific examples and descriptions herein are exemplary in nature and embodiments may be developed by those skilled in the art based on the material taught herein without departing from the scope of the present invention, which is limited only by the attached claims.

We claim:

1. An apparatus for ablating heart tissue at an atrial base of a pulmonary vein through irreversible electroporation, the apparatus comprising:

a first jaw and a second jaw, the first jaw and the second jaw being substantially rigid, elongate, and collectively defining a longitudinal axis, the first jaw and the second jaw further configured to be positioned around the atrial base of the pulmonary vein in a first configuration and to be transitioned into a second configuration to clamp the atrial base of the pulmonary vein therebetween;
a first plurality of electrodes disposed on a side of the first jaw facing the second jaw, each electrode of the first plurality of electrodes having a first exposed portion with a height no less than 0.5 mm protruded from the side of the first jaw and, within a cross-section of the apparatus that is orthogonal to the longitudinal axis, a width that is less than a length of that electrode, the first plurality of electrodes spaced apart laterally with respect to the longitudinal axis;
a second plurality of electrodes disposed on a side of the second jaw facing the first jaw, each electrode of the second plurality of electrodes having a second exposed portion with a height greater than 0.5 mm protruded from the side of the second jaw and, within the cross-section, a width that is less than a length of that electrode, the second plurality of electrodes spaced apart laterally with respect to the longitudinal axis;
a routing console coupled to the first and second plurality of electrodes, the routing console coupled to a cardiac stimulator and configured to receive data for synchronization of a pulse waveform with a patient cardiac cycle; and
a processor operatively coupled to the first and second plurality of electrodes via the routing console, the processor configured to:
configure a first electrode of the first plurality of electrodes and a third electrode of the second plurality of electrodes to have a first polarity;
configure a second electrode of the second plurality of electrodes and a fourth electrode of the first plurality of electrodes to have a second polarity opposite the first polarity, the second electrode being disposed diagonally across from the first electrode in the cross-section, the second electrode disposed directly across from the fourth electrode in the cross-section, the first electrode disposed directly across from the third electrode in the cross-section, the third electrode disposed diagonally across from the fourth electrode in the cross-section;
deliver the pulse waveform to the first and second electrodes at a voltage, based on a spacing between the first jaw and the second jaw, such that the first and second electrodes generate an electric field that forms a contiguous ablation zone in the the atrial base of the pulmonary vein via irreversible electroporation that extends diagonally across the the atrial base of the pulmonary vein in the cross-section from the first electrode to the second electrode and extends along the longitudinal axis.

2. The apparatus of claim 1, further comprising: a pulse generator including the processor, the pulse generator configured to generate the pulse waveform having an amplitude of at least 200 Volts.

3. The apparatus of claim 1, wherein the first and second pluralities of electrodes are disposed directly across from each other in the cross-section orthogonal to the longitudinal axis.

4. The apparatus of claim 1, wherein at least two of the first plurality of electrodes are spaced apart by a first measure, and the first jaw and the second jaw are spaced apart by a second measure, wherein a ratio of the second measure to the first measure is between about 0.1:1 and about 12:1.

5. The apparatus of claim 1, wherein a distance between a midpoint of at least two of the first plurality of electrodes in the cross-section is between about 1 mm and about 10 mm.

6. The apparatus of claim 1, wherein any two adjacent electrodes of the first plurality of electrodes are spaced apart by a first measure of between about 0.5 mm and about 10 mm, and any two adjacent electrodes of the second plurality of electrodes are spaced apart by a second measure of between about 0.5 mm and about 10 mm.

7. The apparatus of claim 1, wherein any two adjacent electrodes of the first plurality of electrodes are spaced apart by a first measure and any two adjacent electrodes of the second plurality of electrodes are spaced apart by a second measure, wherein a ratio of the first measure to the second measure is between about 0.05:1 and about 20:1.

8. The apparatus of claim 1, wherein any two adjacent electrodes of the first plurality of electrodes are spaced apart by a measure, wherein a ratio of the width of any electrode of the first plurality of electrodes to the measure is between about 0.01:1 and about 10:1.

9. The apparatus of claim 1, wherein each electrode of the first plurality of electrodes and the second plurality of electrodes has a length parallel to the longitudinal axis of between about 10 mm and about 120 mm.

10. The apparatus of claim 1, wherein each of the first and second jaws has a curved portion.

11. The apparatus of claim 10, wherein the curved portion has a radius of curvature of about 1 cm or larger.

12. The apparatus of claim 1, wherein the first exposed portion of each electrode of the first plurality of electrodes has a flat or convex shape, wherein the second exposed portion of each electrode of the second plurality of electrodes has a flat or convex shape.

13. The apparatus of claim 1, wherein each of the first plurality of electrodes and the second plurality of electrodes includes more than two electrodes.

14. An apparatus for ablating heart tissue at an atrial base of a pulmonary vein through irreversible electroporation, the apparatus, comprising:
a first jaw and a second jaw, the first jaw and the second jaw being substantially rigid, elongate, and collectively defining a longitudinal axis, the first jaw and the second jaw further configured to be positioned around the atrial base of the pulmonary vein in a first configuration and to be transitioned into a second configuration to clamp tissue therebetween;
the first jaw including a first plurality of electrodes having a first electrode and a second electrode disposed on a side of the first jaw facing the second jaw, each electrode of the first plurality of electrodes having a first exposed portion with a height no less than 0.5 mm protruded from the side of the first jaw;
the second jaw including a second plurality of electrodes having a third electrode and a fourth electrode disposed on a side of the second jaw facing the first jaw, each electrode of the second plurality of electrodes having a second exposed portion with a height no less than 0.5 mm protruded from the side of the second jaw, the first electrode being disposed directly across from the third electrode and the second electrode being disposed directly across from the fourth electrode within a cross-section of the apparatus that is orthogonal to the longitudinal axis;

a routing console coupled to the first and second plurality of electrodes, the routing console coupled to a cardiac stimulator and configured to receive data for synchronization of a pulse waveform with a patient cardiac cycle; and a processor operably coupled to the first and second jaw and the routing console, the processor configured to:
configure the first electrode and the third electrode with a first electrical polarity;
configure the second electrode and the fourth electrode with a second electrical polarity opposite to the first electrical polarity; and
deliver the pulse waveform to the electrodes at a voltage, based on a spacing between the first jaw and the second jaw, with the first and second electrical polarities such that the electrodes generate an electric field that forms a contiguous ablation zone in the tissue via irreversible electroporation that extends diagonally across the atrial base of the pulmonary vein in the cross-section from the first electrode to the second electrode and extends along the longitudinal axis.

15. The apparatus of claim 14, wherein the first and second jaws are configured to transition between (1) a first configuration for positioning the first and second jaws around the atrial base of the pulmonary vein and (2) a second configuration for engaging the tissue atrial base of the pulmonary vein.

16. The apparatus of claim 14, wherein a cross-section of the first, second, third, and fourth electrodes are substantially rectangular.

17. The apparatus of claim 14, further comprising: a pulse generator including the processor, the pulse generator configured to generate the pulse waveform having an amplitude of at least 200 Volts.

18. The apparatus of claim 17, wherein the pulse waveform includes a plurality of levels of a hierarchy, the plurality of levels including:
a first level of the hierarchy including a first set of pulses, each pulse of the first set of pulses having a pulse time duration and a first time interval separating successive pulses;
a second level of the hierarchy including a plurality of the first sets of pulses as a second set of pulses, a second time interval separating the second sets of pulses, the second time interval being greater than the duration of the first time interval; and
a third level of the hierarchy including a plurality of the second sets of pulses as a third set of pulses, a third time interval separating the third sets of pulses, the third time interval being the duration of the second level time interval.

19. An apparatus for ablating heart tissue at an atrial base of a pulmonary vein through irreversible electroporation, the apparatus, comprising:
a first jaw and a second jaw, the first jaw and the second jaw being substantially rigid, elongate, and collectively defining a longitudinal axis, the first jaw and the second jaw further configured to be positioned around an anatomical structure the atrial base of the pulmonary vein in a first configuration and to be transitioned into a second configuration to clamp tissue therebetween;
a first plurality of electrodes disposed on a side of the first jaw facing the second jaw, each electrode of the first plurality of electrodes having a first exposed portion with a height no less than 0.5 mm protruded from the side of the first jaw and, within a cross-section of the apparatus that is orthogonal to the longitudinal axis, a width that is less than a length of that electrode, the first plurality of electrodes spaced apart laterally with respect to the longitudinal axis;
a second plurality of electrodes disposed on a side of the second jaw facing the first jaw, each electrode of the second plurality of electrodes having a second exposed portion with a height no less than 0.5 mm protruded from the side of the second jaw and, within the cross-section, a width that is less than a length of that electrode, the second plurality of electrodes spaced apart laterally with respect to the longitudinal axis;
a routing console coupled to the first and second plurality of electrodes, the routing console coupled to a cardiac stimulator and configured to receive data for synchronization of a pulse waveform with a patient cardiac cycle; and
a processor operatively coupled to the first and second plurality of electrodes via the routing console, the processor configured to:
configure a first electrode of the first plurality of electrodes and a third electrode of the second plurality of electrodes to have a first polarity;
configure a second electrode of the second plurality of electrodes and a fourth electrode of the first plurality of electrodes to have a second polarity opposite the first polarity, the first and second electrodes spaced apart laterally with respect to the longitudinal axis, the first electrode and the third electrode being overlapped with each other laterally with respect to the longitudinal axis, the second electrode and the fourth electrode being overlapped with each other laterally with respect to the longitudinal axis; and
deliver the pulse waveform to the first and second electrodes at a voltage, based on a spacing between the first jaw and the second jaw, such that the first and second electrodes generate an electric field that forms a contiguous ablation zone in the atrial base of the pulmonary vein via irreversible electroporation that extends from the first electrode to the second electrode and extends along the longitudinal axis.

20. The apparatus of claim 19, further comprising: a pulse generator including the processor, the pulse generator configured to generate the pulse waveform having an amplitude of at least 200 Volts.

21. The apparatus of claim 19, wherein the first and second electrodes are adjacent electrodes of the first plurality of electrodes.

22. The apparatus of claim 21, wherein the first and second electrodes are spaced apart by a measure of between about 0.5 mm and about 10 mm.

23. The apparatus of claim 21, wherein the first and second electrodes are spaced apart by a measure, wherein a ratio of the width of the first or second electrode to the measure is between about 0.01:1 and about 10:1.

* * * * *